United States Patent [19]
Brookes et al.

[11] 3,952,001
[45] Apr. 20, 1976

[54] 1-CARBAMOYL-1,2,4-TRIAZOLES

[75] Inventors: Robert Frederick Brookes, Tollerton; David Henry Godson, Chilwell; Douglas Greenwood; Margaret Tulley, both of Nottingham; Stanley Brice Wakerley, Burton Joyce, all of England

[73] Assignee: The Boots Company Limited, Nottingham, England

[22] Filed: Dec. 21, 1972

[21] Appl. No.: 317,453

Related U.S. Application Data

[63] Continuation-in-part of Ser. No. 261,206, June 9, 1972, abandoned, which is a continuation-in-part of Ser. No. 153,448, June 15, 1971, abandoned.

[30] Foreign Application Priority Data
July 1, 1970 United Kingdom............... 31922/70
Mar. 31, 1971 United Kingdom................. 8275/71

[52] U.S. Cl................................ 260/308 R; 71/92; 260/247.1 M; 260/268 H; 260/287 R; 260/293.69
[51] Int. Cl.$^2$............... C07D 249/12; C07D 403/12; C07D 413/12
[58] Field of Search................................ 260/308 R

[56] References Cited
UNITED STATES PATENTS
3,308,131   3/1967   McKusick....................... 260/308 R Primary Examiner—Alton D. Rollins
Attorney, Agent, or Firm—Lawrence Rosen; E. Janet Berry

[57] ABSTRACT

Novel 1-carbamoyl-1,2,4-triazoles, processes for their production, and herbicidal compositions and methods are described. The compounds are particularly useful for the pre-weed emergence control of the graminaceous weeds crabgrass, barnyard grass, yellow foxtail and Johnson grass.

11 Claims, No Drawings

1-CARBAMOYL-1,2,4-TRIAZOLES

This application is a continuation-in-part of copending application Ser. No. 261,206, filed 9th June 1972, now abandoned which is in turn a continuation-in-part of application Ser. No. 153,448, filed 15th June 1971, now abandoned.

The invention relates to new chemical compounds with herbicidal activity. More particularly, this invention relates to new 1,2,4-triazoles, herbicidal compositions containing these compounds as active ingredients, and the use of these compounds to control weeds.

In U.S. Pat. No. 3,308,131 there is described a broad group of 1,2,4-triazoles of the isomeric general formulae

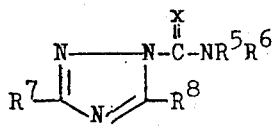

and

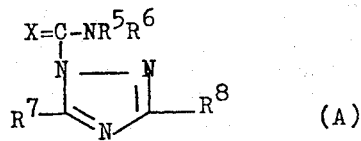

(A)

wherein X is oxygen or sulphur, $R^5$ and $R^6$ are aliphatic groups which together contain up to 14 carbon atoms and which may be joined to form a heterocyclic ring with the carbamoyl nitrogen atom, and $R^7$ and $R^8$, which together contain up to 14 carbon atoms, are free from aliphatic unsaturation and are selected from hydrogen, halogen, sulphonyl, mercapto, cyano, hydrocarbyl, halohydrocarbyl, nitrohydrocarbyl, hydrocarbyloxycarbonylhydrocarbyl, hydrocarbylsulphonyl, hydrocarbylmercapto, nitrohydrocarbylmercapto, halohydrocarbylmercapto, aminohydrocarbylmercapto and hydrocarbyloxyhydrocarbyl. The compounds in this group are stated to be effective insecticides, particularly against mites and aphids. In addition, some of the compounds are stated to have analgesic properties.

We have now found that advantageous are valuable herbicidal properties are possessed by a relatively narrow group of new 1,2,4-triazoles, some of which compounds are encompassed by the broad group of 1,2,4-triazoles defined above.

The new 1,2,4-triazoles provided by the present invention are 1-N,N-disubstituted-carbamoyl-1,2,4-triazoles with a sulphur function in the 3-position, selected from the group consisting of a. a compound of the formula

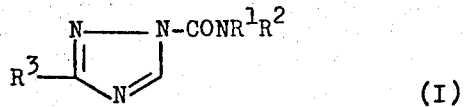

(I)

in which $R^3$ is alkylthio containing 2 – 5 carbon atoms, alkylsulphinyl containing 3 – 5 carbon atoms, alkylsulphonyl containing 1 – 5 carbon atoms or alkenylthio containing 3 or 4 carbon atoms, $R^1$ is alkyl containing 2 – 6 carbon atoms, allyl or 2-methylallyl, and $R^2$ is alkyl containing 2 or 3 carbon atoms, allyl, 2-methylallyl or prop-2-ynyl, the total number of carbon atoms in $R^1$ and $R^2$ together being 4 – 9 inclusive;

b. a compound of the formula

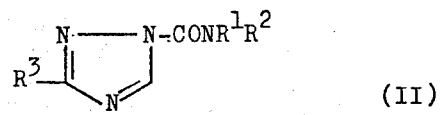

(II)

in which $R^3$ is alkylsulphonyl containing 1 – 5 carbon atoms, alkenyloxyalkylthio containing 4 – 6 carbon atoms, alkoxyalkylsulphinyl containing 2 – 6 carbon atoms, alkoxyalkylsulphonyl containing 2 – 6 carbon atoms, haloalkylsulphinyl containing 2 – 5 carbon atoms or haloalkylsulphonyl containing 1 – 5 carbon atoms, $R^1$ is alkyl containing 2 – 6 carbon atoms, allyl, 2-methylallyl, alkoxyalkyl containing 2 – 6 carbon atoms, alkenyloxyalkyl containing 4 – 6 carbon atoms, haloalkyl containing 2 – 6 carbon atoms, 2-haloallyl or 2,3-dihaloallyl, and $R^2$ is alkyl containing 2 or 3 carbon atoms, allyl, 2-methylallyl, prop-2-ynyl, alkoxyalkyl containing 2, 3 or 4 carbon atoms, haloalkyl containing 2 or 3 carbon atoms, 2,3-dihaloallyl or cyclopropyl, provided that $R^2$ is cyclopropyl or that at least one of the groups $R^1$, $R^2$ and $R^3$ contains an alkoxy substituent or one or two halo substituents; and c. a compound of the formula

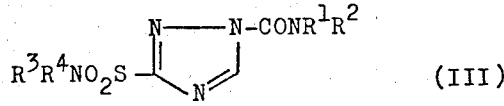

(III)

in which $R^1$ is alkyl containing 1 or 2 carbon atoms, allyl, 2-methylallyl, prop-2-ynyl, alkoxyalkyl containing 2–4 carbon atoms, haloalkyl containing 1–4 carbon atoms, 2-haloallyl, 2,3-dihaloallyl or cyclopropyl, $R^2$ is alkyl containing 2–8 carbon atoms, alkenyl containing 2–8 carbon atoms, alkenyloxyalkyl containing 4–8 carbon atoms (for example allyloxyalkyl or (2-methylallyl)oxyalkyl), haloalkyl containing 2–8 carbon atoms, 2-haloallyl, 2,3-dihaloallyl, cyclopropyl or cyclohexyl, $R^3$ is alkyl containing 1–4 carbon atoms, allyl, 2-methylallyl, prop-2-ynyl, alkoxyalkyl containing 2–4 carbon atoms, haloalkyl containing 1–4 carbon atoms, 2-haloallyl, 2,3-dihaloallyl, cyclopropyl or phenyl containing 1–3 halo substituents, $R^4$ is alkyl containing 1–8 carbon atoms, alkenyl containing 2–8 carbon atoms, alkoxyalkyl containing 2–8 carbon atoms, alkenyloxyalkyl containing 4–8 carbon atoms (for example allyloxyalkyl or (2-methylallyl)oxyalkyl), haloalkyl containing 1– 8 carbon atoms, 2-haloallyl, 2,3-dihaloallyl, cyclopropyl, or cyclohexyl, or $R^3$ and $R^4$, together with the nitrogen atom to which they are attached, form a heterocyclic ring, optionally containing 1–4 lower alkyl (preferably methyl) substituents, selected from morpholino, pyrrolidino, 1-piperidyl, hexamethyleneimino and heptamethyleneimino, provided that the total number of carbon atoms in $R^1$ and $R^2$ together is 3–9 inclusive, and when $R^3$ is a radical not containing a phenyl nucleus, the total number of carbon atoms in $R^3$ and $R^4$ together is 2–9 inclusive.

COMPOUNDS OF FORMULA I

According to one feature of the present invention there are provided new compounds of the general formula I, in which $R^3$ is alkylthio containing 2–5 carbon atoms, alkylsulphinyl containing 3–5 carbon atoms, alkylsulphonyl containing 1–5 carbon atoms or alkenylthio containing 3 or 4 carbon atoms, $R^1$ is alkyl containing 2–6 carbon atoms, allyl or 2-methylallyl, and $R^2$ is alkyl containing 2 or 3 carbon atoms, allyl, 2-methylallyl or prop-2-ynyl, the total number of carbon atoms in $R^1$ and $R^2$ together being 4–9 inclusive.

The alkyl or alkenyl radical in the group $R^3$ may have a straight or branched chain, and is preferably a primary or secondary radical. Typical values of $R^3$ include, for example methylsulphonyl, ethylthio, ethylsulphonyl, propylthio, propylsulphinyl, propylsulphonyl, isopropylthio, isopropylsulphinyl, isopropylsulphonyl, n-butylthio, n-butylsulphinyl, n-butylsulphonyl, isobutylthio, isobutylsulphinyl, isobutylsulphonyl, sec. butylthio sec. butylsulphinyl, sec.butylsulphonyl, n-pentylthio, n-pentylsulphinyl, n-pentylsulphonyl, isopentylthio, isopentylsulphinyl, isopentylsulphonyl, allylthio, 2-methylallylthio and but-2-enylthio.

The radicals $R^1$ and $R^2$ may be straight chain or branched chain radicals, and are preferably primary or secondary radicals. Typical values of $R^1$ include, for example, ethyl, propyl, isopropyl, n-butyl, isobutyl, sec.butyl, n-pentyl, isopentyl, n-hexyl, allyl and 2-methylallyl. Typical values of $R^2$ include, for example, ethyl, propyl, isopropyl, allyl, 2-methylallyl and prop-2-ynyl.

Typical values of the carbamoyl radical —CONR$^1$R$^2$ include, for example, diethylcarbamoyl, diallylcarbamoyl, dipropylcarbamoyl, N-propyl-N-prop-2-ynylcarbamoyl, N-allyl-N-ethylcarbamoyl, N-allyl-N-propylcarbamoyl, N-allyl-N-n-butylcarbamoyl, N-allyl-N-isobutylcarbamoyl, N-allyl-N-n-pentylcarbamoyl, N-allyl-N-isopentylcarbamoyl, N-allyl-N-n-hexylcarbamoyl, N-isopropyl-N-propylcarbamoyl, di(isopropyl)carbamoyl, N-ethyl-N-propylcarbamoyl, N-ethyl-N-n-butylcarbamoyl, N-ethyl-N-n-pentylcarbamoyl, N-ethyl-N-n-hexylcarbamoyl, N-propyl-N-n-butylcarbamoyl, N-propyl-N-n-pentylcarbamoyl, N-propyl-N-n-hexylcarbamoyl, di(2-methylallyl)carbamoyl, N-propyl-N-isobutylcarbamoyl, N-propyl-N-sec.butylcarbamoyl and N-ethyl-N-isopentylcarbamoyl.

Preferred compounds of the present invention are those of the hereinbefore defined general formula I in which A. $R^3$ is alkylsulphonyl and the carbamoyl group CONR$^1$R$^2$ is diallylcarbamoyl, dialkylcarbamoyl, N-allyl-N-alkylcarbamoyl wherein the alkyl radical contains 2 – 6 carbon atoms, or N-alkyl-N-prop-2-ynylcarbamoyl, B. $R^3$ is alkylsulphinyl containing 3 – 5 carbon atoms and the carbamoyl group CONR$^1$R$^2$ is diallylcarbamoyl, dipropylcarbamoyl, diethylcarbamoyl, N-allyl-N-alkylcarbamoyl, wherein the alkyl radical contains 2 – 6 carbon atoms, or N-alkyl-N-prop-2-ynylcarbamoyl, and C. $R^3$ is alkylthio and the carbamoyl group CONR$^1$R$^2$ is diallylcarbamoyl, N-allyl-N-alkylcarbamoyl wherein the alkyl radical contains 2 – 6 carbon atoms, or N-alkyl-N-prop-2-ynylcarbamoyl.

The present invention also provides herbicidal compositions which comprise as an active ingredient a compound of the hereinbefore defined formula I in association with a diluent or carrier. The diluent or carrier may be a solid or liquid, optionally in association with a surface-active agent, for example a dispersing agent, emulsifying agent or wetting agent.

According to a further feature of the invention there is provided a method for the pre-weed emergence control of graminaceous weeds which comprises applying to the locus of the weeds, for example the soil, a compound of the formula I. A particular embodiment of this feature is a method for the selective pre-weed emergence control of graminaceous weeds such as barnyard grass, crabgrass, yellow foxtail and Johnson grass in a crop area which comprises applying to the crop area a compound of the formula I at an application rate sufficient to control the weeds but substantially non-phytotoxic to the crop.

COMPOUNDS OF FORMULA II

The present invention provides new compounds of the general formula II in which $R^3$ is alkylsulphonyl containing 1 – 5 carbon atoms, alkenyloxyalkylthio containing 4 – 6 carbon atoms, alkoxyalkylsulphinyl containing 2 – 6 carbon atoms, alkoxyalkylsulphonyl containing 2 – 6 carbon atoms, haloalkylsulphinyl containing 2 – 5 carbon atoms or haloalkylsulphonyl containing 1 – 5 carbon atoms, $R^1$ is alkyl containing 2–6 carbon atoms, allyl, 2-methylallyl, alkoxyalkyl containing 2 – 6 carbon atoms, alkenyloxyalkyl containing 4 – 6 carbon atoms, haloalkyl containing 2 – 6 carbon atoms, 2-haloallyl or 2,3-dihaloallyl, and $R^2$ is alkyl containing 2 or 3 carbon atoms, allyl, 2-methylallyl, prop-2-ynyl, alkoxyalkyl containing 2, 3 or 4 carbon atoms, haloalkyl containing 2 or 3 carbon atoms, 2,3-dihaloallyl or cyclopropyl, provided that $R^2$ is cyclopropyl or that at least one of the groups $R^1$, $R^2$ and $R^3$ contains an alkoxy substituent or one or two halo substituents.

Preferably any alkoxy or halo substituent in an alkoxyalkyl or haloalkyl radical is attached in a position other than the alpha position, i.e. is attached to a carbon atom other than that which is attached to the nitrogen atom of the carbamoyl group CONR$^1$R$^2$ or the sulphur atom of the group $R^3$. Under these circumstances, when $R^3$ is alkoxyalkylsulphinyl or alkoxyalkylsulphonyl, it contains 3 – 6 carbon atoms, when $R^3$ is haloalkylsulphonyl it contains 2 – 5 carbon atoms when $R^3$ is alkenyloxyalkylthio it contains 5 or 6 carbon atoms, when $R^1$ is alkoxyalkyl it contains 3 – 6 carbon atoms, when $R^1$ is alkenyloxyalkyl it contains 5 or 6 carbon atoms, and when $R^2$ is alkoxyalkyl it contains 3 or 4 carbon atoms. An alkenyloxyalkyl radical is, for example, allyloxyalkyl or (2-methylallyl)oxyalkyl.

The term "halo" includes chloro, bromo and fluoro and is preferably chloro or bromo, especially chloro. The term "alkoxy" includes alkoxy radicals with 1, 2, 3 or 4 carbon atoms, for example methoxy, ethoxy, propoxy, isopropoxy, n-butoxy and isobutoxy.

The alkyl, alkenyl, alkoxyalkyl or haloalkyl radical is the group $R^3$ may have a straight or branched chain, and is preferably a primary or secondary radical. The alkoxyalkyl radical in $R^3$ may contain 2, 3, 4, 5 or 6 carbon atoms and may be, for example, 2-methoxyethyl, 2-ethoxyethyl, 2-propoxyethyl, 2-n-butoxyethyl, 3-methoxypropyl, 3-ethoxypropyl, 2-methoxypropyl or 2-ethoxypropyl. The haloalkyl radical in $R^3$ may contain 2, 3, 4 or 5 carbon atoms and may be, for example, 2-chloroethyl, 2-bromoethyl, 2-fluoroethyl, 3-chloropropyl, 3-bromopropyl, 4-chlorobutyl, 4-bromobutyl or 5-chloropentyl.

Values of $R^3$ include, for example, 2-methoxyethylsulphinyl, 2-ethoxyethylsulphinyl, 2-propoxyethylsulphinyl, 2-n-butoxyethylsulphinyl, 3-methoxypropylsulphinyl, 3-ethoxypropylsulphinyl, 2-methoxypropylsulphinyl, 2-ethoxypropylsulphinyl, 2-chloroethylsulphinyl, 2-chloroethylsulphonyl, 2-bromoethylsulphinyl, 2-bromoethylsulphonyl, 3-chloropropylsulphinyl, 3-chloropropylsulphonyl, 4-chlorobutylsulphinyl, 4-chlorobutylsulphonyl, 2-chloroallylsulphinyl, 2-chloroallylsulphonyl, 2,3-dichloroallylsulphinyl, 2,3-dichloroallylsulphonyl, 2-allyloxyethylthio and 3-allyloxypropylthio.

$R^3$ is preferably alkylsulphonyl or alkoxyalkylsulphonyl, such as for example, methylsulphonyl, ethylsulphonyl propylsulphonyl, isopropylsulphonyl, n-butylsulphonyl, isobutylsulphonyl, sec.butylsulphonyl, 2-methoxyethylsulphonyl, 2-ethoxyethylsulphonyl 2-propoxyethylsulphonyl, 2-n-butoxyethylsulphonyl, 3-methoxypropylsulphonyl, 3-ethoxypropylsulphonyl, 2-methoxypropylsulphonyl, 2-ethoxypropylsulphonyl, 1-methyl-2-propoxyethylsulphonyl. Especially suitable groups are alkylsulphonyl containing 2–4 carbon atoms, and alkoxyalkylsulphonyl containing 3 to 5 carbon atoms.

The radicals $R^1$ and $R^2$ may be straight or branched chain radicals, and are preferably primary or secondary radicals. Typical values of $R^1$ include, for example, ethyl propyl, isopropyl, n-butyl, isobutyl, sec.butyl, n-pentyl, isopentyl, allyl, methoxymethyl, 2-methoxyethyl, 2-ethoxyethyl, 2-propoxyethyl, 2-n-butoxyethyl, 3-methoxypropyl, 3-ethoxypropyl, 2-allyloxyethyl, 3-allyloxypropyl, 2-methoxypropyl, 2-ethoxypropyl, 2-chloroethyl, 2-bromoethyl, 2-fluoroethyl, 3-chloropropyl, 3-bromopropyl, 4-chlorobutyl, 4-bromobutyl, 5-chloropentyl, 6-chlorohexyl, 2-chloroallyl, 2-bromoallyl, 2,3-dichloroallyl and 2,3-dibromoallyl. Typical values of $R^2$ include, for example, ethyl, propyl, isopropyl, allyl, 2-methylallyl, prop-2-ynyl, 2-methoxyethyl, 2-ethoxyethyl, 2-chloroethyl, 2-bromoethyl, 3-chloropropyl, 3-bromopropyl, 2-chloroallyl, 2-bromoallyl, 2,3-dichloroallyl, 2,3-dibromoallyl and cyclopropyl.

Typical values of the carbamoyl radical —$CONR^1R^2$ include, for example, dialkylcarbamoyl wherein the alkyl radicals are the same or different [for example diethylcarbamoyl, dipropylcarbamoyl, N-ethyl-N-propylcarbamoyl, N-butyl-N-ethylcarbamoyl, N-ethyl-N-hexylcarbamoyl, N-propyl-N-isopropylcarbamoyl, N-propyl-N-sec.butylcarbamoyl], diallylcarbamoyl, N-propyl-N-prop-2-ynylcarbamoyl, N-allyl-N-alkylcarbamoyl wherein the alkyl radical contains 2- 6 carbon atoms [for example N-allyl-N-ethylcarbamoyl, N-allyl-N-propylcarbamoyl, N-allyl-N-n-butylcarbamoyl, N-allyl-N-isobutylcarbamoyl, N-allyl-N-n-pentylcarbamoyl, N-allyl-N-isopentylcarbamoyl, N-allyl-N-n-hexylcarbamoyl], N-allyl-N-(2-methoxyethyl)carbamoyl, N-allyl-N-(2-ethoxy ethyl)carbamoyl and N-allyl-N-(2-chloroethyl)carbamoyl, N-alkyl-N-methoxymethylcarbamoyl wherein the alkyl radical contains 2 – 6 carbon atoms [for example N-propyl-N-methoxymethylcarbamoyl], N-alkyl-N-(2-methoxyethyl)carbamoyl wherein the alkyl radical contains 2 – 6 carbon atoms [for example N-ethyl-N-(2-methoxyethyl)carbamoyl, N-propyl-N-(2-methoxyethyl)carbamoyl and N-butyl-N-(2-methoxyethyl)carbamoyl]-N-alkyl-N-(2-ethoxyethyl)carbamoyl wherein the alkyl radical contains 2 – 6 carbon atoms [for example N-ethyl-N-(2-ethoxyethyl)-carbamoyl and N-propyl-N-(2-ethoxyethyl)carbamoyl], N-alkyl-N-(3-methoxypropyl)carbamoyl wherein the alkyl radical contains 2 – 6 carbon atoms, N-alkyl-N-(2-propoxyethyl)carbamoyl wherein the alkyl radical contains 2 or 3 carbon atoms, N-alkyl-N-(2-isopropoxyethyl)carbamoyl wherein the alkyl radical contains 2 or 3 carbon atoms, N-alkyl-N-(2-chloroallyl)-carbamoyl wherein the alkyl radical contains 2 – 6 carbon atoms [for example N-propyl-N-(2-chloroallyl)carbamoyl], N-alkyl-N-(2,3-dichlorallyl)carbamoyl wherein the alkyl radical contains 2 – 6 carbon atoms and N-alkyl-N-(2-chloroethyl)carbamoyl wherein the alkyl radical contains 2 – 6 carbon atoms.

When the compound of formula II contains an alkoxy substituent, $R^3$ is suitably alkylsulphonyl containing 2 – 4 carbon atoms or alkoxyalkylsulphonyl containing 3 – 5 carbon atoms. The carbamoyl group $CONR^1R^2$ is suitably dialkylcarbamoyl, N-alkyl-N-allylcarbamoyl, diallylcarbamoyl, N-alkyl-N-propynylcarbamoyl, N-alkyl-N-alkoxyalkylcarbamoyl, or N-allyl-N-alkoxyalkylcarbamoyl.

Preferred compounds of formula II having one or more alkoxy substituents are those in which:

a. $R^3$ is alkylsulphonyl, the alkyl group containing 2, 3 or 4 carbon atoms, and the carbamoyl group $CONR^1R^2$ is N-alkyl-N-alkoxyalkylcarbamoyl or N-allyl-N-alkoxyalkylcarbamoyl, the alkyl group containing 2, 3 to 4 carbon atoms and the alkoxyalkyl groups containing 3 to 4 carbon atoms, especially 2-methoxyethyl, 2-methoxypropyl or 2-ethoxyethyl, and b. $R^3$ is alkoxyalkylsulphonyl, the alkoxyalkyl group containing 3 to 5 carbon atoms, especially 2-methoxyethyl, 3-methoxypropyl, 2-ethoxyethyl, 2-propoxyethyl, 2-isopropoxyethyl, and the carbamoyl group $CONR^1R^2$ is diallylcarbamoyl, N-alkyl-N-carbamoyl, N-alkyl-N-propynylcarbamoyl or dialkylcarbamoyl, the alkyl groups containing 2, 3 or 4 carbon atoms.

When the compound of formula II contains a halo atom a preferred group of compounds is one in which $R^3$ is alkylsulphonyl containing 2 or 3 carbon atoms or alkoxyalkylsulphonyl containing 3 to 5 carbon atoms. Preferably the carbamoyl group $CONR^1R^2$ is N-alkyl-N-(2-haloallyl)carbamoyl in which the alkyl group contains 2 – 4 carbon atoms and the halo atom is chlorine.

When $R^2$ is cyclopropyl a preferred group of compounds is one in which $R^3$ is alkylsulphonyl containing 2 – 4 carbon atoms, or alkoxyalkylsulphonyl containing 3 – 5 carbon atoms. Preferably the carbamoyl group $CONR^1R^2$ is N-cyclopropyl-N-alkylcarbamoyl in which the alkyl group contains 2, 3 or 4 carbon atoms.

The present invention also provides herbicidal compositions which comprise as an active ingredient a compound of the hereinbefore defined general formula II in association with a diluent or carrier. The diluent or carrier may be solid or liquid, optionally in association with a surface-active agent, for example a dispersing agent, emulsifying agent or wetting agent.

According to a further feature of the present invention there is provided a method for the pre-weed emergence control of graminaceous weeds which comprises applying to the locus of the weeds, for example the soil, a compound of the general formula II. A particular embodiment of this feature is a method for the selective pre-weed emergence control of graminaceous weeds such as barnyard grass, crabgrass, yellow foxtail and Johnson grass in a crop area which comprises applying to the crop area a compound of the general formula II at an application rate sufficient to control the weeds but substantially non-phytotoxic to the group.

COMPOUNDS OF FORMULA III

According to one feature of the present invention there are provided new compounds of the general formula III, in which $R^1$ is alkyl containing 1 or 2 carbon atoms, allyl, 2-methylallyl, prop-2-ynyl, alkoxyalkyl containing 2–4 carbon atoms, haloalkyl containing 1–4 carbon atoms, 2-haloallyl, 2,3-dihaloallyl or cyclopropyl, $R^2$ is alkyl containing 2–8 carbon atoms, alkenyl containing 2–8 carbon atoms, alkenyloxyalkyl containing 4–8 carbon atoms (for example allyloxyalkyl or (2-methylallyloxyalkyl)) haloalkyl containing 2–8 carbon atoms, 2-haloallyl, 2,3-dihaloallyl, cyclopropyl or cyclohexyl, $R^3$ is alkyl containing 1–4 carbon atoms, allyl, 2-methylallyl, prop-2-ynyl, alkoxyalkyl containing 2–4 carbon atoms, haloalkyl containing 1–4 carbon atoms, 2-haloallyl, 2,3-dihaloallyl, cyclopropyl or phenyl containing 1–3 halo substituents, $R^4$ is alkyl containing 1–8 carbon atoms, alkenyl containing 2–8 carbon atoms, alkoxyalkyl containing 2–8 carbon atoms, alkenyloxyalkyl containing 4–8 carbon atoms (for example allyloxyalkyl or (2-methylallyl)oxyalkyl), haloalkyl containing 1–8 carbon atoms, 2-haloallyl, 2,3-dihaloallyl, cyclopropyl, or cyclohexyl, or $R^3$ and $R^4$, together with the nitrogen atom to which they are attached, form a heterocyclic ring, optionally containing 1–4 lower alkyl (preferably methyl) substituents, selected from morpholino, pyrrolidino, 1-piperidyl, hexamethyleneimino and heptamethyleneimino, provided that the total number of carbon atoms in $R^1$ and $R^2$ together is 3–9 inclusive, and when $R^3$ is a radical not containing a phenyl mucleus, the total number of carbon atoms in $R^3$ and $R^4$ together is 2–9 inclusive.

Preferably any alkoxy, alkenyloxy or halo substituent in an alkoxyalkyl, alkenyloxyalkyl or haloalkyl radical is attached in a position other than the alpha position, i.e. is attached to a carbon atom other than that which is attached to the nitrogen atom of the carbamoyl group —$CONR^1R^2$ or the nitrogen atom of the sulphamoyl group —$SO_2NR^3R^4$. Under these circumstances, when $R^4$ is alkoxyalkyl it contains 3–8 carbon atoms, when $R^2$ or $R^4$ is alkenyloxyalkyl it contains 5–8 carbon atoms and when $R^2$ or $R^4$ is haloalkyl it contains 2–8 carbon atoms.

The term "halo" includes chloro, bromo and fluoro and, in the case of an aliphatic group, is preferably chloro. The term "alkoxy" includes alkoxy radicals with 1, 2, 3 or 4 carbon atoms, for example methoxy, ethoxy, propoxy, isopropoxy, n-butoxy and isobutoxy. The term "lower" designates an alkyl or alkoxy radical with 1 – 3 carbon atoms, preferably methoxy or methyl. A preferred value of "alkenyloxyalkyl" is allyloxyalkyl, for example allyloxyethyl or 3-allyloxypropyl. Preferred values of alkenyl for $R^2$ and $R^4$ are allyl and 2-methylallyl.

The radicals $R^1$ and $R^2$ may be straight or branched chain radicals.

Typical values of $R^1$ include, for example, methyl, ethyl, allyl, 2-methylallyl, prop-2-ynyl, methoxymethyl, 2-methoxyethyl, 2-ethoxyethyl, 3-methoxypropyl, chloromethyl, 2-chloroethyl, 2-bromoethyl, 2-fluoroethyl, 3-chloropropyl, 3-bromopropyl, 4-chlorobutyl, 4-bromobutyl, 2-chloroallyl, 2-bromoallyl, 2,3-dichloroallyl, 2,3-dibromoallyl and cyclopropyl.

Typical values of $R^2$ include, for example, ethyl, propyl, isopropyl, n-butyl, isobutyl, sec.butyl, n-pentyl, isopentyl, n-hexyl, n-heptyl, n-octyl, allyl, 2-methylallyl, 2-allyloxyethyl, 3-allyloxypropyl, 2-chloroethyl, 2-bromoethyl, 2-fluoroethyl, 3-chloropropyl, 3-bromopropyl, 4-chlorobutyl, 4-bromobutyl, 3-chloropentyl, 6-chlorohexyl, 2-chloroallyl, 2-bromoallyl, 2,3-dichloroallyl, 2,3-dibromoallyl, cyclopropyl, and cyclohexyl.

Typical values of the carbamoyl group —$CONR^1R^2$ include dialkylcarbamoyl [for example N-methyl-N-ethylcarbamoyl, diethylcarbamoyl, N-ethyl-N-propylcarbamoyl, N-ethyl-N-isopropylcarbamoyl, N-butyl-N-ethylcarbamoyl], diallylcarbamoyl, N-allyl-N-alkylcarbamoyl wherein the alkyl radical contains 1 – 6 carbon atoms [for example N-allyl-N-methylcarbamoyl, N-allyl-N-ethylcarbamoyl, N-allyl-N-propylcarbamoyl, N-allyl-N-n-butylcarbamoyl, N-allyl-N-isobutylcarbamoyl, N-allyl-N-n-pentylcarbamoyl and N-allyl-N-n-hexylcarbamoyl], N-allyl-N-(2-methoxyethyl)carbamoyl, N-allyl-N-(2-ethoxyethyl)carbamoyl, N-allyl-N-(2-chloroethyl)carbamoyl, N-alkyl-N-(2-methoxyethyl)-carbamoyl or N-alkyl-N-(2-ethoxyethyl)carbamoyl wherein the alkyl radical contains 2 – 6 carbon atoms [for example N-ethyl-N-(2-methoxyethyl)carbamoyl, N-propyl-N-(2-methoxyethyl)carbamoyl, N-ethyl-N-(2-ethoxyethyl)carbamoyl, and N-propyl-N-(2-ethoxyethyl)carbamoyl], N-methyl-N-cyclohexylcarbamoyl, N-propyl-N-prop-2-ynyl, N-alkyl-N-(2-chloroallyl)carbamoyl wherein the alkyl radical contains 2 – 6 carbon atoms and N-alkyl-N-(2,3-dichloroallyl)carbamoyl wherein the alkyl radical contains 2 – 6 carbon atoms, N-cyclopropyl-N-propylcarbamoyl, and N-cyclopropyl-N-ethylcarbamoyl.

The radicals $R^3$ and $R^4$ may be straight or branched chain radicals.

Typical values of $R^3$ include, for example, methyl, ethyl, propyl, isopropyl, n-butyl, isobutyl, sec.butyl, allyl, 2-methylallyl, prop-2-ynyl, methoxymethyl, 2-methoxyethyl, 2-ethoxyethyl, 3-methoxypropyl, chloromethyl, 2-chloroethyl, 2-bromoethyl, 2-fluoroethyl, 3-chloropropyl, 3-bromopropyl, 4-chlorobutyl, 4-bromobutyl, 2-chloroallyl, 2-bromoallyl, 2,3-dichloroallyl, 2,3-dibromoallyl, cyclopropyl, 4-chlorophenyl, 4-bromophenyl and 4-fluorophenyl.

Typical values of $R^4$ include, for example, methyl, ethyl, propyl, isopropyl, n-butyl, isobutyl, sec.butyl, n-pentyl, isopentyl, n-hexyl, n-heptyl, n-octyl, allyl, 2-methylallyl, methoxymethyl, 2-methoxyethyl, 2-ethoxyethyl, 2-propoxyethyl, 2-n-butoxyethyl, 3-methoxypropyl, 3-ethoxypropyl, 2-methoxypropyl, 2-ethoxypropyl, 2-n-butoxyethyl, 2-chloroethyl, 2-bromoethyl, 2-fluoroethyl, 3-chloropropyl, 3-bromopropyl, 4-chlorobutyl, 4-bromobutyl, 3-chloropentyl, 6-chlorohexyl, 2-chloroallyl, 2-bromoallyl, 2,3-dichloroallyl, 2,3-dibromoallyl, cyclopropyl, cyclohexyl, 2-allyloxyethyl and 3-allyloxypropyl.

As hereinbefore mentioned, when the group $NR^3R^4$ is a heterocyclic group, it may contain 1 – 4 lower alkyl (preferably methyl) substituents. Such alkyl-substituted heterocyclic groups include, for example, 2,6-dimethylmorpholino, 4-methyl-1-piperidyl, 2-methyl-1-piperidyl and 2,6-dimethyl-1-piperidyl.

Typical examples of the sulphamoyl group —$SO_2NR^3R^4$ include, for example, dimethylsulphamoyl, diethylsulphamoyl, dipropylsulphamoyl, di-n-butylsulphamoyl, diallylsulphamoyl, di-(2-methylallyl)-sulphamoyl, N-lower alkyl-N-cyclohexylsulphamoyl for example N-methyl-N-cyclohexylsulphamoyl, N-allyl-N-alkylsulphamoyl wherein the alkyl radical contains 1 – 5 carbon atoms (for example N-allyl-N-methylsulphamoyl, N-allyl-N-ethylsulphamoyl and N-allyl-N- propylsulphamoyl), N-methyl-N-alkylsulphamoyl wherein the alkyl radical contains 1 - 8 carbon atoms (for example N-methyl-N-ethylsulphamoyl, N-methyl-N-propylsulphamoyl, N-methyl-N-n-butylsulphamoyl, N-methyl-N-sec.butylsulphamoyl and N-methyl-N-isobutylsulphamoyl), N-ethyl-N-propylsulphamoyl, N-ethyl-N-isopropylsulphamoyl, N-ethyl-N-butylsulphamoyl, N-methyl-N-(4-fluorophenyl)sulphamoyl, morpholinosulphonyl, 1-pyrrolidinylsulphonyl, 1-piperidylsulphonyl, hexamethyleneiminosulphonyl and heptamethyleneiminosulphonyl.

Preferably, $R^1$ is alkyl containing 1 or 2 carbon atoms, allyl, 2-methylallyl, prop-2-ynyl, or alkoxyalkyl containing 2 - 4 carbon atoms and $R^2$ is alkyl containing 2 - 8 carbon atoms, allyl or 2-methylallyl. It is preferred that the carbamoyl group $CONR^1 R^2$ is dialkylcarbamoyl in which the alkyl groups are the same or different and together contain 3 - 6 carbon atoms, diallylcarbamoyl, N-allyl-N-alkylcarbamoyl in which the alkyl group contains 1 - 4 carbon atoms, or N-alkyl-N-alkoxyalkylcarbamoyl in which the alkyl group contains 2 to 4 carbon atoms and the alkoxyalkyl group contains 3 or 4 carbon atoms.

Preferably, $R^3$ is alkyl containing 1 - 4 carbon atoms, allyl, 2-methylallyl, alkoxyalkyl containing 3 or 4 carbon atoms, phenyl containing a single halosubstituent and $R^4$ is alkyl containing 1 - 8 carbon atoms, allyl, methylallyl or alkoxyalkyl containing 3 - 8 carbon atoms. It is preferred that the sulphamoyl group is dialkylsulphamoyl in which the alkyl groups are the same or different and each contain 1 - 4 carbon atoms, diallylsulphamoyl, di-(2-methylallyl)sulphamoyl, or N-allyl-N-alkylsulphamoyl in which the alkyl group contains 1 - 4 carbon atoms. Expecially suitable compounds of formula II are those in which:

a. the carbamoyl group is diallylcarbamoyl and the sulphamoyl group is dialkylsulphamoyl, di(2-methylallyl)sulphamoyl or N-allyl-N-alkylsulphamoyl, b. the carbamoyl group is dialkylcarbamoyl and the sulphamoyl group is dialkylsulphamoyl, diallylsulphamoyl or N-allyl-N-alkylsulphamoyl, c. the carbamoyl group is N-allyl-N-alkylcarbamoyl and the sulphamoyl group is dialkylsulphamoyl diallylsulphamoyl or N-allyl-N-alkylsulphamoyl, d. the carbamoyl group is N-alkyl-N-alkoxyalkylcarbamoyl and the sulphamoyl group is dialkylsulphamoyl, diallylsulphamoyl or N-allyl-N-alkylsulphamoyl.

The present invention also provides herbicidal compositions which comprise as an active ingredient a compound of the general formula III in association with a diluent or carrier. The diluent or carrier may be a solid or liquid, optionally in association with a surface-active agent, for example a dispersing agent, emulsifying agent or wetting agent.

According to a further feature of the present invention there is provided a method for the pre-weed emergence control of graminaceous weeds which comprises applying to the locus of the weeds, for example the soil, a compound of the general formula III. A particular embodiment of this feature is a method for the selective pre-weed emergence control of graminaceous weeds such as barnyard grass, crabgrass, yellow foxtail and Johnson grass in a crop area which comprises applying to the crop area a compound of the general formula III at an application rate sufficient to control the weeds but substantially non-phytotoxic to the crop.

We have found that the triazole compounds of formulae I, II and III have valuable herbicidal properties against graminaceous weeds. For example, the compounds possess a high level of pre-weed emergence herbicidal activity against the graminaceous weeds crabgrass (*Digitaria sanguinalis*), barnyard grass (*Echinochloa crusgalli*), yellow foxtail (*Setaria lutescens*) and Johnson grass (*Sorghum halepense*). Furthermore, detailed trials in the glasshouse have shown that the compounds give a pre-weed emergence control of each of these weeds at application rates that cause no significant phytotoxic effect on the crops cotton, soyabean, peanut and maize when the compounds are applied prior to the emergence of these crops. Accordingly the compounds of the present invention can be used for the selective pre-emergence control of all of these weeds in these crops. This is an important advantage, since crabgrass, barnyard grass, yellow foxtail and Johnson grass are all important weeds in cotton, soyabean, peanut and maize and often occur together in these crops.

We have found that the compounds of the present invention have superior herbicidal properties to a variety of closely related 1,2,4-triazoles within the hereinbefore defined broad group of compounds described in U.S. Pat. No. 3,308,131, including a representative selection of the compounds specifically exemplified in that patent specification. Detailed trials in the glasshouse have demonstrated that, in contrast to the compounds of the present invention, these closely related compounds do not possess both the above-described high level of pre-weed emergence herbicidal activity and the above-described ability to control selectively all four of the weeds crabgrass, barnyard grass, yellow foxtail and Johnson grass in cotton, soyabean, peanut and maize.

The compositions of the present invention include not only compositions in a suitable form for application but also concentrated primary compositions which may be supplied to the user and which require dilution with a suitable quantity of water or other diluent before application.

Typical compositions falling within the present invention include the following:

a. Dispersions and dispersible preparations

As dispersions, the compositions comprise essentially a triazole compound of the general formula I, II or III dispersed in an aqueous medium. It is convenient to supply the consumer with a primary composition which may be diluted with water to form a dispersion having the desired concentration; the primary composition may be in any one of the following forms. It may be provided as a dispersible solution which comprises a compound of the general formula I, II or III dissolved in a water-miscible solvent with the addition of a dispersing agent. Alternatively it may be provided as a dispersible powder which comprises a compound of the general formula I, II or III and a dispersing agent. A further alternative comprises a compound of the general formula I, II or III in the form of a finely ground powder in association with a dispersing agent and intimately mixed with water to give a paste or cream. This paste or cream may if desired be added to an emulsion of oil in water to give a dispersion of active ingredient in an aqueous oil emulsion.

b. Emulsions and emulsifiable preparations

Emulsions comprise essentially a triazole compound of the general formula I, II or III dissolved in water-immiscible solvent which is formed into an emulsion with water in the presence of an emulsifying agent. An emulsion of the desired concentration may be formed from a primary composition of the following types. A concentrated stock emulsion may be supplied comprising a compound of the general formula I, II or III in combination with an emulsifying agent, water and a water-immiscible solvent. Alternatively there may be supplied an emulsifiable concentrate comprising a solution of a compound of the general formula I, II or III in a water-immiscible solvent containing an emulsifying agent.

c. Dusting powders

A dusting powder comprises a triazole compound of the general formula I, II or III intimately mixed and ground with a solid pulverulent diluent, for example kaolin.

d. Granular solids

These may comprise a compound of the general formula I, II or III associated with similar diluents to those which may be employed in dusting powders, but the mixture is granulated by known methods. Alternatively they may comprise the active ingredient absorbed or adsorbed on a pre-formed granular diluent for example fullers earth, attapulgite and limestone grit.

In addition to the ingredients already mentioned, the compositions of the invention may also contain other substances conventionally used in the art, the function of which may be to improve the ease of handling of the compositions or to improve their utility. For example an inert diluent such as kaolin may be included in dispersible powders in order to facilitate grinding and to provide sufficient bulk for mixing with water. As a further example, the compositions intended for dilution with water prior to application may also contain a wetting agent in order to obtain rapid wetting-out of the materials and to ensure satisfactory coverage of the soil. Also when dusts are prepared, a lubricant such as magnesium stearate may be added to the mixture to promote both easier mixing of the components and to ensure that the final product has free-flowing properties.

The compositions hereinbefore described wherein the active ingredients are present in solid form, for example dusting powders and dispersible powders, should preferably contain the compound of the general formula I, II or III in the form of very fine particles; the majority of the particles, of the order of at least 95%, should be less than $50\mu$, with about 75% of them being $5 - 20\mu$. The adjuvants conventionally used in such compositions are generally of this particle size or smaller. The compositions can be prepared by means of conventional grinding equipment such as a hammer mill.

The concentration of compound of the general formula I, II or III in the primary compositions which may be provided for the preparation of any of the forms in which the compositions of the invention may be used may vary widely and may be, for example, 2 – 95% w/w of the composition. It will be appreciated that this concentration will be influenced by the nature of the primary composition and the physical properties of its ingredients.

The concentration of the compound of general formula I, II or III in the compositions for application to control weeds should be at least 0.001% w/w, preferably 0.05 – 10% w/w.

In addition to a compound of the general formula I, II or III, the compositions of the present invention may contain one or more additional active ingredients, for example one or more insecticides, nematocides, or additional herbicides. Such an additional herbicide may be, for example, a substituted urea, for example diuron or monuron; a triazine, for example simazine or atrazine; a substituted acetanilide, for example propachlor; a nitrophenyl ether, for example nitrofen; a carbamate, for example chlorpropham; or a thiolcarbamate, for example EPTC or tri-allate.

The invention includes a method for the pre-weed emergence control of graminaceous weeds which comprises applying to the locus of the weeds, for example the soil, a triazole compound of the formula I, II or III. This method may be used subsequent to the emergence of the crop, for example for the pre-weed emergence control of graminaceous weeds such as barnyard grass in seeded or transplanted rice, but is often used prior to the emergence of the crop, as is usually the case with the control of crabgrass, barnyard grass, yellow foxtail and Johnson grass in cotton, soyabean, peanut and maize. When the method is used prior to the emergence of the crop, it is convenient to apply the compounds of the invention to the soil in which the crop is sown at or just prior to the time of sowing. Thus, for example, the compounds of the invention may be incorporated into the top layer of soil as part of a sowing procedure.

For the control of graminaceous weeds, the compounds of the invention are generally used at an application rate of 0.05 – 50 lb./acre, preferably 0.1 – 20 lb./acre. Selective pre-weed emergence control of weeds may be achieved in many instances at an application rate within the range 0.1 – 10 lb./acre.

The selective pre-weed emergence herbicidal activity of the compounds of the present invention is demonstrated by the results obtained in detailed trials carried out in the glasshouse. In these trials, trays of soil were sown with seeds of various weeds and crops, and then immediately sprayed with aqueous suspensions of the compounds under test at logarithmically reducing application rates of test compound within the range 8 1/32 lb./acre. Seeded trays of soil receiving no chemical treatment were used as controls. The weeds used were crabgrass (CG), barnyard grass (BG), yellow foxtail (YF) and Johnson grass (JG). The crops used were cotton (CO), soyabean (SB), maize (M) and peanut (P).

In the case of the weeds, the minimum application rate was recorded at which control of the weeds was achieved, as shown by emergent seedlings that were severely and irrecoverably stunted. In the case of the crops, the minimum application rate was recorded at which a phytotoxic effect was observed on the emergent seedlings. In some cases no phytotoxic effect on a crop was observed at the maximum application rate of test compound of 8 lb./acre, and this result was recorded as ">8". The results obtained with various compounds within the general formulae I, II and III are shown in the following Tables. In these Tables, the following abbreviations are used:

Me = methyl, Et = ethyl, Pr = propyl, Bu = butyl, Pen = pentyl, Hex = hexyl, $i$ = iso and $s$ = secondary. Alkyl radicals without the designation i- or s- signify normal radicals.

Table 1

| Compound (I) | | Minimum rate (lb./acre) | | | | | | | |
|---|---|---|---|---|---|---|---|---|---|
| | | control | | | | | phytotoxicity | | |
| R³ | NR¹R² | CG | BG | YF | JG | CO | SB | M | P |
| SEt | N(allyl)₂ | 1/8 | 1/4 | 1/4 | 1/4 | >8 | 4 | 2 | >8 |
| SPr | " | 1/8 | 1/2 | 1/4 | 1/4 | >8 | >8 | 2 | 2 |
| Si-Pr | " | 1/16 | 1/8 | 1/4 | 1/16 | >8 | >8 | 2 | 4 |
| SBu | " | 1/4 | 1/2 | 1/2 | 1/2 | 4 | >8 | >8 | >8 |
| Si-Bu | " | 1/8 | 1/4 | 1/2 | 1/4 | >8 | >8 | 4 | >8 |
| Ss-Bu | " | 1/8 | 1/2 | 1/8 | 1/8 | >8 | >8 | 2 | 4 |
| SPen | " | 1/4 | 1/4 | 1/2 | 1/2 | >8 | >8 | >8 | >8 |
| SOPr | " | 1/16 | 1/4 | 1/16 | 1/8 | >8 | >8 | 4 | >8 |
| SOi-Pr | " | 1/4 | 1/4 | 1/2 | 1/4 | 4 | >8 | 2 | >8 |
| SOBu | " | 1/32 | 1/8 | 1/8 | 1/16 | >8 | >8 | 4 | >8 |
| SOi-Bu | " | 1/8 | 1/8 | 1/4 | 1/8 | 2 | 1 | 1 | 4 |
| SOs-Bu | N(allyl)₂ | 1/8 | 1/4 | 1/8 | 1/16 | 2 | >8 | 4 | 4 |
| SOPen | " | 1/8 | 1/16 | 1/16 | 1/16 | >8 | >8 | 2 | >8 |
| SO₂Me | " | 1/2 | 1/2 | 1/2 | 1/8 | 2 | >8 | 2 | >8 |
| SO₂Et | " | 1/16 | 1/4 | 1/16 | 1/8 | >8 | >8 | >8 | 4 |
| SO₂Pr | " | 1/16 | 1/8 | 1/16 | 1/8 | >8 | >8 | 4 | 1 |
| SO₂i-Pr | " | 1/16 | 1/16 | 1/4 | 1/16 | 2 | 4 | 2 | 4 |
| SO₂Bu | " | 1/8 | 1/4 | 1/4 | 1/16 | >8 | >8 | >8 | >8 |
| SO₂i-Bu | " | 1/16 | 1/16 | 1/8 | 1/16 | 4 | 4 | 2 | 4 |
| SO₂s-Bu | " | 1/16 | 1/16 | 1/8 | 1/16 | 2 | 1 | 1 | 4 |
| SO₂Pen | " | 1/4 | 1/4 | 1/4 | 1/16 | 4 | >8 | >8 | >8 |
| Sallyl | " | 1/4 | 1/2 | 1/4 | 1/4 | >8 | 4 | 2 | >8 |
| Sbut-2-enyl | " | 1/16 | 1 | 1/2 | 1/2 | >8 | >8 | >8 | >8 |
| SEt | N(2-Me-allyl)₂ | 1/4 | 1 | 1/2 | 1/4 | >8 | 4 | 4 | >8 |
| SO₂Et | " | 1/4 | 1/2 | 1/4 | 1/4 | 4 | >8 | 4 | >8 |
| SEt | NPr₂ | 1/4 | 1 | 1/4 | 1/4 | >8 | 4 | 4 | >8 |
| SPr | " | 1/4 | 1 | 1 | 1 | >8 | >8 | >8 | >8 |
| SBu | " | 1/2 | 1 | 1 | 1 | >8 | 4 | >8 | >8 |
| Si-Bu | " | 1/4 | 1 | 1 | 1 | >8 | 4 | >8 | >8 |
| Ss-Bu | " | 1/4 | 1 | 1 | 1 | >8 | >8 | >8 | >8 |
| SPen | " 1/4 | 1/2 | 1 | 1 | >8 | >8 | >8 | >8 | |
| SOPr | " | 1/4 | 1 | 1/4 | 1/4 | >8 | >8 | 4 | >8 |
| SOi-Pr | " | 1/4 | 1 | 1 | 1 | 4 | >8 | 4 | 4 |
| SOBu | " | 1/4 | 1/4 | 1/4 | 1/4 | >8 | 4 | 2 | 4 |
| SOi-Bu | " | 1/2 | 1/2 | 1/2 | 1/2 | >8 | >8 | 4 | >8 |
| SOs-Bu | " | 1/4 | 1/4 | 1/4 | 1/2 | 2 | 4 | 4 | 2 |
| SOPen | " | 1/4 | 1/8 | 1/4 | 1/16 | >8 | >8 | >8 | >8 |
| SO₂Me | " | 1/8 | 1/2 | 1/4 | 1/2 | 4 | 4 | 4 | >8 |
| SO₂Et | " | 1/32 | 1/16 | 1/8 | 1/32 | >8 | >8 | >8 | 4 |
| SO₂Pr | " | 1/32 | 1/32 | 1/16 | 1/16 | >8 | >8 | >8 | >8 |
| SO₂i-Pr | NPr₂ | 1/4 | 1/4 | 1/8 | 1/4 | >8 | >8 | 4 | >8 |
| SO₂Bu | " | 1/32 | 1/16 | 1/16 | 1/16 | >8 | >8 | >8 | >8 |
| SO₂i-Bu | " | 1/16 | 1/8 | 1/8 | 1/16 | 4 | 4 | 2 | >8 |
| SO₂s-Bu | " | 1/16 | 1/16 | 1/16 | 1/4 | >8 | 4 | 2 | >8 |
| SO₂Pen | " | 1/4 | 1/4 | 1/4 | 1/4 | 4 | >8 | 4 | 4 |
| Sallyl | " | 1/2 | 1 | 1/2 | 1/4 | >8 | 4 | 4 | >8 |
| Sbut-2-enyl | " | 1/2 | 1 | 1 | 1 | >8 | >8 | >8 | >8 |
| SO₂Et | N(Pr)i-Pr | 1/16 | 1/8 | 1/16 | 1/8 | 2 | 2 | 1 | >8 |
| SEt | NEt₂ | 1/4 | 1/16 | 1/4 | 1/16 | 4 | 2 | 1 | >8 |
| SPr | " | 1/4 | 1 | 1/2 | 1/8 | >8 | >8 | 4 | >8 |
| Si-Pr | " | 1/16 | 1/4 | 1/4 | 1/16 | >8 | 2 | 1 | >8 |
| SBu | " | 1 | 1 | 1/2 | 1/2 | >8 | 4 | 2 | >8 |
| Si-Bu | " | 1/16 | 1/4 | 1/16 | 1/16 | >8 | 2 | 2 | >8 |
| Ss-Bu | " | 1/4 | 1/4 | 1/2 | 1/16 | >8 | 4 | 2 | >8 |
| SPen | " | 1/16 | 1/2 | 1/4 | 1/8 | >8 | >8 | >8 | >8 |
| SOPr | " | 1/4 | 1/4 | 1/4 | 1/4 | 4 | 2 | 1 | >8 |
| SOi-Pr | NEt₂ | 1 | 1 | 1 | 1/2 | >8 | >8 | >8 | 4 |
| SOBu | " | 1/8 | 1/4 | 1/32 | 1/2 | 2 | >8 | 2 | >8 |
| SO₂Me | " | 1/8 | 1/8 | 1/4 | 1/8 | 4 | 1 | 2 | >8 |
| SO₂Et | " | 1/8 | 1/4 | 1/8 | 1/8 | 4 | 4 | 1 | 4 |
| SO₂Pr | " | 1/8 | 1/4 | 1/4 | 1/16 | 1 | 4 | 1 | >8 |
| SO₂i-Pr | " | 1/16 | 1/8 | 1/16 | 1/16 | 1 | 1 | 1 | >8 |
| SO₂Bu | " | 1/16 | 1/8 | 1/16 | 1/16 | 2 | 4 | 1 | 4 |
| SO₂i-Bu | " | 1/16 | 1/16 | 1/16 | 1/16 | 2 | 1 | 1/2 | 2 |
| SO₂Pen | " | 1/16 | 1/16 | 1/4 | 1/4 | 1 | 1 | 1 | 2 |
| SEt | N—Pr<br>\|<br>prop—2—ynyl | 1/16 | 1/8 | 1/8 | 1/16 | >8 | >8 | 4 | 2 |
| SO₂Et | " | 1/4 | 1/4 | 1/4 | 1/8 | >8 | >8 | >8 | >8 |
| Sallyl | " | 1/16 | 1/2 | 1/8 | 1/4 | 4 | 2 | 2 | >8 |
| SEt | N(allyl)Et | 1/4 | 1/4 | 1 | 1/2 | >8 | 4 | 4 | >8 |
| SEt | N(allyl)Pr | 1/4 | 1/4 | 1/4 | 1/2 | >8 | >8 | 2 | 2 |
| SEt | N(allyl)Bu | 1/4 | 1/4 | 1/4 | 1/4 | >8 | >8 | >8 | 1 |
| SEt | N(allyl)Pen | 1/8 | 1/2 | 1/4 | 1/16 | >8 | >8 | 4 | 2 |
| SEt | N(allyl)Hex | 1/4 | 1/2 | 1/2 | 1/4 | >8 | 4 | 2 | >8 |
| SEt | N(allyl)i-Bu | 1/16 | 1/2 | 1/16 | 1/8 | >8 | >8 | 2 | >8 |
| SO₂Et | N(allyl)Et | 1/16 | 1/16 | 1/4 | 1/16 | >8 | >8 | 2 | >8 |
| SO₂Et | N(allyl)Pr | 1/8 | 1/4 | 1/4 | 1/4 | 4 | 4 | 2 | >8 |
| SO₂Et | N(allyl)Bu | 1/4 | 1/4 | 1/4 | 1/4 | 4 | 4 | 2 | >8 |
| SO₂Et | N(allyl)Pen | 1/16 | 1/8 | 1/8 | 1/8 | 4 | 2 | 2 | 4 |
| SO₂Et | N(allyl)Hex | 1/8 | 1/8 | 1/8 | 1/8 | >8 | >8 | 1 | >8 |
| SO₂Et | N(allyl)i-Bu | 1/16 | 1/16 | 1/16 | 1/16 | >8 | >8 | >8 | >8 |
| SEt | N(Et)Pr | 1/2 | 1 | 1 | 1 | >8 | 4 | 2 | >8 |
| SEt | N(Et)Bu | 1/2 | 1 | 1 | 1 | >8 | 4 | 4 | >8 |
| SEt | N(Et)Pen | 1/2 | 1/4 | 1 | 1 | >8 | >8 | 4 | 4 |
| SEt | N(Et)Hex | 1/2 | 1/2 | 1/2 | 1/4 | >8 | >8 | 4 | >8 |
| SEt | N(Pr)Bu | 1/2 | 1 | 1 | 1 | 1/2 | >8 | >8 | >8 | >8 |
| SEt | N(Pr)Pen | 1/4 | 1/2 | 1 | 1/4 | >8 | >8 | 4 | >8 |
| SEt | N(Et)i-Bu | 1/16 | 1 | 1/16 | 1/2 | >8 | >8 | 4 | >8 |

Table 1-continued

| Compound (I) | | Minimum rate (lb./acre) control | | | | | | Phytotoxicity | |
|---|---|---|---|---|---|---|---|---|---|
| $R^3$ | $NR^1R^2$ | CG | BG | YF | JG | CO | SB | M | P |
| SEt | N(Et)i-Pen | 1/2 | 1 | 1 | 1/16 | >8 | >8 | 4 | 4 |
| SEt | N(Pr)i-Bu | 1/2 | 1 | 1 | 1 | >8 | >8 | >8 | >8 |
| $SO_2Et$ | N(Et)Pr | 1/16 | 1/4 | 1/4 | 1/8 | >8 | 1 | 1 | >8 |
| $SO_2Et$ | N(Et)Bu | 1/8 | 1/8 | 1/4 | 1/16 | >8 | >8 | 4 | 4 |
| SOi-Bu | $NEt_2$ | 1/16 | 1/4 | 1/4 | 1/16 | 4 | 2 | 1 | >8 |
| $SO_2$s-Bu | $NEt_2$ | 1/16 | 1/16 | 1/16 | 1/16 | 2 | 1 | 1/4 | 4 |
| $SO_2$t-Bu | $NEt_2$ | 1/4 | 1/2 | 1/8 | 1/16 | >8 | >8 | >8 | >8 |
| $SO_2Et$ | $N(i-Pr)_2$ | 1/8 | 1/2 | 1 | 1 | 4 | 4 | 4 | >8 |
| $SO_2$s-Bu | $N(i-Pr)_2$ | 1/16 | 1/16 | 1/16 | 1/16 | 4 | >8 | 4 | >8 |
| $SO_2Me$ | $NBu_2$ | 1/4 | 1/2 | 1 | 1/4 | >8 | 4 | 4 | >8 |
| $SO_2Bu$ | $NBu_2$ | 1/4 | 1/4 | 1/4 | 1/2 | >8 | 4 | 4 | >8 |
| Sallyl | $N(allyl)_2$ | 1/4 | 1/2 | 1/4 | 1/4 | >8 | 4 | 2 | >8 |
| Sbut-2-enyl | $N(allyl)_2$ | 1/16 | 1 | 1/2 | 1/2 | >8 | >8 | >8 | >8 |
| $SO_2$t-Bu | $N(allyl)_2$ | 1/2 | 1/2 | 1/4 | 1/4 | >8 | >8 | 4 | >8 |
| $SO_2$s-Bu | $N(2-Me-allyl)_2$ | 1/8 | 1/16 | 1/8 | 1/8 | >8 | >8 | 2 | >8 |
| SEt | N(i-Bu)Et | 1/16 | 1 | 1/16 | 1/2 | >8 | >8 | 4 | >8 |
| SEt | N(s-Bu)Pr | 1/4 | 1/2 | 1/8 | 1/4 | >8 | >8 | >8 | >8 |
| $SO_2$i-Pr | N(Et)Pr | 1/32 | 1/16 | 1/32 | 1/16 | >8 | >8 | 2 | >8 |
| $SO_2Bu$ | N(Et)Pr | 1/32 | 1/32 | 1/32 | 1/32 | >8 | 4 | 1/2 | 4 |
| $SO_2$i-Bu | N(Et)Pr | 1/32 | 1/32 | 1/32 | 1/32 | 4 | 4 | 1 | 4 |
| $SO_2Pr$ | N(i-Pr)Et | 1/32 | 1/32 | 1/16 | 1/16 | 4 | 2 | 1/4 | >8 |
| $SO_2Bu$ | N(i-Pr)Et | 1/32 | 1/32 | 1/32 | 1/32 | 4 | 4 | 2 | 4 |
| $SO_2$i-Bu | N(i-Pr)Et | 1/32 | 1/32 | 1/32 | 1/32 | 2 | 2 | 1/4 | 4 |
| $SO_2Et$ | N(i-Bu)Et | 1/16 | 1/8 | 1/16 | 1/8 | >8 | >8 | 2 | >8 |
| $SO_2Pr$ | N(i-Bu)Et | 1/32 | 1/32 | 1/32 | 1/32 | 2 | 2 | 1/2 | 4 |
| $SO_2Bu$ | N(i-Bu)Et | 1/32 | 1/32 | 1/32 | 1/32 | 4 | >8 | 1/4 | >8 |
| $SO_2$t-Bu | N(Et)Bu | 1 | 1/2 | 1 | 1/4 | >8 | >8 | >8 | >8 |
| $SO_2Pr$ | N(i-Pen)Et | 1/16 | 1/16 | 1/16 | 1/16 | >8 | >8 | 1 | >8 |
| $SO_2Bu$ | N(i-Pen)Et | 1/16 | 1/16 | 1/16 | 1/16 | >8 | >8 | 4 | >8 |
| $SO_2$i-Bu | N(i-Pen)Et | 1/32 | 1/32 | 1/32 | 1/32 | >8 | 4 | 1 | >8 |
| $SO_2Pr$ | N(Hex)Et | 1/16 | 1/16 | 1/16 | 1/16 | >8 | >8 | 4 | 4 |
| $SO_2$i-Pr | N(Hex)Et | 1/16 | 1/16 | 1/8 | 1/16 | >8 | >8 | 1 | >8 |
| $SO_2Pr$ | N(i-Pr)Pr | 1/16 | 1/32 | 1/16 | 1/16 | >8 | 4 | 1 | >8 |
| $SO_2Bu$ | N(i-Pr)Pr | 1/16 | 1/32 | 1/32 | 1/32 | 4 | 4 | 1/4 | 4 |
| $SO_2$t-Bu | N(allyl)Et | 1/16 | 1/8 | 1/8 | 1/4 | >8 | >8 | >8 | >8 |
| $SO_2Pr$ | N(allyl)Et | 1/16 | 1/16 | 1/16 | 1/16 | 2 | >8 | 1/2 | >8 |
| $SO_2Pr$ | N(allyl)Pr | 1/16 | 1/16 | 1/4 | 1/4 | >8 | >8 | 1 | >8 |
| $SO_2Pr$ | N(allyl)i-Pr | 1/16 | 1/16 | 1/32 | 1/8 | 2 | 4 | 1 | 4 |
| $SO_2Pr$ | N(allyl)i-Bu | 1/16 | 1/16 | 1/32 | 1/32 | 2 | 2 | 4 | 4 |
| $SO_2$i-Pr | N(allyl)Et | 1/16 | 1/16 | 1/16 | 1/16 | >8 | >8 | 4 | >8 |
| $SO_2$i-Pr | N(allyl)Pr | 1/16 | 1/16 | 1/4 | 1/4 | >8 | >8 | >8 | >8 |
| $SO_2$i-Pr | N(allyl)i-Pr | 1/16 | 1/16 | 1/16 | 1/16 | 2 | >8 | 2 | >8 |
| $SO_2Bu$ | N(allyl)Et | 1/16 | 1/16 | 1/16 | 1/16 | >8 | >8 | 1/4 | >8 |
| $SO_2Bu$ | N(allyl)Bu | 1/16 | 1/8 | 1/16 | 1/16 | >8 | >8 | >8 | >8 |
| $SO_2Bu$ | N(allyl)Hex | 1/16 | 1/2 | 1/4 | 1/4 | >8 | >8 | >8 | >8 |
| $SO_2Bu$ | N(allyl)Pr | 1/16 | 1/16 | 1/16 | 1/16 | 4 | >8 | 1 | >8 |
| $SO_2$i-Bu | N(allyl)Pr | 1/32 | 1/32 | 1/32 | 1/32 | >8 | >8 | 1 | >8 |
| $SO_2$i-Bu | N(allyl)i-Pr | 1/16 | 1/16 | 1/16 | 1/4 | 1 | 2 | 1 | >8 |
| $SO_2$i-Bu | N(allyl)Hex | 1/16 | 1/2 | 1/4 | 1/2 | >8 | >8 | 4 | >8 |
| $SO_2$s-Bu | N(allyl)Et | 1/32 | 1/32 | 1/32 | 1/32 | 4 | >8 | 1/4 | >8 |
| $SO_2$t-Bu | N(allyl)Pr | 1 | 1 | 1/2 | 1 | 4 | >8 | 4 | >8 |
| $SO_2Pr$ | N(Pr)(Prop-2-ynyl) | 1 | 1/16 | 1 | 1 | >8 | >8 | >8 | >8 |
| $SO_2$i-Pr | " | 1/16 | 1/4 | 1/4 | 1/4 | >8 | >8 | 4 | 2 |
| $SO_2$s-Bu | " | 1/16 | 1/32 | 1/8 | 1/32 | 4 | >8 | >8 | >8 |
| $SO_2Et$ | N(Et)Hex | 1/16 | 1/4 | 1/2 | 1/2 | >8 | >8 | >8 | >8 |
| $SO_2Et$ | N(Et)i-Pen | 1/16 | 1/16 | 1/16 | 1/16 | 4 | 4 | 1 | >8 |
| $SO_2Et$ | N(Pr)s-Bu | 1/16 | 1/8 | 1/16 | 1/8 | >8 | >8 | >8 | >8 |
| $SO_2Et$ | N(Pr)i-Bu | 1/8 | 1/2 | 1/4 | 1/2 | 2 | >8 | 4 | >8 |
| $SO_2Et$ | N(Pr)Pen | 1/8 | 1/4 | 1/16 | 1/8 | 4 | >8 | 1 | >8 |
| $SO_2Et$ | N(Pr)Hex | 1/4 | 1/2 | 1/2 | 1/2 | >8 | >8 | 4 | >8 |

Table 2

| Compound (II) | | Minimum rate (lb./acre) Control | | | | Phytotoxicity | | | |
|---|---|---|---|---|---|---|---|---|---|
| $R^3$ | $NR^1R^2$ | CG | BG | YF | JG | M | CO | SB | P |
| $S(CH_2)_2Oallyl$ | $NEt_2$ | 1/2 | 1/2 | 1/2 | 1/2 | >8 | >8 | >8 | >8 |
| $SO_2(CH_2)_2OEt$ | N(Et)Bu | 1/32 | 1/32 | 1/32 | 1/32 | 1/2 | 2 | 4 | >8 |
| $SO_2(CH_2)_2OEt$ | N(allyl)Et | 1/32 | 1/32 | 1/32 | 1/32 | 1/2 | 1 | 2 | >8 |
| $SO_2(CH_2)_2OEt$ | N(allyl)Pr | 1/32 | 1/32 | 1/32 | 1/32 | 1 | 1 | 2 | >8 |
| $SO_2(CH_2)_2OEt$ | N(Pr)(prop-2-ynyl) | 1/16 | 1/32 | 1/16 | 1/32 | >8 | >8 | >8 | >8 |
| $SO_2(CH_2)_2OPr$ | $NEt_2$ | 1/8 | 1/8 | 1/16 | 1/16 | 1/2 | 4 | >8 | >8 |
| $SO_2(CH_2)_3OEt$ | $NEt_2$ | 1/16 | 1/16 | 1/16 | 1/8 | 2 | 2 | 4 | 8 |
| $SO_2Et$ | $N((CH_2)_2OMe)(Et)$ | 1/16 | 1/16 | 1/8 | 1/4 | 1 | 4 | >8 | >8 |
| $SO_2$i-Pr | " | 1/4 | 1/2 | 1/2 | 1/2 | 2 | >8 | >8 | >8 |
| $SO_2Bu$ | " | 1/16 | 1/8 | 1/8 | 1/8 | 1/2 | >8 | >8 | >8 |
| $SO_2$i-Bu | " | 1/16 | 1/16 | 1/32 | 1/32 | 1/2 | 2 | 2 | >8 |
| $SO_2Et$ | $N((CH_2)_2OEt)(Et)$ | 1/16 | 1/16 | 1/32 | 1/32 | 4 | >8 | >8 | >8 |

Table 2-continued

| R³ | Compound (II) NR¹R² | CG | BG Control YF | | JG | M | Phytotoxicity CO | SB | P |
|---|---|---|---|---|---|---|---|---|---|
| SO₂Pr | N(CH₂)₂OEt / Et | 1/16 | 1/8 | 1/8 | 1/32 | 4 | >8 | >8 | 4 |
| SO₂i-Pr | " | 1/16 | 1/4 | 1/8 | 1/2 | >8 | >8 | 4 | >8 |
| SO₂Bu | " | 1/4 | 1/4 | 1/2 | 1/2 | >8 | >8 | >8 | >8 |
| SO₂Et | N(CH₂)₂OMe / Pr | 1/8 | 1/4 | 1/4 | 1/2 | 2 | >8 | >8 | >8 |
| SO₂i-Pr | " | 1/8 | 1/4 | 1/4 | 1/2 | 2 | >8 | 4 | >8 |
| SO₂Bu | " | 1/16 | 1/16 | 1/16 | 1/4 | 4 | 4 | >8 | >8 |
| SO₂i-Bu | " | 1/16 | 1/16 | 1/8 | 1/2 | 4 | >8 | >8 | >8 |
| SO₂Et | N(CH₂)₂OEt / Pr | 1/8 | 1/8 | 1/2 | 1/4 | 4 | >8 | 4 | >8 |
| SO₂Pr | " | 1/4 | 1 | 1/4 | 1/2 | >8 | >8 | >8 | >8 |
| SO₂Bu | " | 1/16 | 1/2 | 1/8 | 1/8 | 2 | >8 | >8 | >8 |
| SO₂i-Bu | " | 1/4 | 1/2 | 1/2 | 1/2 | 2 | >8 | >8 | >8 |
| SO₂Et | N(CH₂)₂OMe / Bu | 1/32 | 1/32 | 1/32 | 1/32 | >8 | >8 | >8 | >8 |
| SO₂Pr | " | 1/16 | 1/32 | 1/8 | 1/16 | 2 | >8 | >8 | >8 |
| SO₂Bu | " | 1/32 | 1/32 | 1/8 | 1/16 | 2 | >8 | >8 | >8 |
| SO₂Et | N(CH₂)₂OEt / Bu | 1 | 1/2 | 1 | 1 | 4 | >8 | >8 | >8 |
| SO₂Pr | " | 1/4 | 1/4 | 1/4 | 1/4 | >8 | >8 | >8 | >8 |
| SO₂Bu | " | 1/8 | 1/8 | 1/8 | 1/8 | >8 | >8 | >8 | >8 |
| SO₂Et | N(CH₂)₃OEt / Et | 1/16 | 1/8 | 1/8 | 1/32 | >8 | >8 | >8 | >8 |
| SO₂Et | N(CH₂)₂OMe / allyl | 1/8 | 1/32 | 1/16 | 1/8 | 2 | 4 | >8 | >8 |
| SO₂Pr | " | 1/8 | 1/4 | 1/4 | 1/4 | 1 | 2 | >8 | >8 |
| SO₂Bu | " | 1/32 | 1/32 | 1/16 | 1/32 | 1/2 | >8 | >8 | >8 |
| SO₂Et | N(CH₂)₂OEt / allyl | 1/8 | 1/4 | 1/4 | 1/8 | 2 | >8 | >8 | >8 |
| SO₂Pr | " | 1/32 | 1/8 | 1/16 | 1/4 | 2 | 4 | 4 | >8 |
| SO₂Bu | " | 1/16 | 1/16 | 1/8 | 1/16 | 1 | >8 | 4 | >8 |
| SO₂(CH₂)₂OEt | N(CH₂)₂OMe / Et | 1/32 | 1/8 | 1/8 | 1/8 | 2 | >8 | 4 | >8 |
| SO₂(CH₂)₂OEt | N(CH₂)₂OMe / Bu | 1/4 | 1/16 | 1/4 | 1/8 | 2 | >8 | 4 | >8 |
| SO₂(CH₂)₂OEt | N(CH₂)₂OMe / allyl | 1/8 | 1/32 | 1/16 | 1/16 | 2 | 4 | >8 | >8 |
| SO₂(CH₂)₂OEt | NEt₂ | 1/32 | 1/32 | 1/32 | 1/16 | 1/4 | 1 | 1 | >8 |
| SO₂(CH₂)₂OEt | N(CH₂)₂OPr / Et | 1/4 | 1/2 | 1/4 | 1/4 | 2 | >8 | 4 | >8 |
| SO₂(CH₂)₂OMe | N allyl / Et | 1/2 | 1/4 | 1/4 | 1/8 | 2 | >8 | >8 | >8 |
| SO₂(CH₂)₂OMe | N allyl / Bu | 1/8 | 1/16 | 1/4 | 1/8 | 4 | >8 | >8 | >8 |
| SO₂Et | N(CH₂)₃OEt / allyl | 1/8 | 1/8 | 1/4 | 1/4 | 2 | >8 | >8 | >8 |
| SO₂Pr | " | 1/8 | 1/8 | 1/4 | 1/4 | 2 | 4 | >8 | >8 |
| SO₂Bu | " | 1/8 | 1/4 | 1/4 | 1/8 | 1 | 4 | 4 | >8 |
| SO₂(CH₂)₂OMe | N Pr / prop-2-ynyl | 1/2 | 1/8 | 1/8 | 1/8 | >8 | >8 | >8 | >8 |
| SO₂(CH₂)₂OMe | NPr₂ | 1/8 | 1/4 | 1/16 | 1/8 | >8 | 4 | >8 | >8 |
| SO₂(CH₂)₂OMe | NEt₂ | 1/4 | 1/4 | 1/4 | 1/4 | 2 | 2 | 4 | >8 |
| SO₂(CH₂)₂OEt | NPr₂ | 1/32 | 1/16 | 1/32 | 1/32 | 4 | 2 | >8 | >8 |
| SO₂(CH₂)₂OMe | N(allyl)₂ | 1/32 | 1/16 | 1/16 | 1/32 | 4 | 2 | 2 | 4 |
| SO₂(CH₂)₂OEt | N(allyl)₂ | 1/32 | 1/16 | 1/16 | 1/32 | 1/2 | 2 | >8 | >8 |
| SO₂(CH₂)₂OMe | N Et / prop-2-ynyl | 1 | 1/8 | 1/4 | 1/4 | 4 | >8 | >8 | >8 |
| SO₂(CH₂)₂OEt | " | 1/16 | 1/2 | 1/4 | 1/4 | 4 | >8 | >8 | >8 |
| SO₂(CH₂)₂OEt | N(Pr)Hex | 1 | 1/4 | 1/4 | 1/4 | >8 | >8 | >8 | >8 |
| SO₂(CH₂)₂OMe | N(allyl)Pr | 1/8 | 1/4 | 1/8 | 1/8 | 1 | 2 | 2 | >8 |
| SO₂(CH₂)₂OMe | N Pr / prop-2-ynyl | 1/2 | 1 | 1/4 | 1/4 | >8 | 4 | 4 | >8 |
| SO₂(CH₂)₂OMe | N(i-Pr)Pr | 1/8 | 1/8 | 1/4 | 1/4 | 2 | 4 | 4 | 4 |
| SO₂(CH₂)₂OMe | N(s-Bu)Pr | 1/2 | 1/2 | 1/2 | 1 | >8 | >8 | >8 | >8 |
| SO₂(CH₂)₂OBu | N(allyl)₂ | 1/4 | 1/2 | 1/4 | 1/4 | 4 | >8 | 4 | >8 |
| SO₂(CH₂)₂OMe | N(Pr)Et | 1/8 | 1/4 | 1/4 | 1/4 | 4 | >8 | >8 | >8 |
| SO₂s-Bu | N Pr / (CH₂)₂OMe | 1/4 | 1/4 | 1/4 | 1/4 | 1 | 4 | 4 | 4 |

Table 2-continued

| Compound (II) | | Control Minimum rate (lb./acre) | | | | | Phytotoxicity | | |
|---|---|---|---|---|---|---|---|---|---|
| R³ | NR¹R² | CG | BG | YF | JG | M | CO | SB | P |
| SO₂(CH₂)₂OEt | N(allyl)Bu | 1/4 | 1/2 | 1/4 | 1/2 | 4 | >8 | >8 | >8 |
| SO₂(CH₂)₂OEt | N(s-Bu)Et | 1/4 | 1/4 | 1/4 | 1/4 | 1 | 4 | 1 | >8 |
| SO₂(CH₂)₂OEt | N(i-Pen)Et | 1/2 | 1/2 | 1/2 | 1/2 | 4 | >8 | 4 | >8 |
| SO₂(CH₂)₃OMe | N(allyl)(Pr) | 1/16 | 1/16 | 1/16 | 1/16 | 1 | 2 | 4 | >8 |
| SO₂(CH)₂Oi-Pr | N(Pr)(allyl) | 1/16 | 1/16 | 1/16 | 1/16 | 2 | 2 | 2 | >8 |
| SO₂CHMeCH₂OPr | N(Pr)(allyl) | 1/16 | 1/16 | 1/16 | 1/16 | 2 | 2 | 4 | >8 |
| SO₂(CH₂)₂Oi-Pr | N(Et)(Bu) | 1/16 | 1/16 | 1/16 | 1/16 | 1 | >8 | 4 | >8 |
| SO₂(CH₂)₂OEt | N(Et)Hex | 1/4 | 1/2 | 1/4 | 1/2 | 4 | >8 | >8 | >8 |
| SO₂CHMeCH₂OPr | N(Et)Bu | 1/16 | 1/16 | 1/16 | 1/16 | 1/2 | >8 | 2 | >8 |
| SO₂(CH₂)₂OMe | N(Pr)Et | 1/8 | 1/4 | 1/4 | 1/4 | 4 | >8 | >8 | >8 |
| SO₂(CH₂)₂OEt | N(Pr)Et | 1/4 | 1/4 | 1/4 | 1/4 | 4 | >8 | >8 | >8 |
| SO₂(CH₂)₂OMe | N(Bu)Et | 1/16 | 1/16 | 1/16 | 1/8 | 1/2 | >8 | >8 | >8 |
| SO₂(CH₂)₂OMe | N(Bu)Et | 1/8 | 1/4 | 1/16 | 1/16 | >8 | 2 | 4 | >8 |
| SO₂(CH₂)₂OEt | N(allyl)Hex | 1 | 1/2 | 1/4 | 1/4 | >8 | >8 | >8 | >8 |
| SO₂Et | N((CH₂)₂OPr)(Et) | 1/4 | 1/2 | 1/4 | 1/4 | 2 | >8 | >8 | >8 |
| SO₂Pr | N((CH₂)₂OPr)(Et) | 1/4 | 1/2 | 1/2 | 1/2 | >8 | >8 | >8 | >8 |
| SO₂s-Bu | N(Et)((CH₂)₂OEt) | 1/4 | 1/4 | 1/4 | 1/4 | 1 | 4 | 4 | 4 |
| SO₂Pent | N(Pr)((CH₂)₂OMe) | 1/4 | 1/4 | 1/4 | 1/4 | 2 | 4 | 4 | >8 |
| SO₂s-Bu | N(Pr)((CH₂)₂OEt) | 1/2 | 1/2 | 1/2 | 1/4 | 2 | >8 | 4 | >8 |
| SO₂Pr | N(Pr)(CH₂OMe) | 1/2 | 1/2 | 1/4 | 1/4 | >8 | >8 | >8 | >8 |
| SO₂Bu | N(Pr)(CH₂OMe) | 1/2 | 1/2 | 1/2 | 1/4 | >8 | >8 | >8 | >8 |
| SO₂(CH₂)₂OEt | N(Pr)((CH₂)₂OMe) | 1/4 | 1/4 | 1/4 | 1/4 | 4 | >8 | >8 | >8 |
| SO₂Pr | N(Et)((CH₂)₃OEt) | 1/4 | 1/4 | 1/4 | 1/4 | 2 | 2 | 2 | 2 |
| SO₂i-Pr | N(Et)((CH₂)₃OEt) | 1/4 | 1/4 | 1/4 | 1/4 | 1 | 2 | 2 | >8 |
| SO₂Bu | N(Et)((CH₂)₃OEt) | 1/4 | 1/4 | 1/4 | 1/4 | 1 | 4 | 2 | >8 |
| SO₂i-Bu | N(Et)((CH₂)₃OEt) | 1/4 | 1/4 | 1/4 | 1/4 | 2 | 2 | 2 | >8 |
| SO₂Pen | N(Et)((CH₂)₃OEt) | 1/2 | 1/2 | 1/4 | 1/2 | >8 | >8 | >8 | >8 |
| SO₂(CH₂)₂OMe | N(i-Bu)(allyl) | 1/2 | 1 | 1/2 | 1/8 | 4 | 4 | 4 | 4 |
| SO₂(CH₂)₂OEt | N(i-Bu)(allyl) | 1/16 | 1 | 1/2 | 1/4 | >8 | >8 | >8 | >8 |
| SO₂(CH₂)₂OMe | N(Pen)(allyl) | 1/16 | 1/8 | 1/4 | 1/8 | 4 | >8 | >8 | >8 |
| SO₂(CH₂)₂OEt | N(Pen)(allyl) | 1/16 | 1/8 | 1/16 | 1/16 | 2 | >8 | >8 | >8 |
| SO₂Et | N(Et)((CH₂)₃OMe) | 1/16 | 1/16 | 1/8 | 1/8 | 1 | 2 | 4 | >8 |
| SO₂Pr | N(Et)((CH₂)₃OMe) | 1/16 | 1/16 | 1/16 | 1/16 | 1 | 2 | 2 | >8 |
| SO₂Pr | N(Et)(CHMeCH₂OPr) | 1/4 | 1 | 1/4 | 1/4 | 4 | >8 | >8 | >8 |
| SO₂Bu | " | 1/4 | 1/2 | 1/4 | 1/4 | >8 | >8 | >8 | >8 |
| SO₂Bu | N(Et)((CH₂)₃OMe) | 1/16 | 1/4 | 1/16 | 1/16 | 2 | 4 | >8 | >8 |
| SO₂(CH₂)₂OEt | N(2-methylallyl)₂ | 1/4 | 1/4 | 1/2 | 1/4 | >8 | >8 | >8 | >8 |

Table 2-continued

| Compound (II) | | Minimum rate (lb./acre) | | | | | | | |
|---|---|---|---|---|---|---|---|---|---|
| | | Control | | | | | Phytotoxicity | | |
| R³ | NR¹R² | CG | BG | YF | JG | M | CO | SB | P |
| SO₂(CH₂)₂OMe | N(2-methyl-allyl)₂ | 1/4 | 1/4 | 1/4 | 1/4 | 1 | 4 | 2 | >8 |
| SO₂Pr | N<Et, (CH₂)₂O-i-Pr | 1/16 | 1/4 | 1/8 | 1/4 | 1 | >8 | >8 | >8 |
| SO₂(CH₂)₂OEt | N<Et, (CH₂)₂O-i-Pr | 1/4 | 1/4 | 1/4 | 1/4 | 1 | >8 | >8 | >8 |
| SO₂(CH₂)₂OMe | N<Pr, (CH₂)₂OMe | 1/4 | 1/2 | 1/4 | 1/2 | >8 | >8 | >8 | >8 |
| SO₂(CH₂)₂OMe | N<Et, (CH₂)₂OEt | 1/32 | 1/16 | 1/32 | 1/32 | 1/2 | >8 | >8 | >8 |
| SO₂Et | N<Et, 2-chloroethyl | 1/4 | 1/4 | 1/4 | 1 | >8 | >8 | >8 | >8 |
| SO₂Et | N<Pr, 2-chloroethyl | 1/16 | 1/8 | 1/8 | 1/16 | 1/2 | 2 | 2 | 1 |
| SO₂Et | N<Pr, 2-chloroallyl | 1/8 | 1/8 | 1/4 | 1 | >8 | >8 | >8 | >8 |
| SO₂Pr | " | 1/16 | 1/16 | 1/4 | 1/8 | 4 | >8 | >8 | >8 |
| SO₂i-Pr | " | 1/8 | 1/16 | 1/2 | 1/4 | >8 | >8 | >8 | >8 |
| SO₂i-Bu | " | 1/8 | 1/8 | 1/2 | 1/4 | >8 | >8 | >8 | >8 |
| SOCHClPr | NPr₂ | 1/4 | 1/4 | 1/2 | 1/4 | >8 | >8 | >8 | >8 |
| SO₂s-Bu | N<Pr, 2-chloroallyl | 1 | 1/8 | 1/4 | 1/4 | >8 | >8 | 4 | >8 |
| SO₂(CH₂)₂OEt | N<Et, 2-chloroallyl | 1/2 | 1/4 | 1/2 | 1/4 | >8 | >8 | >8 | >8 |
| SO₂Me | N<Pr, 2-chloroethyl | 1/16 | 1/4 | 1/4 | 1/4 | 4 | 4 | 2 | 4 |
| SO₂Bu | N<Pr, 2-chloroallyl | 1/4 | 1/2 | 1/2 | 1/4 | >8 | >8 | >8 | >8 |
| SO₂Pen | " | 1/4 | 1/2 | 1/4 | 1/4 | >8 | >8 | >8 | >8 |
| SO₂(CH₂)₂OMe | N<Pr, 2-chloroallyl | 1/2 | 1/2 | 1/4 | 1/4 | >8 | >8 | >8 | >8 |
| SO₂Et | N<Et, 2-chloroallyl | 1/8 | 1/8 | 1/4 | 1/4 | >8 | >8 | >8 | >8 |
| SO₂Pr | " | 1/8 | 1/4 | 1/4 | 1/4 | >8 | >8 | >8 | >8 |
| SO₂(CH₂)₂OEt | N<allyl, 2-chloroallyl | 1/2 | 1 | 1/2 | 1/2 | >8 | >8 | >8 | >8 |
| SO₂(CH₂)₂OMe | N<Et, 2-chloroallyl | 1/4 | 1/8 | 1/4 | 1/2 | 4 | 4 | >8 | >8 |
| SO₂(CH₂)₂OEt | N<Et, 2-chloroallyl | 1/4 | 1/4 | 1/8 | 1/8 | 2 | 4 | >8 | >8 |
| SO₂(CH₂)₂OEt | N(cyclopropyl)Et | 1/2 | 1/2 | 1/2 | 1/4 | 2 | 2 | 2 | >8 |
| SO₂Et | " | 1/32 | 1/32 | 1/32 | 1/32 | 1/2 | 4 | >8 | 4 |
| SO₂Pr | " | 1/32 | 1/32 | 1/16 | 1/8 | 1/2 | 4 | >8 | 4 |
| SO₂i-Pr | " | 1/32 | 1/32 | 1/4 | 1/16 | 1 | 2 | 2 | >8 |
| SO₂Bu | N<Et, cyclopropyl | 1/32 | 1/32 | 1/8 | 1/8 | 1/2 | 4 | 2 | 4 |
| SO₂Et | N<Pr, cyclopropyl | 1/16 | 1/16 | 1/2 | 1/2 | 2 | >8 | >8 | >8 |
| SO₂Pr | " | 1/16 | 1/8 | 1/4 | 1/4 | 2 | >8 | >8 | >8 |
| SO₂i-Pr | " | 1/8 | 1/8 | 1/16 | 1/4 | 2 | >8 | >8 | >8 |
| SO₂Bu | " | 1/16 | 1/16 | 1/8 | 1/8 | 1 | >8 | >8 | >8 |

TABLE 3

| Compound III SO$_2$NR$^3$R$^4$ | CONR$^1$R$^2$ | Control CG | BG | YF | JG | Minimum rate (lb./acre) M | Phytotoxicity CO | SB | P |
|---|---|---|---|---|---|---|---|---|---|
| NMe$_2$ | N(allyl)$_2$ | 1/4 | 1/4 | 1/8 | 1/4 | 2 | 2 | 4 | >8 |
| N(Bu)Me | " | 1/16 | 1/16 | 1/16 | 1/16 | 4 | >8 | >8 | >8 |
| N(s-Bu)Me | " | 1/32 | 1/32 | 1/8 | 1/32 | 1/2 | >8 | >8 | >8 |
| N(Me)(cyclohexyl) | " | 1/4 | 1/4 | 1/4 | 1/2 | 2 | >8 | >8 | >8 |
| N(allyl)Me | " | 1/16 | 1/32 | 1/8 | 1/16 | 2 | >8 | >8 | >8 |
| NEt$_2$ | " | 1/32 | 1/32 | 1/32 | 1/32 | 2 | 4 | 4 | >8 |
| N(Et)Hex | " | 1/4 | 1/4 | 1/8 | 1/4 | 2 | >8 | >8 | >8 |
| NPr$_2$ | " | 1/4 | 1/4 | 1/4 | 1/16 | 4 | >8 | 4 | >8 |
| N(i-Pr)Pr | " | 1/16 | 1/32 | 1/8 | 1/4 | 2 | >8 | >8 | >8 |
| N(Pr)Bu | " | 1/8 | 1/2 | 1/2 | 1/2 | 2 | 2 | 2 | 4 |
| NBu$_2$ | " | 1/8 | 1/2 | 1/4 | 1/8 | 4 | 4 | >8 | >8 |
| N(allyl)$_2$ | " | 1/4 | 1/4 | 1/8 | 1/16 | 2 | 4 | 4 | 4 |
| N(Me-allyl)$_2$ | " | 1/16 | 1/16 | 1/4 | 1/2 | >8 | >8 | >8 | >8 |
| pyrrolidino | " | 1/8 | 1/8 | 1/8 | 1/16 | 4 | 2 | 4 | >8 |
| piperidyl | N(allyl)$_2$ | 1/8 | 1/8 | 1/16 | 1/2 | 4 | 2 | 4 | 4 |
| morpholino | " | 1/2 | 1/2 | 1/4 | 1/4 | 4 | >8 | 4 | >8 |
| 2,6-dimethyl-morpholino | " | 1/8 | 1/4 | 1/8 | 1/8 | >8 | 4 | >8 | 4 |
| 4-methyl-piperidino | " | 1/8 | 1/8 | 1/8 | 1/8 | >8 | >8 | >8 | >8 |
| hexamethylene-imino | " | 1/4 | 1/4 | 1/4 | 1/4 | >8 | >8 | >8 | >8 |
| heptamethylene-imino | " | 1/4 | 1/8 | 1/4 | 1/4 | >8 | >8 | >8 | >8 |
| NMe$_2$ | NEt$_2$ | 1/4 | 1/2 | 1/8 | 1/2 | 2 | 4 | 4 | >8 |
| NEt$_2$ | " | 1/16 | 1/8 | 1 | 1/2 | 4 | >8 | >8 | >8 |
| N(allyl)$_2$ | " | 1/16 | 1/16 | 1/32 | 1/32 | 1/2 | >8 | >8 | >8 |
| N(Me)Bu | " | 1/32 | 1/32 | 1/8 | 1/4 | 2 | >8 | >8 | >8 |
| N(s-Bu)Me | " | 1/8 | 1/32 | 1/32 | 1/4 | 1 | 4 | 4 | >8 |
| N(Me)(cyclohexyl) | " | 1 | 1/4 | 1/2 | 1/2 | 4 | >8 | >8 | >8 |
| N(allyl)Me | " | 1/16 | 1/4 | 1/4 | 1/4 | 2 | 4 | >8 | >8 |
| piperidyl | " | 1/8 | 1/8 | 1/32 | 1/4 | 1 | >8 | >8 | >8 |
| morpholino | " | 1/16 | 1/4 | 1/8 | 1/16 | 1 | 1 | 2 | >8 |
| 2,6-dimethyl-morpholino | NEt$_2$ | 1/32 | 1/4 | 1/8 | 1/4 | 1 | 4 | 4 | >8 |
| pyrrolidino | N(Me)Et | 1/32 | 1/16 | 1/32 | 1/32 | 1 | 1 | 2 | 2 |
| pyrrolidino | N(Me)Bu | 1/4 | 1/4 | 1/4 | 1/4 | 1 | 2 | 4 | 8 |
| N(Me)Bu | N(Me)(cyclohexyl) | 1/4 | 1/2 | 1/4 | 1/4 | 2 | >8 | >8 | >8 |
| N(allyl)Me | " | 1/16 | 1/4 | 1/2 | 1/2 | 4 | >8 | 4 | >8 |
| NEt$_2$ | " | 1/16 | 1/16 | 1/8 | 1/2 | 4 | >8 | 4 | >8 |
| N(allyl)$_2$ | " | 1/8 | 1/4 | 1/2 | 1/4 | 2 | >8 | >8 | >8 |
| pyrrolidino | " | 1/4 | 1/4 | 1/8 | 1/4 | 4 | 4 | >8 | 4 |
| NEt$_2$ | N(Et)Bu | 1/16 | 1/6 | 1/8 | 1/8 | 4 | 4 | >8 | >8 |
| N(Me)Bu | " | 1/2 | 1/2 | 1/2 | 1/4 | 2 | >8 | 4 | >8 |
| N(allyl)Me | " | 1/32 | 1/32 | 1/32 | 1/32 | >8 | >8 | 4 | >8 |
| piperidyl | " | 1/4 | 1/4 | 1/4 | 1/4 | 2 | >8 | >8 | >8 |
| N(allyl)Me | N(allyl)Et | 1/32 | 1/32 | 1/32 | 1/8 | 2 | >8 | 2 | >8 |
| NEt$_2$ | N(allyl)Et | 1/8 | 1/4 | 1/8 | 1/16 | 1 | 2 | 2 | 2 |
| N(allyl)$_2$ | N(Et)Bu | 1/32 | 1/32 | 1/16 | 1/32 | 4 | >8 | >8 | >8 |
| N(allyl)$_2$ | N(allyl)Et | 1/16 | 1/16 | 1/8 | 1/8 | 4 | >8 | 4 | >8 |
| pyrrolidino | " | 1/16 | 1/16 | 1/16 | 1/16 | 1/4 | 4 | 2 | >8 |
| piperidyl | " | 1/16 | 1/16 | 1/16 | 1/16 | 1/2 | >8 | >8 | >8 |
| N(Me)Bu | N(allyl)Pr | 1/16 | 1/16 | 1/32 | 1/16 | 2 | >8 | >8 | >8 |
| N(allyl)Me | " | 1/16 | 1/16 | 1/4 | 1/16 | 2 | >8 | >8 | >8 |
| NEt$_2$ | " | 1/16 | 1/16 | 1/16 | 1/16 | 1 | >8 | 4 | >8 |
| N(allyl)$_2$ | " | 1/16 | 1/8 | 1/8 | 1/4 | 2 | >8 | >8 | >8 |
| N(allyl)$_2$ | N(Pr)(prop-2-ynyl) | 1/16 | 1/4 | 1/4 | 1/8 | >8 | 4 | >8 | 4 |
| N(Me)Bu | " | 1/4 | 1/4 | 1/16 | 1/16 | >8 | >8 | >8 | >8 |
| N(allyl)Me | " | 1/16 | 1/8 | 1/2 | 1/16 | >8 | 4 | 4 | >8 |
| pyrrolidino | N(allyl)Pr | 1/16 | 1/8 | 1/16 | 1/4 | 2 | >8 | 4 | >8 |
| piperidyl | " | 1/16 | 1/8 | 1/16 | 1/8 | 4 | 4 | >8 | >8 |
| piperidyl | N(Pr)(prop-2-ynyl) | 1/8 | 1/4 | 1/8 | 1/8 | >8 | 2 | 4 | >8 |
| N(Et)Bu | N(allyl)$_2$ | 1/8 | 1/16 | 1/4 | 1/8 | 4 | >8 | >8 | >8 |
| N(allyl)Hex | " | 1/4 | 1/2 | 1/2 | 1/2 | 2 | 4 | 4 | >8 |
| N(allyl)$_2$ | N(2-methylallyl)$_2$ | 1/8 | 1/8 | 1/8 | 1/4 | >8 | >8 | >8 | >8 |
| NBu$_2$ | NEt$_2$ | 1/4 | 1/4 | 1/4 | 1/4 | 2 | >8 | 4 | >8 |
| N(allyl)Pr | " | 1/16 | 1/8 | 1/16 | 1/8 | 1 | 4 | 4 | >8 |
| N(Me)Pen | " | 1/2 | 1/4 | 1/4 | 1/2 | 2 | >8 | >8 | >8 |
| N(CH$_2$CH$_2$OEt)$_2$ | " | 1/4 | 1/4 | 1/4 | 1/4 | 1 | >8 | 2 | >8 |
| N(Me)Hex | " | 1/8 | 1/4 | 1/8 | 1/4 | 4 | >8 | >8 | >8 |
| N(Et)Pen | " | 1/16 | 1/16 | 1/8 | 1/8 | 2 | >8 | 4 | >8 |
| N(allyl)Et | " | 1/8 | 1/8 | 1/16 | 1/16 | 4 | 4 | >8 | >8 |
| N(Pr)Hex | " | 1/2 | 1/2 | 1/2 | 1/2 | 4 | 4 | >8 | >8 |
| N(Bu)Et | " | 1/16 | 1/16 | 1/16 | 1/16 | 1/2 | >8 | 2 | >8 |
| NEt$_2$ | N(Me)Bu | 1/8 | 1/16 | 1/16 | 1/16 | 1 | 4 | 2 | >8 |
| N(allyl)$_2$ | " | 1/16 | 1/16 | 1/16 | 1/16 | 1 | 4 | 1 | >8 |
| N(Me)Et | N(allyl)$_2$ | 1/16 | 1/16 | 1/16 | 1/16 | 1/2 | 2 | 1 | >8 |
| N(Me)Pen | " | 1/8 | 1/8 | 1/4 | 1/4 | >8 | >8 | >8 | >8 |

TABLE 3-continued

| Compound III SO$_2$NR$^3$R$^4$ | CONR$^1$R$^2$ | Control CG | BG | YF | JG | Minimum rate (lb./acre) M | Phytotoxicity CO | SB | P |
|---|---|---|---|---|---|---|---|---|---|
| N(Me)Hex | " | 1/16 | 1/8 | 1/16 | 1/16 | 4 | >8 | >8 | >8 |
| N(Et)Pen | " | 1/8 | 1/16 | 1/8 | 1/16 | >8 | >8 | >8 | >8 |
| N(Et)(cyclopropyl) | " | 1/4 | 1/4 | 1/4 | 1/4 | 4 | 2 | 1 | 2 |
| N(allyl)Et | " | 1/16 | 1/8 | 1/8 | 1/8 | >8 | >8 | >8 | >8 |
| N(Et)(2-allyloxyethyl) | " | 1/4 | 1/4 | 1/4 | 1/4 | 4 | 1 | >8 | >8 |
| N(Et)(2-chloroallyl) | " | 1/4 | 1/4 | 1/4 | 1/4 | >8 | 4 | 4 | >8 |
| N(allyl)Pr | " | 1/16 | 1/8 | 1/8 | 1/8 | 4 | 4 | >8 | >8 |
| N(Pr)(prop-2-ynyl) | " | 1/8 | 1/16 | 1/8 | 1/8 | 4 | >8 | >8 | >8 |
| N(Pr)(CH$_2$)$_2$OMe | " | 1/4 | 1/2 | 1/4 | 1/2 | >8 | 4 | 4 | >8 |
| N(Pr)(CH$_2$CH$_2$Cl) | " | 1/16 | 1/4 | 1/16 | 1/4 | >8 | >8 | >8 | >8 |
| N(Pr)(2-chloroallyl) | " | 1/4 | 1/8 | 1/8 | 1/8 | >8 | 4 | 4 | >8 |
| N(Me)Bu | N(Me)Hex | 1/4 | 1/2 | 1/4 | 1/4 | >8 | >8 | >8 | >8 |
| piperidyl | N(Et)s-Bu | 1/16 | 1/8 | 1/16 | 1/16 | 4 | >8 | 4 | >8 |
| N(allyl)$_2$ | " | 1/4 | 1/8 | 1/4 | 1/4 | 1 | 4 | 4 | >8 |
| N(s-Bu)Me | N(Et)Bu | 1/4 | 1/4 | 1/4 | 1/4 | >8 | >8 | >8 | >8 |
| N(allyl)Pr | N(allyl)Et | 1/16 | 1/16 | 1/16 | 1/16 | 1 | >8 | 4 | >8 |
| NEt$_2$ | N(Hex)Et | 1/4 | 1/4 | 1/4 | 1/4 | 4 | >8 | >8 | >8 |
| NEt$_2$ | N(Et)(cyclopropyl) | 1/4 | 1/4 | 1/4 | 1/4 | 2 | 2 | 1 | >8 |
| NMe$_2$ | N(allyl)Et | 1/8 | 1/16 | 1/16 | 1/16 | 1/2 | 2 | 4 | 4 |
| NEt$_2$ | N(i-Bu)Et | 1/4 | 1/4 | 1/4 | 1/4 | 2 | >8 | >8 | >8 |
| N(Me)Bu | N(Pr)(CH$_2$)$_2$OEt | 1 | 1/2 | 1/2 | 1/2 | >8 | >8 | >8 | >8 |
| N(Me)Bu | N(allyl)Pr | 1/16 | 1/16 | 1/16 | 1/16 | 1/2 | 4 | 1 | >8 |
| N(Et)Bu | N(allyl)Pr | 1/16 | 1/16 | 1/16 | 1/16 | 2 | 2 | 2 | >8 |
| N(Me)s-Bu | " | 1/4 | 1/4 | 1/4 | 1/2 | 4 | 4 | 4 | >8 |
| NEt$_2$ | N(Pr)(prop-2-ynyl) | 1/8 | 1/4 | 1/8 | 1/2 | 4 | 4 | 4 | >8 |
| NEt$_2$ | N(Pr)(CH$_2$CH$_2$Cl) | 1/2 | 1/2 | 1/2 | 1/4 | >8 | >8 | >8 | >8 |
| N(allyl)$_2$ | N(Et)(2-chloroallyl) | 1/16 | 1/8 | 1/8 | 1/2 | >8 | >8 | >8 | >8 |
| NEt$_2$ | N(Et)(2-allyloxyethyl) | 1/2 | 1/2 | 1/4 | 1/2 | 2 | >8 | >8 | >8 |
| NEt$_2$ | N(Pr)CH$_2$OMe | 1/8 | 1/8 | 1/8 | 1/8 | >8 | >8 | >8 | >8 |
| NEt$_2$ | N(Pr)(CH$_2$)$_2$OMe | 1/8 | 1/8 | 1/4 | 1/16 | 2 | >8 | >8 | >8 |
| NEt$_2$ | N(Et)(CH$_2$)$_3$OMe | 1/8 | 1/8 | 1/4 | 1/4 | 2 | >8 | >8 | >8 |
| NEt$_2$ | N(Et)(CH$_2$)$_2$OEt | 1/4 | 1/8 | 1/2 | 1/2 | >8 | >8 | >8 | >8 |
| N(allyl)$_2$ | N(Et)(CH$_2$)$_2$OEt | 1/8 | 1/4 | 1/2 | 1/4 | 4 | >8 | 4 | >8 |
| N(allyl)$_2$ | N(Et)(CH$_2$)$_3$OMe | 1/16 | 1/4 | 1/8 | 1/8 | 2 | 2 | >8 | >8 |
| NEt$_2$ | N(Et)CH$_2$CH$_2$Cl | 1/4 | 1/4 | 1/4 | 1/4 | 1 | >8 | 1 | >8 |
| NEt$_2$ | N(Et)(2-chloroallyl) | 1/8 | 1/4 | 1/8 | 1/4 | >8 | >8 | >8 | >8 |
| NEt$_2$ | N(allyl)Pen | 1/8 | 1/8 | 1/8 | 1/8 | 4 | >8 | >8 | >8 |
| N(allyl)$_2$ | N(allyl)Pen | 1/16 | 1/8 | 1/16 | 1/4 | >8 | >8 | >8 | >8 |
| N(allyl)$_2$ | N(Me)Et | 1/16 | 1/16 | 1/8 | 1/16 | 1 | 2 | 2 | >8 |
| pyrrolidino | " | 1/32 | 1/16 | 1/32 | 1/32 | 1 | 1 | 2 | 2 |
| N(allyl)$_2$ | N(allyl)Me | 1/16 | 1/16 | 1/16 | 1/16 | 1 | 2 | 4 | >8 |
| NEt$_2$ | " | 1/8 | 1/16 | 1/16 | 1/8 | 1/2 | 2 | 1 | >8 |

TABLE 3-continued

| SO₂NR³R⁴ | Compound III CONR¹R² | CG | BG | YF | JG | M | CO | SB | P |
|---|---|---|---|---|---|---|---|---|---|
| | | | | Control | | | Phytotoxicity | | |
| N(Me)Bu | " | 1/16 | 1/16 | 1/16 | 1/16 | 2 | 2 | 4 | >8 |
| NEt₂ | N(i-Pr)Et | 1/16 | 1/16 | 1/16 | 1/16 | 1 | >8 | 2 | >8 |
| N(allyl)Hex | N(Pr)Et | 1/2 | 1/2 | 1/2 | 1/2 | >8 | >8 | >8 | >8 |
| N(Et)Bu | N(i-Pr)Et | 1/16 | 1/16 | 1/16 | 1/16 | 1 | >8 | 1 | >8 |
| N(allyl)₂ | " | 1/16 | 1/16 | 1/16 | 1/16 | 1 | >8 | 2 | >8 |
| NEt₂ | N(Et)Bu | 1/8 | 1/8 | 1/8 | 1/4 | >8 | >8 | >8 | >8 |
| N(allyl)₂ | N(Et / prop-2-ynyl) | 1/4 | 1/2 | 1/8 | 1/8 | >8 | >8 | >8 | >8 |
| NEt₂ | " | 1/8 | 1/4 | 1/8 | 1/4 | >8 | >8 | >8 | >8 |
| N(Me)Bu | " | 1/8 | 1/4 | 1/4 | 1/4 | 2 | >8 | 4 | >8 |
| N(Bu)Me | N(Et)s-Bu | 1/8 | 1/8 | 1/4 | 1/8 | >8 | >8 | >8 | 2 |
| N(allyl)₂ | " | 1/16 | 1/16 | 1/16 | 1/16 | 4 | >8 | 4 | >8 |
| N(Me)Bu | N(Pr / (CH₂)₂OMe) | 1/16 | 1/16 | 1/16 | 1/16 | 1 | 4 | 4 | 1 |
| piperidyl | N(Pr / (CH₂)₂OMe) | 1/16 | 1/16 | 1/16 | 1/16 | >8 | >8 | 4 | >8 |
| NEt₂ | N(Pr / (CH₂)₂OEt) | 1/2 | 1/4 | 1/2 | 1/2 | >8 | >8 | >8 | >8 |
| N(Me)Bu | N(Et / (CH₂)₂OEt) | 1/4 | 1/2 | 1/2 | 1/2 | 4 | >8 | >8 | >8 |
| NEt₂ | N(Et)Pen | 1/4 | 1/8 | 1/16 | 1/16 | 4 | >8 | >8 | >8 |
| N(allyl)₂ | " | 1/8 | 1/4 | 1/16 | 1/8 | 4 | >8 | >8 | >8 |
| N(allyl)₂ | N(Pr / 2-chloroallyl) | 1 | 1/4 | 1/2 | 1/4 | >8 | >8 | >8 | >8 |
| NEt₂ | N(allyl)i-Pr | 1/4 | 1/4 | 1/4 | 1/4 | 1 | >8 | >8 | >8 |
| N(allyl)₂ | " | 1/16 | 1/4 | 1/4 | 1/4 | 1 | >8 | 4 | >8 |
| N(allyl)Me | N(Pr / 2-chloroallyl) | 1 | 1/4 | 1/2 | 1/2 | >8 | >8 | >8 | >8 |
| NEt₂ | N(allyl)Bu | 1/2 | 1/2 | 1/4 | 1/4 | 2 | >8 | 4 | >8 |
| NEt₂ | N(allyl)Hex | 1 | 1/2 | 1/4 | 1/4 | >8 | >8 | >8 | >8 |
| NMe₂ | N(allyl)i-Bu | 1/16 | 1/16 | 1/16 | 1/16 | 1 | >8 | 2 | >8 |
| NEt₂ | " | 1/4 | 1/4 | 1/4 | 1/4 | 1 | 4 | >8 | >8 |
| piperidyl | N(Me)Hex | 1/4 | 1/4 | 1/4 | 1/4 | 4 | 4 | 2 | >8 |
| N(Me / 4-fluorophenyl) | N(allyl)₂ | 1/16 | 1/16 | 1/8 | 1/8 | >8 | >8 | >8 | >8 |
| N(Me / 4-chlorophenyl) | " | 1/4 | 1/16 | 1/4 | 1/4 | 4 | >8 | 4 | >8 |
| N(Me / 4-bromophenyl) | " | 1/8 | 1/8 | 1/2 | 1 | >8 | >8 | >8 | >8 |
| N(Me / 4-bromophenyl) | NEt₂ | 1/16 | 1/4 | 1/4 | 1/8 | 2 | >8 | 4 | >8 |
| N(Me / 4-chlorophenyl) | " | 1/16 | 1/16 | 1/32 | 1/16 | 1 | >8 | 4 | >8 |
| N(Me / 4-flu) | " | 1/16 | 1/16 | 1/8 | 1/32 | 2 | >8 | >8 | >8 |
| N(Me / 4-flu) | N(Me)Bu | 1/16 | 1/16 | 1/4 | 1/16 | >8 | >8 | 2 | >8 |
| " | N(Me)Hex | 1/4 | 1/4 | 1/2 | 1/4 | >8 | >8 | >8 | >8 |
| " | N(Me / cyclohexyl) | 1/16 | 1/16 | 1/16 | 1/16 | >8 | 4 | >8 | >8 |
| " | N(Et)Bu | 1/16 | 1/16 | 1/16 | 1/16 | 4 | >8 | >8 | >8 |
| " | N(allyl)Et | 1/4 | 1/4 | 1/4 | 1/4 | 2 | 4 | 4 | >8 |
| " | N(allyl)Pr | 1/16 | 1/16 | 1/16 | 1/16 | >8 | >8 | >8 | >8 |
| N(Me / 4-fluorophenyl) | N(Et / 2-chloroallyl) | 1/8 | 1/16 | 1/8 | 1/16 | >8 | >8 | 4 | >8 |
| " | N(allyl)Me | 1/8 | 1/16 | 1/8 | 1/8 | 2 | 4 | >8 | >8 |
| " | N(Pr)Et | 1/16 | 1/16 | 1/16 | 1/16 | 1 | >8 | 2 | >8 |
| " | N(Et / allyl) | 1/4 | 1/4 | 1/4 | 1/4 | >8 | >8 | >8 | >8 |
| " | N(Et)Bu | 1/8 | 1/8 | 1/16 | 1/16 | 2 | >8 | 4 | >8 |
| " | N(Pr / (CH₂)₂OMe) | 1/16 | 1/16 | 1/16 | 1/16 | 1/4 | >8 | >8 | >8 |
| " | N(Et)Pen | 1/8 | 1/4 | 1/4 | 1/8 | >8 | >8 | 4 | >8 |
| " | N(allyl)i-Bu | 1/16 | 1/16 | 1/16 | 1/16 | 4 | 2 | 2 | >8 |

For purposes of comparison, various 1,2,4-triazoles within the scope of the isomeric formulae A but outside the scope of the formulae, I, II and III (compounds of the formula III are wholly outside the scope of formulae A), were included in the glasshouse trials described above, using application rates logarithmically reducing from 32 lb./acre. The results obtained are given in the following Tables 4 and 5, in which "*" designates a compound that is specifically exemplified in U.S. Pat. No. 3,308,131. The compounds that gave no control of any of the weeds crabgrass, barnyard grass, yellow foxtail and Johnson grass at the maximum application rate of 32 lb./acre are listed in Table 5. In view of their lack of activity against the weeds, these compounds were not included in the crop tests. Of the compounds listed in Table 5, those that are believed to have been obtained as a mixture of isomers (corresponding to formulae A) containing appreciably more than 10 % of each isomer, or those in which the isomeric structure is uncertain, are designated 1( 2)- in the nomenclature of the carbamoyl group. The remaining compounds are believed to have been obtained substantially as the isomer given, or predominantly as this isomer with less than 10% of the other isomer.

Table 4

| Compound ($A_2$, X=O, $R^R$=H) | | Minimum rate (lb./acre) | | | | | | | |
|---|---|---|---|---|---|---|---|---|---|
| | | control | | | | phytotoxicity | | | |
| $R^7$ | $NR^5R^6$ | CG | BG | YF | JG | CO | SB | M | P |
| * Me | $NMe_2$ | 1 | 16 | 2 | 2 | 4 | 8 | 4 | 8 |
| * Cl | " | 4 | 2 | 2 | 2 | 2 | 4 | 2 | 4 |
| * Br | " | 4 | 4 | 32 | 4 | 1 | 1 | 2 | 4 |
| * SMe | " | 1 | 4 | 4 | 2 | 1/2 | 2 | 2 | 2 |

TABLE 5

Compounds with the following substituents on the 1,2,4-triazole ring gave no weed control at 32 lb./acre.

* 1-dimethylcarbamoyl
* 1-dimethylthiocarbamoyl
  1(2)-dimethylthiocarbamoyl-3-ethylthio
  1(2)-diethylthiocarbamoyl-3-ethylthio
* 1(2)-dimethylthiocarbamoyl-3-methylthio-5-methyl
* 1(2)-dimethylcarbamoyl-3-methylsulphonyl-5-methyl
* 1(2)-diethylcarbamoyl-3-methylthio-5-methyl
* 1(2)-N-methyl-N-n-butylcarbamoyl-3-methylthio-5-methyl
* 1(2)-dimethylcarbamoyl-3-ethylthio-5-methyl
* 1-dimethylcarbamoyl-3-dodecylthio-5-methyl
  1-dimethylcarbamoyl-3-n-hexylthio
  1-dimethylcarbamoyl-3-cyclohexylthio
  1-dimethylcarbamoyl-3-dodecylthio
* 1-dimethylcarbamoyl-3-undecyl-5-methylthio
  1-dimethylcarbamoyl-3-benzyl
* 1-dimethylcarbamoyl-3-benzylthio-5-methyl
* 1-dimethylcarbamoyl-3-phenyl-5-methylthio
* 1-dimethylcarbamoyl-3-p-nitrophenylthio-5-methyl
  1-dimethylcarbamoyl-3-(2,4-dinitrophenylthio)
* 1-dimethylcarbamoyl-3,5-dimethyl
* 1-dimethylcarbamoyl-3-(2-diethylaminoethylthio)-5-methyl
* 1- dimethylcarbamoyl-3-ethoxycarbonylmethylthio-5-methyl
* 1-dimethylcarbamoyl-3-(1-dimethylcarbamoyl-1,2,4-triazol-3-yldithio)
* 1-(4-methylpiperidinocarbonyl)
* 1(2)-pyrrolidinocarbonyl-3-methylthio-5-methyl
  1-piperidinocarbonyl-3-ethylthio
  1(2)-(4-methylpiperazinocarbonyl)-3-ethylthio
  1-(1,2,3,4-tetrahydroquinolinocarbonyl)-3-ethylthio
  1-(2)-(N-methyl-N-methoxycarbamoyl)-3-ethylthio
  1-diallylcarbamoyl
  1(2)-diallylcarbamoyl-3-ethylthio-5-methyl
  1-diallylcarbamoyl-3-(2-diethylaminoethylthio)
  1-diallylcarbamoyl-3-methoxycarbonylmethyl
  1-di(cyanomethyl)carbamoyl-3-ethylthio The results given above show that the compounds listed in Tables 1, 2 and 3 are markedly superior to the compounds listed in Tables 4 and 5 in respect of their high level of selective pre-emergence activity against all four of the weeds crabgrass, barnyard grass, yellow foxtail and Johnson grass in the crops cotton, soyabean, maize and peanut.

It can be seen from the foregoing description that the compounds of the present invention are of value for the pre-weed emergence control of graminaceous weeds in a variety of crops, for example cotton, leguminous crops such as soyabean and peanut, and cereals such as maize. However, it will be appreciated that the individual compounds of the present invention are not all equivalent in their level of herbicidal activity and selectivity characteristics. Accordingly the optimum compound for one particular use is not necessarily the optimum compound for another particular use.

Insecticidal and miticidal tests have been carried out with a variety of compounds of the present invention. The compounds tested were found to have little or no activity against insects, for example *Plutella maculipennis*, *Phaedon cochlearieae*, and aphids such as *Aphis fabae* and *Megoura viciae*. The compounds tested were also found to have little or no activity against mites, for example *Tetranychus urticae*.

Regarding the mammalian toxicity of the compounds of the present invention, acute oral toxicity studies in mice have given satisfactory results. In these studies, the compounds of the present invention have been found to be less toxic than certain closely related 1,2,4-triazoles, for example 1-dimethylcarbamoyl-3-methylthio-1,2,4-triazole.

PREPARATION OF COMPOUNDS OF FORMULA I

The compounds of formula I may be prepared by the hereinafter described processes, which are analogous to known processes for preparing similar compounds.

One such process comprises reacting a triazole of the general formula

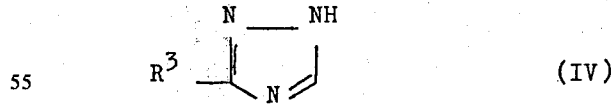

(IV)

in which $R^3$ is as hereinbefore defined for formula I, with a carbamoyl halide of the general formula Z—CONR$^1$R$^2$ (V) in which $R^1$ and $R^2$ are as hereinbefore defined for formula I and Z is chlorine, fluorine or bromine, preferably chlorine. The reaction is suitably effected in the presence of an inert organic liquid as the reaction medium, which is preferably a solvent for the reactants. Advantageously the reaction is effected in the presence of a suitable acid-binding agent, for example a tertiary amine such as triethylamine or pyridine, in order to absorb the hydrogen halide produced in the reaction. In an alternative procedure, the triazole of the general formula IV may be converted to an alkali metal (for example sodium) salt thereof prior to the reaction with the carbamoyl halide. The alkali metal salt may be obtained by reacting the triazole of the general formula IV with an alkali metal hydride, amide or alkoxide, in accordance with known methods.

The carbamoyl halides of the general formula V may be prepared by reacting a secondary amine of the general formula $HNR^1R^2$, in which $R^1$ and $R^2$ are as defined above, with a carbonyl halide $COZ_2$, in accordance with known methods.

The compounds of formula I may also be prepared by a process which comprises reacting a carbamoyl halide of the general formula

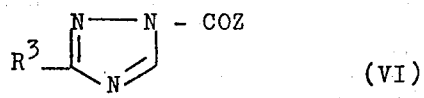

(VI)

in which $R^3$ and Z are as defined above, with a secondary amine of the general formula $HNR^1R^2$, in which $R^1$ and $R^2$ are as defined above. The reaction is suitably effected in the presence of an inert organic liquid as the reaction medium, which is preferably a solvent for the reactants. Advantageously the reaction is effected in the presence of a suitable acid-binding agent, for example a tertiary amine such as triethylamine or pyridine.

The carbamoyl halides of general formula VI may be prepared from the triazoles of general formula IV by reaction with a carbonyl halide $COZ_2$, preferably phosgene, in accordance with known methods.

The triazoles of general formula IV may be prepared by alkylation or alkenylation of 3-mercapto-1,2,4-triazole, followed by oxidation of the 3-alkylthio group where appropriate in accordance with known methods.

The compounds of formula I may also be prepared by a process which comprises reacting a carbonylbis-triazole of the general formula

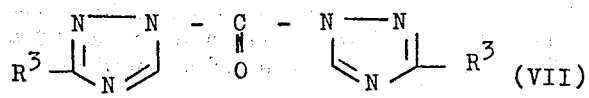

(VII)

in which $R^3$ is as defined above, with a secondary amine of the general formula $HNR^1R^2$, in which $R^1$ and $R^2$ are as defined above. The reaction is suitably effected in the presence of an inert organic liquid as the reaction medium, which is preferably a solvent for the reactants.

The carbonylbistriazoles of the general formula VII may be prepared by reacting a triazole of the hereinbefore defined general formula IV with about 0.5 molecular proportions of a carbonyl halide $COZ_2$, preferably phosgene, in accordance with known methods. The reaction is preferably effected in the presence of a suitable acid-binding agent, for example pyridine. After formation of the carbonylbistriazole, it is often convenient to react it, without isolation, with the amine of general formula $HNR^1R^2$.

It will be appreciated by those skilled in the art that the triazoles represented by the general formula IV are tautomeric and that, for convenience, general formula IV depicts the structure of one tautomer.

The compounds of formula I in which $R^3$ is an alkylsulphinyl or alkylsulphonyl group may also be prepared by a process which comprises the oxidation of a compound of the general formula

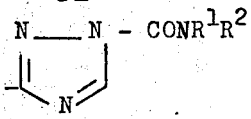

(VIII)

in which R is an appropriate alkyl group and $R^1$ and $R^2$ are as defined above, in accordance with known methods. The oxidation may be effected, for example, by reaction with hydrogen peroxide or peracetic acid.

PREPARATION OF COMPOUNDS OF FORMULA II

The compounds of formula II may be prepared by the hereinafter described processes, which are analogous to known processes for preparing similar compounds.

One such process comprises reacting a triazole of the general formula

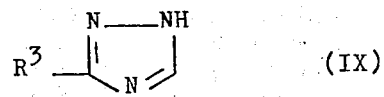

(IX)

in which $R^3$ is as hereinbefore defined for formula II, with a carbamoyl halide of the general formula Z-$CONR^1R^2$ (X) in which $R^1$ and $R^2$ are as hereinbefore defined for formula II and Z is chlorine, fluorine or bromine, preferably chlorine. The reaction is suitably effected in the presence of an inert organic liquid as the reaction medium, which is preferably a solvent for the reactants. Advantageously the reaction is effected in the presence of a suitable acid-binding agent, for example a tertiary amine such as triethylamine or pyridine, in order to absorb the hydrogen halide produced in the reaction. In an alternative procedure, the triazole of the general formula IX may be converted to an alkali metal (for example sodium) salt thereof prior to the reaction with the carbamoyl halide. The alkali metal salt may be obtained by reacting the triazole of the general formula IX with an alkali metal hydride, amide or alkoxide, in accordance with known methods.

The carbamoyl halides of the general formula X may be prepared by reacting a secondary amine of the general formula $HNR^1R^2$, in which $R^1$ and $R^2$ are as defined above, with a carbonyl halide $COZ_2$, in accordance with known methods.

The compounds of formula II may also be prepared by a process which comprises reacting a carbamoyl halide of the general formula

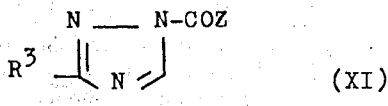

(XI)

in which $R^3$ and Z are as defined above, with a secondary amine of the general formula $HNR^1R^2$, in which $R^1$ and $R^2$ are as defined above. The reaction is suitably effected in the presence of an inert organic liquid as the reaction medium, which is preferably a solvent for the reactants. Advantageously the reaction is effected in the presence of a suitable acid-binding agent, for example a tertiary amine such as triethylamine or pyridine.

The carbamoyl halides of general formula XI may be prepared from the triazoles of general formula IX by reaction with a carbonyl halide $COZ_2$, preferably phosgene, in accordance with known methods.

The triazoles of general formula IX may be prepared by alkylation or alkenylation of 3-mercapto-1,2,4-triazole (e.g. by reaction of 3-mercapto-1,2,4-triazole with a compound $R^3$-Y wherein Y is chloro or bromo), followed by oxidation of the 3-thio group where appropriate, in accordance with known methods.

The compounds of formula II may also be prepared by a process which comprises reacting a carbonylbistriazole of the general formula

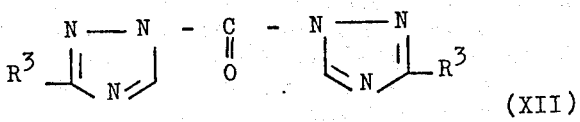
(XII)

in which $R^3$ is as defined above, with a secondary amine of the general formula $HNR^1R^2$, in which $R^1$ and $R^2$ are as defined above. The reaction is suitably effected in the presence of an inert organic liquid as the reaction medium, which is preferably a solvent for the reactants.

The carbonylbistriazoles of the general formula XII may be prepared by reacting a triazole of the hereinbefore defined general formula IX with about 0.5 molecular proportions of a carbonyl halide $COZ_2$, preferably phosgene, in accordance with known methods. The reaction is preferably effected in the presence of a suitable acid-binding agent, for example pyridine. After formation of the carbonylbistriazole, it is often convenient to react it, without isolation, with the amine of general formula $HNR^1R^2$.

It will be appreciated by those skilled in the art that the triazoles represented by the general formula IX are tautomeric and that, for convenience, general formula IX depicts the structure of one tautomer.

The compounds of formula II in which $R^3$ is an alkoxyalkylsulphinyl, haloalkylsulphinyl, alkylsulphonyl, alkoxyalkylsulphonyl, or haloalkylsulphonyl group may also be prepared by a process which comprises the oxidation of a compound of the general formula

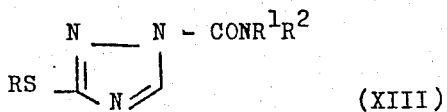
(XIII)

in which R is an appropriate alkyl, alkoxyalkyl or haloalkyl group and $R^1$ and $R^2$ are as defined above, in accordance with known methods. The oxidation may be effected, for example, by reaction with hydrogen peroxide or peracetic acid.

The intermediate triazoles of the general formula IX, with the exception of the compounds in which $R^3$ is methylsulphonyl are novel compounds.

PREPARATION OF COMPOUNDS OF FORMULA III

The compounds of formula III may be prepared by the hereinafter described processes, which are analogous to known processes for preparing similar compounds.

One such process comprises reacting a sulphamoyltriazole of the general formula

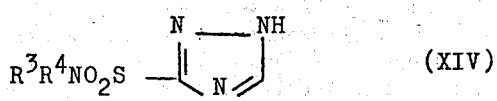
(XIV)

in which $R^3$ and $R^4$ are as hereinbefore defined for formula III, with a carbamoyl halide of the general formula $Z\text{-}CONR^1R^2$ (XV) in which $R^1$ and $R^2$ are as hereinbefore defined for formula III and Z is chlorine, fluorine or bromine, preferably chlorine. The reaction is suitably effected in the presence of an inert organic liquid as the reaction medium, which is preferably a solvent for the reactants. Advantageously the reaction is effected in the presence of a suitable acid-binding agent, for example a tertiary amine such as triethylamine or pyridine, in order to absorb the hydrogen halide produced in the reaction. In an alternative procedure, the triazole of the general formula XIV may be converted to an alkali metal (for example sodium) salt thereof prior to the reaction with the carbamoyl halide. The alkali metal salt may be obtained by reacting the triazole of the general formula XIV with an alkali metal hydride, amide or alkoxide, in accordance with known methods.

The carbamoyl halides of the general formula XV may be prepared by reacting a secondary amine of the general formula $HNR^1R^2$, in which $R^1$ and $R^2$ are as defined above, with a carbonyl halide $COZ_2$, in accordance with known methods.

The compounds of formula III may also be prepared by a process which comprises reacting a carbamoyl halide of the general formula

(XVI)

in which $R^3$, $R^4$ and Z are as defined above, with a secondary amine of the general formula $HNR^1R^2$, in which $R^1$ and $R^2$ are as defined above. The reaction is suitably effected in the presence of an inert organic liquid as the reaction medium, which is preferably a solvent for the reactants. Advantageously the reaction is effected in the presence of a suitable acid-binding agent, for example a tertiary amine such as triethylamine or pyridine.

The carbamoyl halides of general formula XVI may be prepared from the triazoles of general formula XIV by reaction with a carbonyl halide $COZ_2$, preferably phosgene, in accordance with known methods.

The sulphamoyltriazoles of the general formula XIV (with the exception of $NR^3R^4$ = dimethylamino or 1-piperidyl), are novel compounds. The compounds may be prepared by a process which comprises reacting a 1,2,4-triazole-3-sulphonyl halide, preferably the chloride, with an amine of the general formula $HNR^3R^4$ (XVII). The reaction may be effected in an aqueous medium, or in a suitable inert organic liquid, which is preferably a solvent for the reactants. Diethyl ether and tetrahydrofuran are examples of suitable inert organic liquids that in many instances are solvents for the reactants. The reaction is preferably effected in the presence of a suitable acid-binding agent, for example triethylamine or an excess of the amine $HNR^3R^4$, in order to absorb the hydrogen halide produced in the reaction. The reaction is suitably effected at temperatures in the range 10° – 30°C.

The compounds of formula III may also be prepared by a process which comprises reacting a carbonylbistriazole of the general formula

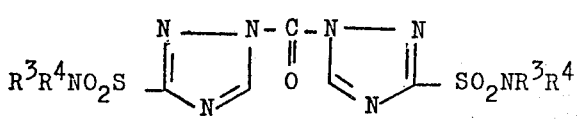

(XVIII)

in which $R^3$ and $R^4$ are as defined above, with a secondary amine of the general formula $HNR^1R^2$, in which $R^1$ and $R^2$ are as defined above. The reaction is suitably effected in the presence of an inert organic liquid as the reaction medium, which is preferably a solvent for the reactants.

The carbonylbistriazoles of the general formula XVIII may be prepared by reacting a triazole of the hereinbefore defined general formula XIV with about 0.5 molecular proportions of a carbonyl halide $COZ_2$, preferably phosgene, in accordance with known methods. The reaction is preferably effected in the presence of a suitable acid-binding agent, for example pyridine. After formation of the carbonylbistriazole, it is often convenient to react it, without isolation, with the amine of general formula $HNR^1R^2$.

It will be appreciated by those skilled in the art that the triazoles represented by the general formula XIV are tautomeric and that, for convenience, general formula XIV depicts the structure of one tautomer.

It will be appreciated by those skilled in the art that the acylation reactions described above in the preparations of compounds of formulae I, II and III can theoretically give two isomeric products, one (hereinafter referred to as 1-isomer) having the general formula I, II or III and the other (hereinafter referred to as 2-isomer) having the general formula

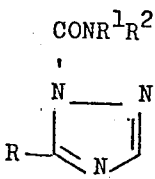

where R is the group $R^3$ of formulae I or II or the group $R^3R^4NO_2S-$ of formula III.

It is believed that the solid compounds of the present invention, after purification by standard methods such as crystallization, are obtained as substantially pure 1-isomer. The liquid compounds of the present invention, as isolated by standard methods such as distillation in vacuo, are believed to be obtained as components of an isomeric mixture consisting predominantly of the 1-isomer together with a minor proportion, generally less than about 10% of 2-isomer.

The following Examples illustrate the invention.

EXAMPLE 1

Dipropylcarbamoyl chloride (5.4 g.) was added to a solution of 5.25 g. 3-propylsulphonyl-1,2,4-triazole and 6 ml. dry triethylamine in 25 ml. dry tetrahydrofuran and the resulting mixture was refluxed under anhydrous conditions for 2.5 hours. The cooled reaction mixture was filtered to remove triethylamine hydrochloride, the filtrate was distilled under reduced pressure to remove solvent, and the residue was dissolved in methylene dichloride. The resulting solution was washed with ice-cold 0.1N aqueous sodium hydroxide (2 × 50 ml.), then with 0.01N aqueous sulphuric acid (50 ml.) and finally with water. The resulting solution was dried over anhydrous sodium sulphate and was then distilled under reduced pressure to give a solid residue. This residue was recrystallized twice from petroleum ether (b.p. 60° – 80°C.) to give 1-dipropylcarbamoyl-3-propylsulphonyl-1,2,4-triazole, m.p. 79° – 80°C. Elemental analysis satisfactory.

The 3-propylsulphonyl-1,2,4-triazole used in the above reaction was prepared as follows.

3-Mercapto-1,2,4-triazole (20.2 g.) was added to a solution of 4.8 g. sodium in 150 ml. absolute ethanol. When dissolution was complete 24.6 g. propyl bromide was added. The stirred mixture was gradually heated to boiling under reflux, refluxed for 1 hour, cooled to room temperature and filtered. The filtrate was distilled to dryness under reduced pressure and the residue was dissolved in ether. The resulting solution was filtered, dried over anhydrous sodium sulphate and distilled under reduced pressure to give 3-propylthio-1,2,4-triazole, b.p. 143° – 144°C./1 mm. This product solidified, m.p. 53° – 56°C.

To a solution of 14.3 g. 3-propylthio-1,2,4-triazole in 100 ml. glacial acetic acid was added 28.5 ml. 100 vol. hydrogen peroxide solution (2.5 molecular proportions). The solution was heated gradually to 95° – 100°C., kept at this temperature for 2 hours and then distilled to dryness under reduced pressure. The residue was recrystallized from toluene to give 3-propylsulphonyl-1,2,4-triazole, m.p. 116° – 117°C. Elemental analysis satisfactory.

EXAMPLE 2

A mixture of 5.75 g. 3-propylthio-1,2,4-triazole, 6.8 g. diallylcarbamoyl chloride, 25 ml. dry tetrahydrofuran and 8 ml. dry triethylamine was refluxed under anhydrous conditions for 3 hours. The reaction mixture was worked up as described in Example 1 to produce an oil which was distilled under reduced pressure to give 1-diallylcarbamoyl-3-propylthio-1,2,4-triazole, b.p. 134° – 135°C./0.1 mm. Gas-liquid chromatographic (GLC) assay indicated a content of 1-isomer of 94.2%. Elemental analysis satisfactory.

The diallylcarbamoyl chloride used in the above preparation was prepared as follows. Phosgene was passed into refluxing ethyl acetate (100 ml.) until the liquid was saturated with phosgene. To the refluxing, stirred solution was added dropwise a solution of diallylamine (50 g.) in ethyl acetate (100 ml.), maintaining a brisk flow of phosgene. The rate of addition of the solution of diallylamine was such that solid diallylamine hydrochloride did not accumulate in the reaction mixture. When the addition was complete, the flow of phosgene into the stirred, refluxing reaction mixture was maintained for 30 minutes. The reaction mixture was distilled under reduced pressure to remove the solvent and give the product, diallylcarbamoyl chloride, as an oil, b.p. 67° – 69°C./3 mm.

EXAMPLE 3

3-n-Butylthio-1,2,4-triazole, m.p. 35° – 37°C., was prepared by alkylation of 3-mercapto-1,2,4-triazole in an analogous manner to that described in Example 1.

A mixture of 6.3 g. 3-n-butylthio-1,2,4-triazole, 6.8 g. diallylcarbamoyl chloride, 25 ml. tetrahydrofuran and 8 ml. dry triethylamine was refluxed under anhydrous conditions for 4 hours. The reaction mixture was worked up as described in Example 1 to produce an oil which was distilled under reduced pressure to give 1-diallylcarbamoyl-3-n-butylthio-1,2,4-triazole, b.p.

157°C./0.6 mm. (95.0% 1-isomer by GLC assay). Elemental analysis satisfactory.

EXAMPLE 4

3-n-Pentylthio-1,2,4-triazole, m.p. 54° – 56°C., was prepared by alkylation of 3-mercapto-1,2,4-triazole in an analogous manner to that described in Example 1.

A mixture of 9.5 g. 3-n-pentylthio-1,2,4-triazole, 8.07 g. diallylcarbamoyl chloride, 100 ml. dry tetrahydrofuran and 8 ml. dry triethylamine was refluxed under anhydrous conditions for 68 hours. The reaction mixture was worked up as described in Example 1, using ether in place of methylene dichloride, to produce an oil which was distilled under reduced pressure to give 1-diallylcarbamoyl-3-n-pentylthio-1,2,4-triazole, b.p. 135°C./0.1 mm. (90.6% 1-isomer by GLC assay). Elemental analysis satisfactory.

EXAMPLE 5

A mixture of 5.25 g. 3-propylsulphonyl-1,2,4-triazole, 5.3 g. diallylcarbamoyl chloride, 25 ml. dry tetrahydrofuran and 6 ml. dry triethylamine was refluxed under anhydrous conditions for 1.5 hours. The reaction mixture was worked up as described in Example 1 to give a solid product which was recrystallized from petroleum ether (b.p. 60° – 80°C.) to give 1-diallylcarbamoyl-3-propylsulphonyl-1,2,4-triazole, m.p. 41° – 42°C. Elemental analysis satisfactory.

EXAMPLE 6

3-Isopropylthio-1,2,4-triazole, m.p. 77° – 80°C., was prepared by alkylation of 3-mercapto-1,2,4-triazole in a manner analogous to that described in Example 1.

A mixture of 5.75 g. 3-isopropylthio-1,2,4-triazole, 6.8 g. diallylcarbamoyl chloride, 25 ml. dry tetrahydrofuran and 8 ml. dry triethylamine was refluxed under anhydrous conditions for 2.5 hours. The reaction mixture was worked up as described in Example 1 to produce an oily residue which was distilled under reduced pressure to give 1-diallylcarbamoyl-3-isopropylthio-1,2,4-triazole, b.p. 133°C./0.4 mm. – 144°C./0.9 mm. (97.2% 1-isomer by GLC assay). Elemental analysis satisfactory.

EXAMPLE 7

3-Isobutylthio-1,2,4-triazole, m.p. 61° – 63.5°C., was prepared by alkylation of 3-mercapto-1,2,4-triazole in an analogous manner to that described in Example 1.

A mixture of 7.85 g. 3-isobutylthio-1,2,4-triazole, 10.97 g. diallylcarbamoyl chloride, 100 ml. dry tetrahydrofuran and 11 ml. dry triethylamine was refluxed under anhydrous conditions for 48 hours. The reaction mixture was worked up as described in Example 1, using ether in place of methylene dichloride. An oily residue was obtained which was distilled under reduced pressure to give 1-diallylcarbamoyl-3-isobutylthio-1,2,4-triazole, b.p. 116° – 118°C./0.5 mm. (96.0% 1-isomer by GLC assay).

The following compounds were prepared in an analogous manner.

1-dipropylcarbamoyl-3-n-butylthio-1,2,4-triazole, b.p. 140° – 141°C./0.1 mm. (92.4% 1-isomer by GLC assay).
1-dipropylcarbamoyl-3-isobutylthio-1,2,4-triazole, b.p. 128° – 129°C./0.15 mm. (92.1% 1-isomer by GLC assay).
1-dipropylcarbamoyl-3-sec.butylthio-1,2,4-triazole, b.p. 140° – 142°C./0.5 mm. (90.8% 1-isomer by GLC assay).
1-dipropylcarbamoyl-3-n-pentylthio-1,2,4-triazole, b.p. 140° – 142°C./0.1 mm. (81.4% 1-isomer by GLC assay).

Satisfactory elemental analyses were obtained for all the above compounds.

EXAMPLE 8

3-Mercapto-1,2,4-triazole was alkylated to 3-methylthio-1,2,4-triazole, m.p. 103° – 104°C., and this compound was oxidized to 3-methylsulphonyl-1,2,4-triazole, m.p. 202°C., by methods analogous to those described in Example 1.

Dipropylcarbamoyl chloride (5.5 g.) was added to a solution of 4.4 g. 3-methylsulphonyl-1,2,4-triazole and 6 ml. dry triethylamine in 25 ml. dry tetrahydrofuran and the resulting mixture refluxed for 2.5 hours under anhydrous conditions. The cooled reaction mixture was filtered to remove triethylamine hydrochloride and the filtrate poured with stirring into 150 ml. ice-cold 0.1N aqueous sodium hydroxide. The precipitated product was collected by filtration, washed with ice-cold water, dried, and crystallized twice from toluene to give 1-dipropylcarbamoyl-3-methylsulphonyl-1,2,4-triazole, m.p. 94°C. Elemental analysis satisfactory.

EXAMPLE 9

3-n-Butylsulphonyl-1,2,4-triazole, m.p. 96° – 97°C., was prepared by oxidation of 3-n-butylthio-1,2,4-triazole in an analogous manner to that described in Example 1.

A mixture of 5.7 g. 3-n-butylsulphonyl-1,2,4-triazole, 5.4 g. dipropylcarbamoyl chloride, 25 ml. dry tetrahydrofuran and 6 ml. dry triethylamine was refluxed under anhydrous conditions for 1.5 hours. The reaction mixture was worked up as described in Example 1 to produce a solid product which was recrystallized from petroleum ether (60° – 80°C.) to give 1-dipropylcarbamoyl-3-n-butylsulphonyl-1,2,4-triazole, m.p. 46° – 47°C. Elemental analysis satisfactory.

In an analogous manner there was prepared 1-dipropylcarbamoyl-3-n-pentylsulphonyl-1,2,4-triazole, m.p. 38.5° – 39.5°C. (from petroleum ether, b.p. 60° – 68°C.). Elemental analysis satisfactory.

EXAMPLE 10

3-n-Pentylsulphonyl-1,2,4-triazole, m.p. 108° – 109°C., was prepared by the oxidation of 3-n-pentylthio-1,2,4-triazole in an analogous manner to that described in Example 1.

A mixture of 10.2 g. 3-pentylsulphonyl-1,2,4-triazole, 8.2 g. diallylcarbamoyl chloride, 75 ml. dry tetrahydrofuran and 7.5 ml. dry triethylamine was refluxed under anhydrous conditions for 1.5 hours. The reaction mixture was worked up as described in Example 1, using ether in place of methylene dichloride. An oily residue was obtained which was distilled under reduced pressure to give a product, b.p. 193° – 194°C./0.25 mm., which solidified on cooling. This product was recrystallized from petroleum ether (b.p. 60° – 80°C.) to give 1-diallylcarbamoyl-3-n-pentylsulphonyl-1,2,4-triazole, m.p. 28° – 30°C. Elemental analysis satisfactory.

EXAMPLE 11

A mixture of 5.7 g. 3-butylsulphonyl-1,2,4-triazole, 5.3 g. diallylcarbamoyl chloride, 25 ml. dry tetrahydrofuran and 6 ml. dry triethylamine was refluxed under anhydrous conditions for 1.5 hours. The reaction mixture was worked up as described in Example 1 to give 1-diallylcarbamoyl-3-butylsulphonyl-1,2,4-triazole as an oil which was heated under reduced pressure (100°C./0.5 mm.) for 30 minutes to remove all traces of volatile material. Refractive index of product $n_D^{26}$ 1.5132. Elemental analysis satisfactory.

EXAMPLE 12

3-Isorpopylsulphonyl-1,2,4-triazole, m.p. 170° – 171°C., was prepared by the oxidation of 3-isopropylthio-1,2,4-triazole by a method analogous to that described in Example 1.

A mixture of 7.0 g. 3-isopropylsulphonyl-1,2,4-triazole, 7.0 ml. diallylcarbamoyl chloride, 25 ml. dry tetrahydrofuran and 8 ml. dry triethylamine was refluxed for 1 hour under anhydrous conditions. The reaction mixture was worked up as described in Example 1 to give 1-diallylcarbamoyl-3-isopropylsulphonyl-1,2,4-triazole as an oil which was heated under reduced pressure (100°C./0.5 mm.) for 1 hour to remove all traces of volatile material. Refractive index of product $n_D^{26}$ 1.5158. Elemental analysis satisfactory.

EXAMPLE 13

3-Ethylthio-1,2,4-triazole, m.p. 63° – 64°C., was prepared by alkylation of 3-mercapto-1,2,4-triazole in an analogous manner to that described in Example 1.

Diallylcarbamoyl chloride (8 g.) was added to a solution of 7.1 g. 3-ethylthio-1,2,4-triazole and 8 ml. dry triethylamine in 50 ml. dry tetrahydrofuran and the mixture refluxed for 4 hours under anhydrous conditions. The cooled reaction mixture was diluted with 100 ml. toluene and washed, firstly with 1N aqueous sodium hydroxide and then with water. The resulting solution was dried over anhydrous sodium sulphate and distilled under reduced pressure to remove the solvent and give 1-diallylcarbamoyl-3-ethylthio-1,2,4-triazole, b.p. 120° – 122°C./0.1 mm. (97.1% 1-isomer by GLC assay).

The following compounds were prepared in an analogous manner.

1-dipropylcarbamoyl-3-ethylthio-1,2,4-triazole, b.p. 118° – 120°C./0.05 mm. (92.1% 1-isomer by GLC assay).

1-dipropylcarbamoyl-3-propylthio-1,2,4-triazole, b.p. 136°C./0.15 mm. (92.6% 1-isomer by GLC assay).

Satisfactory elemental analyses were obtained for all of the above compounds.

EXAMPLE 14

To a solution of 15.7 g. 3-butylthio-1,2,4-triazole in 60 ml. glacial acetic acid was added 100 vol. hydrogen peroxide solution (11.4 ml., 1 molecular proportion). The reaction mixture was cooled occasionally during 1 hour to maintain the reaction temperature at 25° – 30°C., and then kept at room temperature for 24 hours. The resulting solution was distilled under reduced pressure to produce a solid residue which was recrystallized from ethyl acetate to give 3-n-butylsulphinyl-1,2,4-triazole, m.p. 82° – 83°C.

A mixture of 5.2 g. 3-butylsulphinyl-1,2,4-triazole, 6.0 g. diallylcarbamoyl chloride, 25 ml. dry tetrahydrofuran and 7.5 ml. dry triethylamine was refluxed under anhydrous conditions for 2 hours. The reaction mixture was filtered to remove triethylamine hydrochloride and the filtrate distilled under reduced pressure to remove solvent. Finally the residue was maintained at 100°C./0.5 mm. for 30 minutes in order to remove all traces of volatile material from the product. The product, 1-diallylcarbamoyl-3-n-butylsulphinyl-1,2,4-triazole, was obtained as an oil, $n_D^{26}$ 1.5277. Elemental analysis satisfactory.

In a similar manner, the following compounds were obtained as oils with satisfactory elemental analyses.

1-diallylcarbamoyl-3-propylsulphinyl-1,2,4-triazole, $n_D^{26}$ 1.5314.

1-diallylcarbamoyl-3-n-pentylsulphinyl-1,2,4-triazole, $n_D^{26}$ 1.5247.

1-diallylcarbamoyl-3-isobutylsulphinyl-1,2,4-triazole, $n_D^{25}$ 1.5272.

1-dipropylcarbamoyl-3-n-pentylsulphinyl-1,2,4-triazole, $n_D^{26}$ 1.5068.

1-dipropylcarbamoyl-3-isobutylsulphinyl-1,2,4-triazole, $n_D^{25}$ 1.5066.

1-diethylcarbamoyl-3-t.butylsulphinyl-1,2,4-triazole, m.p. 65° – 67°C.

1-diethylcarbamoyl-3-sec.butylsulphinyl-1,2,4-triazole, $n_D^{26}$ 1.5182.

The intermediate 3-alkylsulphinyl-1,2,4-triazoles used in the above reactions were prepared by oxidation of the appropriate 3-alkylthio-1,2,4-triazoles in a manner analogous to that described above for 3-n-butylsulphinyl-1,2,4-triazole. The physical characteristics of these intermediate compounds are as follows.

3-propylsulphinyl-1,2,4-triazole, m.p. 67° – 68°C.
3-n-pentylsulphinyl-1,2,4-triazole, m.p. 62° – 63°C.
3-isobutylsulphinyl-1,2,4-triazole, m.p. 89.5° – 91.5°C.
3-sec.butylsulphinyl-1,2,4-triazole, m.p. 78° – 80°C.
3-t.butylsulphinyl-1,2,4-triazole, m.p. 163°C. (with decomposition).

EXAMPLE 15

3-Ethylsulphinyl-1,2,4-triazole, m.p. 86° – 88°C., was prepared by the oxidation of 3-ethylthio-1,2,4-triazole in a manner analogous to that described in Example 14.

A mixture of 4.35 g. 3-ethylsulphinyl-1,2,4-triazole, 6.0 ml. diallylcarbamoyl chloride, 25 ml. dry tetrahydrofuran and 7.5 ml. dry triethylamine was refluxed under anhydrous conditions for 2 hours. The reaction mixture was filtered and the filtrate distilled under reduced pressure to remove solvent, giving a residual oil which solidified on cooling. This solid product was recrystallized from petroleum ether (b.p. 60° – 80°C.) to give 1-diallylcarbamoyl-3-ethylsulphinyl-1,2,4-triazole, m.p. 41° – 43°C. Elemental analysis satisfactory.

EXAMPLE 16

A mixture of 4.1 g. 3-methylsulphonyl-1,2,4-triazole, 4.75 g. diallylcarbamoyl chloride, 20 ml. dry tetrahydrofuran and 5.5 ml. dry triethylamine was refluxed under anhydrous conditions for 1 hour. The reaction mixture was filtered and the filtrate was distilled to dryness under reduced pressure. The solid residue was recrystallized from a mixture of toluene and petroleum ether (b.p. 40° – 60°C.) to give 1-diallylcarbamoyl-3-methylsulphonyl-1,2,4-triazole, m.p. 52° – 54°C. Elemental analysis satisfactory.

EXAMPLE 17

3-Ethylsulphonyl-1,2,4-triazole, m.p. 145°C., was prepared by the oxidation of 3-ethylthio-1,2,4-triazole in an analogous manner to that described in Example 1.

A mixture of 6.45 g. 3-ethylsulphonyl-1,2,4-triazole, 6.6 g. diallylcarbamoyl chloride, 25 ml. dry tetrahydrofuran and 8 ml. dry triethylamine was refluxed under anhydrous conditions for 1.5 hours. The cooled reaction mixture was filtered and the filtrate distilled under reduced pressure to remove solvent and give a product which distilled at 187°C./0.2 mm. This product solidified and was recrystallized from petroleum ether (b.p. 60° – 80°C.) to give 1-diallylcarbamoyl-3-ethylsulphonyl-1,2,4-triazole, m.p. 39° – 42°C. Elemental analysis satisfactory.

In an analogous manner there was prepared 1-(N-isopropyl-N-propylcarbamoyl)-3-ethylsulphonyl-1,2,4-triazole, b.p. 176° – 178°C./0.2 mm. (93.3% 1-isomer by GLC assay). Elemental analysis satisfactory.

EXAMPLE 18

3-Isopropylsulphinyl-1,2,4-triazole, m.p. 105° – 107°C., was prepared by the oxidation of 3-isopropylthio-1,2,4-triazole in a manner analogous to that described in Example 14. Elemental analysis satisfactory.

A mixture of 6.4 g. 3-isopropylsulphinyl-1,2,4-triazole, 8.0 ml. diallylcarbamoyl chloride, 25 ml. dry tetrahydrofuran and 10 ml. dry triethylamine was refluxed under anhydrous conditions for 2 hours. The cooled reaction mixture was filtered and the filtrate was distilled under reduced pressure to give an oily residue which subsequently solidified. This solid residue was recrystallized from petroleum ether (b.p. 60° – 80°C.) to give 1-diallylcarbamoyl-3-isopropylsulphinyl-1,2,4-triazole, m.p. 32° – 34°C. Elemental analysis satisfactory.

EXAMPLE 19

A mixture of 4.8 g. 3-propylsulphinyl-1,2,4-triazole, 6.0 ml. dipropylcarbamoyl chloride, 25 ml. dry tetrahydrofuran and 7.5 ml. dry triethylamine was refluxed under anhydrous conditions for 2 hours. The cooled reaction mixture was filtered and the filtrate distilled under reduced pressure to give an oily residue which crystallized on trituration with petroleum ether (b.p. 60° – 80°C.). The resulting solid product was recrystallized from petroleum ether (b.p. 60° – 80°C.) to give 1-dipropylcarbamoyl-3-propylsulphinyl-1,2,4-triazole, m.p. 50° – 52°C. Elemental analysis satisfactory.

EXAMPLE 20

A mixture of 6.9 g. 3-n-butylsulphinyl-1,2,4-triazole, 8.0 ml. dipropylcarbamoyl chloride, 25 ml. dry tetrahydrofuran and 10 ml. dry triethylamine was refluxed under anhydrous conditions for 2 hours. The cooled reaction mixture was filtered and the filtrate distilled under reduced pressure to give an oily residue which subsequently solidified. This solid product was recrystallized from petroleum ether to give 1-dipropylcarbamoyl-3-n-butylsulphinyl-1,2,4-triazole, m.p. 39° – 40°C. Elemental analysis satisfactory.

EXAMPLE 21

A mixture of 6.4 g. 3-isopropylsulphinyl-1,2,4-triazole, 8.0 ml. dipropylcarbamoyl chloride, 25 ml. dry tetrahydrofuran and 10 ml. dry triethylamine was refluxed under anhydrous conditions for 2 hours. The cooled reaction mixture was filtered and the filtrate distilled under reduced pressure to give 1-dipropylcarbamoyl-3-isopropylsulphinyl-1,2,4-triazole as an oily residue which subsequently solidified, m.p. 15° – 20°C. Elemental analysis satisfactory.

EXAMPLE 22

In an analogous manner to that described in Example 20, 3-ethylsulphonyl-1,2,4-triazole was reacted with dipropylcarbamoyl chloride to give 1-dipropylcarbamoyl-3-ethylsulphonyl-1,2,4-triazole, m.p. 44° – 45°C. Elemental analysis satisfactory.

EXAMPLE 23

In an analogous manner to that described in Example 20, 3-isopropylsulphonyl-1,2,4-triazole was reacted with dipropylcarbamoyl chloride (4 hours reflux) to give 1-dipropylcarbamoyl-3-isopropylsulphonyl-1,2,4-triazole, m.p. 61° – 63°C. Elemental analysis satisfactory.

EXAMPLE 24

3-Sec.butylthio-1,2,4-triazole, b.p. 107° – 109°C./0.07 mm. was prepared by the alkylation of 3-mercapto-1,2,4-triazole in an analogous manner to that described in Example 1.

A mixture of 7.9 g. 3-sec.butylthio-1,2,4-triazole, 8.0 g. diallylcarbamoyl chloride, 100 ml. dry tetrahydrofuran and 8 ml. dry triethylamine was refluxed under anhydrous conditions for 24 hours. The reaction mixture was worked up as described in Example 1, using ether in place of methylene dichloride, to produce an oil which was distilled under reduced pressure to give 1-diallylcarbamoyl-3-sec.butylthio-1,2,4-triazole, b.p. 121° – 123°C./0.1 mm. (96% 1-isomer by GLC assay). Elemental analysis satisfactory.

EXAMPLE 25

3-Sec.butylsulphonyl-1,2,4-triazole, m.p. 128° – 130°C., was prepared by the oxidation of 3-sec.butylthio-1,2,4-triazole in an analogous manner to that described in Example 1.

A mixture of 9.5 g. 3-sec.butylsulphonyl-1,2,4-triazole, 7.97 g. diallylcarbamoyl chloride, 50 ml. dry tetrahydrofuran and 7.5 ml. dry triethylamine was refluxed under anhydrous conditions for 5 hours. The reaction mixture was worked up by a method analogous to that described in Example 1 to give an oil which was not distilled but was heated under reduced pressure. (95°C/0.1 mm.) for 4 hours to remove traces of volatile material. The resulting product, 1-diallylcarbamoyl-3-sec.butylsulphonyl-1,2,4-triazole, was obtained as an oil, $n_D^{26}$ 1.5174. (98.9% 1-isomer by GLC assay). Elemental analysis satisfactory.

EXAMPLE 26

3-Sec.butylsulphinyl-1,2,4-triazole, m.p. 78° – 80°C., was prepared by the oxidation of 3-sec.butylthio-1,2,4-triazole in a manner analogous to that described in Example 14.

A mixture of 5.76 g. 3-sec.butylsulphinyl-1,2,4-triazole, 5.31 g. diallylcarbamoyl chloride, 50 ml. dry tetrahydrofuran and 5 ml. dry triethylamine was kept under anhydrous conditions at room temperature for 72 hours. The reaction mixture was filtered and the filtrate evaporated under reduced pressure at room temperature to give a residual oil which was dissolved in methylene dichloride. The resulting solution was washed with water, dried over anhydrous sodium sulphate and distilled under reduced pressure at room temperature to give 1-diallylcarbamoyl-3-sec.butylsulphinyl-1,2,4-triazole as a residual oil, $n_D^{25}$ 1.5268, for which a satisfactory elemental analysis was obtained.

In an analogous manner, using a reaction time of 168 hours at room temperature, there was obtained 1-dipropylcarbamoyl-3-sec.butylsulphinyl-1,2,4-triazole as a residual oil, $n_D^{25}$ 1.5078. Elemental analysis satisfactory.

EXAMPLE 27

A mixture of 9.5 g. 3-sec.butylsulphonyl-1,2,4-triazole, 8.2 g. dipropylcarbamoyl chloride, 50 ml. dry tetrahydrofuran and 7.5 ml. dry triethylamine was refluxed under anhydrous conditions for 2 hours. The reaction mixture was worked up as described in Example 1 to produce a solid product which was recrystallized from a mixture of toluene and petroleum ether (b.p. 60° – 80°C.) to give 1-dipropylcarbamoyl-3-sec.-butylsulphonyl-1,2,4-triazole, m.p. 80° – 81°C. Elemental analysis satisfactory.

EXAMPLE 28

A mixture of 6.45 g. 3-ethylthio-1,2,4-triazole, 7.5 g. diethylcarbamoyl chloride, 40 ml. dry tetrahydrofuran and 7.75 ml. dry triethylamine was refluxed under anhydrous conditions for 22 hours. The reaction mixture was worked up as described in Example 1, using ether in place of methylene dichloride, to give a residual oil. This oil was distilled under reduced pressure to give 1-diethylcarbamoyl-3-ethylthio-1,2,4-triazole, b.p. 110° – 111°C./0.2 mm. (93.6% 1-isomer by GLC assay). Elemental analysis satisfactory.

EXAMPLE 29

A mixture of 4.8 g. 3-propylsulphinyl-1,2,4-triazole, 4.48 g. diethylcarbamoyl chloride, 40 ml. dry tetrahydrofuran and 6 ml. dry triethylamine was refluxed under anhydrous conditions for 5 hours. The cooled reaction mixture was filtered to remove triethylamine hydrochloride. The filtrate was diluted with petroleum ether (b.p. 40°– 60°C.), causing the deposition of an oil which gradually solidified. The solid product was collected and recrystallized from a mixture of ether and petroleum ether (b.p. 40°– 60°C.) to give 1-diethylcarbamoyl-3-propylsulphinyl-1,2,4-triazole, m.p. 50.5° – 51.5°C.

The following compounds were prepared in an analogous manner.

1-diethylcarbamoyl-3-n-butylsulphinyl-1,2,4-triazole, m.p. 64.5° – 65.5°C. (from ether/petroleum ether, b.p. 60° – 80°C.)

1-diethylcarbamoyl-3-methylsulphonyl-1,2,4-triazole, m.p. 89.5° – 90°C. (from benzene/petroleum ether, b.p. 40° – 60°C.)

1-diethylcarbamoyl-3-ethylsulphonyl-1,2,4-triazole, m.p. 53°– 53.5°C. (from benzene/petroleum ether, b.p. 40° – 60°C.)

1-diethylcarbamoyl-3-propylsulphonyl-1,2,4-triazole, m.p. 65° – 65.5°C. (from benzene/petroleum ether, b.p. 40° – 60°C.)

1-diethylcarbamoyl-3-n-butylsulphonyl-1,2,4-triazole, m.p. 60.5° – 61°C. (from benzene/petroleum ether, b.p. 40° – 60°C.)

1-diethylcarbamoyl-3-isopropylsulphonyl-1,2,4-triazole, m.p. 53.5° – 55.5°C. (from benzene/petroleum ether, b.p. 40° – 60°C.)

1-diethylcarbamoyl-3-isobutylsulphonyl-1,2,4-triazole, m.p. 53° – 54.5°C. (from benzene/petroleum ether, b.p. 40° – 60°C.)

1-diethylcarbamoyl-3-n-pentylsulphonyl-1,2,4-triazole, m.p. 37° – 39°C. (from toluene/petroleum ether, b.p. 40° – 60°C.)

1-(N-ethyl-N-isobutylcarbamoyl)-3-ethylsulphonyl-1,2,4-triazole, m.p. 70° – 70.5°C. (from ether/petroleum ether, b.p. 40° – 60°C.)

1-(N-propyl-N-isobutylcarbamoyl)-3-ethylsulphonyl-1,2,4-triazole, m.p. 61° – 61.5°C. (from benzene/petroleum ether, b.p. 40° – 60°C.)

1-(N-propyl-N-prop-2-ynylcarbamoyl)-3-ethylsulphonyl-1,2,4-triazole, m.p. 73° – 73.5°C. (from benzene/petroleum ether, b.p. 40° – 60°C.)

1-(N-n-butyl-N-ethylcarbamoyl)-3-ethylsulphonyl-1,2,4-triazole, m.p. 49° – 50°C. (from ether/petroleum ether, b.p. 40° – 60°C.)

Satisfactory elemental analyses were obtained for all the above compounds.

EXAMPLE 30

A mixture of 7.2 g. 3-propylthio-1,2,4-triazole, 6.8 g. diethylcarbamoyl chloride, 35 ml. dry tetrahydrofuran and 9 ml. dry triethylamine was refluxed under anhydrous conditions for 72 hours. The reaction mixture was worked up as described in Example 1 to produce a residual oil. This oil was distilled under reduced pressure to give 1-diethylcarbamoyl-3-propylthio-1,2,4-triazole, b.p. 118° – 121°C./0.2 mm. (89.9% 1-isomer by GLC assay). Elemental analysis satisfactory.

In a similar manner there was prepared the compound 1-diethylcarbamoyl-3-n-butylthio-1,2,4-triazole, b.p. 124° – 130°C./0.2 mm. (89.4% 1-isomer by GLC assay). Elemental analysis satisfactory.

EXAMPLE 31

A mixture of 6.45 g. 3-ethylthio-1,2,4-triazole, 8.1 g. N-propyl-N-prop-2-ynylcarbamoyl chloride, 25 ml. dry tetrahydrofuran and 8 ml. dry triethylamine was refluxed under anhydrous conditions for 24 hours. The reaction mixture was worked up as described in Example 1, using ether in place of methylene dichloride, to give a residual oil. This residual oil was distilled under reduced pressure to give 1-(N-propyl-N-prop-2-ynylcarbamoyl)-3-ethylthio-1,2,4-triazole, b.p. 124°C./0.05 mm. (97.8% 1-isomer by GLC assay). Elemental analysis satisfactory.

The following compounds were prepared in an analogous manner.

1-(N-allyl-N-ethylcarbamoyl)-3-ethylthio-1,2,4-triazole, b.p. 120°– 122°C./0.05 mm. (95.5% 1-isomer by GLC assay).

1-(N-allyl-N-n-butylcarbamoyl)-3-ethylthio-1,2,4-triazole, b.p. 127°C./0.05 mm. (95.5% 1-isomer by GLC assay).

1-(N-allyl-N-propylcarbamoyl)-3-ethylthio-1,2,4-triazole, b.p. 125°C./0.05 mm. (96.2% 1-isomer by GLC assay).

1-(N-allyl-N-n-hexylcarbamoyl)-3-ethylthio-1,2,4-triazole, b.p. 138°– 140°C./0.03 mm. (94.3% 1-isomer by GLC assay).

1-(N-allyl-N-n-pentylcarbamoyl)-3-ethylthio-1,2,4-triazole, b.p. 142°C./0.1 mm. (91.5% 1-isomer by GLC assay).

1-(N-n-butyl-N-ethylcarbamoyl)-3-ethylthio-1,2,4-triazole, b.p. 120°C./0.05 mm. (89.0% 1-isomer by GLC assay).

1-(N-ethyl-N-propylcarbamoyl)-3-ethylthio-1,2,4-triazole, b.p. 116°C./0.03 mm. (92.1% 1-isomer by GLC assay).

1-(N-ethyl-N-n-pentylcarbamoyl)-3-ethylthio-1,2,4-triazole, b.p. 125°C./0.05 mm. (86.4% 1-isomer by GLC assay).

1-(N-ethyl-N-n-hexylcarbamoyl)-3-ethylthio-1,2,4-triazole, b.p. 140°C./0.1 mm. (92.3% 1-isomer by GLC assay).

1-(N-allyl-N-isobutylcarbamoyl)-3-ethylthio-1,2,4-triazole, b.p. 127° – 130°C./0.2 mm. (94.9% 1-isomer by GLC assay).

1-(N-ethyl-N-isobutylcarbamoyl)-3-ethylthio-1,2,4-triazole, b.p. 120° – 121°C./0.2 mm. (90.1% 1-isomer by GLC assay).

1-(N-ethyl-N-isopentylcarbamoyl)-3-ethylthio-1,2,4-triazole, b.p. 133°C./0.5 mm. (89.3% 1-isomer by GLC assay).

1-(N-propyl-N-isobutylcarbamoyl)-3-ethylthio-1,2,4-triazole, b.p. 124° – 128°C./0.3 mm. (89.7% 1-isomer by GLC assay).

Satisfactory elemental analyses were obtained for all the above compounds.

EXAMPLE 32

A mixture of 5.16 g. 3-ethylthio-1,2,4-triazole, 7.8 g. N-n-butyl-N-propylcarbamoyl chloride, 35 ml. dry tetrahydrofuran and 8 ml. dry triethylamine was refluxed under anhydrous conditions for 24 hours. The reaction mixture was worked up as described in Example 1 to give a residual oil. This oil was distilled under reduced pressure to give 1-(N-n-butyl-N-propylcarbamoyl)-3-ethylthio-1,2,4-triazole, b.p. 127°C./0.2 mm. (91.2% 1-isomer by GLC assay). Elemental analysis satisfactory.

In an analogous manner, the following compound was prepared.

1-(N-n-pentyl-N-propylcarbamoyl)-3-ethylthio-1,2,4-triazole, b.p. 135° – 137°C./0.1 mm. (88.6% 1-isomer by GLC assay). Elemental analysis satisfactory.

EXAMPLE 33

A mixture of 4.83 g. 3-ethylsulphonyl-1,2,4-triazole, 6.0 g. N-n-pentyl-N-propylcarbamoyl chloride, 40 ml. dry tetrahydrofuran and 6 ml. dry triethylamine was refluxed under anhydrous conditions for 24 hours. The cooled reaction mixture was filtered. The filtrate was distilled under reduced pressure to give 1-(N-n-pentyl-N-propylcarbamoyl)-3-ethylsulphonyl-1,2,4-triazole as a residual oil, $n_D^{25}$ 1.4967. (96.5% 1-isomer by GLC assay). Elemental analysis satisfactory.

The following compound was prepared in an analogous manner.

1-(N-n-hexyl-N-propylcarbamoyl)-3-ethylsulphonyl-1,2,4-triazole, an oil, $n_D^{25}$ 1.4945. (95.5% 1-isomer by GLC assay). Elemental analysis satisfactory.

EXAMPLE 34

A mixture of 7.25 g. 3-ethylsulphinyl-1,2,4-triazole, 7.8 g. N-allyl-N-ethylcarbamoyl chloride, 7.5 ml. dry triethylamine and 100 ml. dry tetrahydrofuran was refluxed under anhydrous conditions for 4 hours. The cooled reaction mixture was filtered and the filtrate distilled under reduced pressure to give 1-(N-allyl-N-ethylcarbamoyl)-3-ethylsulphinyl-1,2,4-triazole as a residual oil, $n_D^{25}$ 1.5328.

The following compounds were prepared in an analogous manner.

1-(N-allyl-N-propylcarbamoyl)-3-ethylsulphinyl-1,2,4-triazole, m.p. 59° – 61°C. (from petroleum ether, b.p. 40° – 60°C./benzene)

1-(N-allyl-N-n-butylcarbamoyl)-3-ethylsulphinyl-1,2,4-triazole, m.p. 44° – 46°C. (from benzene/petroleum ether, b.p. 40° – 60°C.)

1-(N-allyl-N-n-pentylcarbamoyl)-3-ethylsulphinyl-1,2,4-triazole, m.p. 50° – 52°C. (from ether, b.p. 40° – 60°C.)

1-(N-allyl-N-n-hexylcarbamoyl)-3-ethylsulphinyl-1,2,4-triazole, m.p. 38° – 41°C. (from benzene/petroleum ether, b.p. 40° – 60°C.)

1-(N-n-butyl-N-ethylcarbamoyl)-3-ethylsulphinyl-1,2,4-triazole, an oil, $n_D^{25}$ 1.5160.

1-(N-ethyl-N-n-hexylcarbamoyl)-3-ethylsulphinyl-1,2,4-triazole, an oil, $n_D^{25}$ 1.5118.

1-(N-allyl-N-isobutylcarbamoyl)-3-ethylsulphinyl-1,2,4-triazole, an oil, $n_D^{25}$ 1.5230.

1-(N-ethyl-N-isobutylcarbamoyl)-3-ethylsulphinyl-1,2,4-triazole, an oil, $n_D^{25}$ 1.5167.

1-(N-ethyl-N-isopentylcarbamoyl)-3-ethylsulphinyl-1,2,4-triazole, an oil, $n_D^{25}$ 1.5127.

Satisfactory elemental analyses were obtained for all the above compounds.

EXAMPLE 35

A mixture of 6.45 g. 3-ethylsulphonyl-1,2,4-triazole, 5.9 g. N-allyl-N-ethylcarbamoyl chloride, 6.5 ml. dry triethylamine and 80 ml. dry tetrahydrofuran was refluxed under anhydrous conditions for 6 hours. The reaction mixture was worked up as described in Example 1 to produce a solid residue which was recrystallized from benzene/petroleum ether, b.p. 40° – 60°C. to give 1-(N-allyl-N-ethylcarbamoyl)-3-ethylsulphonyl-1,2,4-triazole, m.p. 41° – 43°C.

The following compounds were prepared in an analogous manner.

1-(N-allyl-N-propylcarbamoyl)-3-ethylsulphonyl-1,2,4-triazole, m.p. 39° – 41.5°C. (from benzene/petroleum ether, b.p. 40° – 60°C.)

1-(N-allyl-N-n-butylcarbamoyl)-3-ethylsulphonyl-1,2,4-triazole, an oil, $n_D^{25}$ 1.5094. (98.4% 1-isomer by GLC assay).

1-(N-allyl-N-n-pentylcarbamoyl)-3-ethylsulphonyl-1,2,4-triazole, an oil, $n_D^{25}$ 1.5057. (93.0% 1-isomer by GLC assay).

1-(N-allyl-N-n-hexylcarbamoyl)-3-ethylsulphonyl-1,2,4-triazole, an oil, $n_D^{26}$ 1.5034.

1-(N-ethyl-N-n-hexylcarbamoyl)-3-ethylsulphonyl-1,2,4-triazole, an oil, b.p. 183° – 185°C./0.2 mm. (95.4% 1-isomer by GLC assay).

1-(N-allyl-N-isobutylcarbamoyl)-3-ethylsulphonyl-1,2,4-triazole, an oil, $n_D^{25}$ 1.5096. (91.7% 1-isomer by GLC assay).

1-(N-ethyl-N-propylcarbamoyl)-3-ethylsulphonyl-1,2,4-triazole, an oil, $n_D^{26}$ 1.5057. (97.7% 1-isomer by GLC assay).

1-(N-ethyl-N-isopentylcarbamoyl)-3-ethylsulphonyl-1,2,4-triazole, an oil, $n_D^{26}$ 1.4984. (99.1% 1-isomer by GLC assay).

1-(N-propyl-N-sec.butylcarbamoyl)-3-ethylsulphonyl-1,2,4-triazole, an oil, $n_D^{23}$ 1.5008. (94.7% 1-isomer by GLC assay).

Satisfactory elemental analyses were obtained for all the above compounds.

EXAMPLE 36

3-Isobutylsulphonyl-1,2,4-triazole, m.p. 157° – 158.5°C., was prepared by the oxidation of 3-isobutylthio-1,2,4-triazole in a manner analogous to that described in Example 1.

A mixture of 9.5 g. 3-isobutylsulphonyl-1,2,4-triazole, 8.2 g. dipropylcarbamoyl chloride, 7.5 ml. dry triethylamine and 100 ml. dry tetrahydrofuran was refluxed under anhydrous conditions for 11 hours. The reaction mixture was worked up as described in Example 1, using ether in place of methylene dichloride, to give 1-dipropylcarbamoyl-3-isobutylsulphonyl-1,2,4-triazole, m.p. 62° – 63.5°C. (from petroleum ether, b.p. 62° – 68°C.).

The following compounds were prepared in an analogous manner.

1-diallylcarbamoyl-3-isobutylsulphonyl-1,2,4-triazole, an oil, $n_D^{25}$ 1.5137. (99.6% 1-isomer by GLC assay).

1-di(2-methylallyl)carbamoyl-3-ethylsulphonyl-1,2,4-triazole, m.p. 31° – 33°C.

1-di(2-methylallyl)carbamoyl-3-ethylthio-1,2,4-triazole, an oil, b.p. 132° – 134°C./0.2 mm. (94.5% 1-isomer by GLC assay).

Satisfactory elemental analyses were obtained for all the above compounds.

EXAMPLE 37

A mixture of 7.1 g. 3-allylthio-1,2,4-triazole, (m.p. 27° – 30°C., prepared from 3-mercapto-1,2,4-triazole in an analogous manner to that described in Example 1), 8.0 g. diallylcarbamoyl chloride, 7.5 ml. dry triethylamine and 100 ml. dry tetrahydrofuran was refluxed under anhydrous conditions for 48 hours. The reaction mixture was worked up as described in Example 1 to give 1-diallylcarbamoyl-3-allylthio-1,2,4-triazole, b.p. 120° – 122°C./0.1 mm. (95.2% 1-isomer by GLC assay).

The following compounds were prepared in an analogous manner.

1-(N-propyl-N-prop-2-ynylcarbamoyl)-3-allylthio-1,2,4-triazole, b.p. 122° – 124°C./0.1 mm. (94.6% 1-isomer by GLC assay).

1-dipropylcarbamoyl-3-allylthio-1,2,4-triazole, b.p. 133° – 135°C./0.2 mm. (85.5% 1-isomer by GLC assay).

Satisfactory elemental analyses were obtained for all the above compounds.

EXAMPLE 38

In a similar manner to that described in Example 29, there were prepared the following compounds.

1-diethylcarbamoyl-3-isopropylsulphinyl-1,2,4-triazole, m.p. 66° – 68°C. (from benzene/petroleum ether, b.p. 40° – 60°C.). Elemental analysis satisfactory.

1-diethylcarbamoyl-3-isobutylthio-1,2,4-triazole, m.p. 49.5° – 52°C. (from petroleum ether, b.p. 40° – 60°C.). Elemental analysis satisfactory.

EXAMPLE 39

In an analogous manner to that described in Example 30, there were prepared the following compounds.

1-diethylcarbamoyl-3-isopropylthio-1,2,4-triazole, b.p. 129° – 131°C./0.7 mm. (90.5% 1-isomer by GLC assay). Elemental analysis satisfactory.

1-diethylcarbamoyl-3-sec.butylthio-1,2,4-triazole, b.p. 136° – 138°C./0.7 mm. (89.7% 1-isomer by GLC assay). Elemental analysis satisfactory.

EXAMPLE 40

A solution of 25.8 g. 3-ethylthio-1,2,4-triazole and 15.8 g. dry pyridine in 100 ml. dry tetrahydrofuran was added dropwise to 200 ml. of a 10% w/v solution of phosgene in dry tetrahydrofuran (20 g. phosgene, 1 molecular proportion), with stirring and cooling to maintain the reaction temperature at 25° – 30°C. The mixture was stirred at 25° – 30°C. for a further period of 0.5 hour, and was then filtered to remove pyridine hydrochloride formed in the reaction. To the resulting solution of 3-ethylthio-1,2,4-triazole-1-carbonyl chloride was added dropwise a solution of 20.2 g. dipropylamine and 15.8 g. dry pyridine in 50 ml. dry tetrahydrofuran, with stirring and cooling to maintain the reaction temperature at 25° – 30°C. The mixture was stirred at 25° – 30°C. for a further period of 0.5 hour, and was then filtered to remove pyridine hydrochloride formed in the reaction. The filtrate was evaporated under reduced pressure to remove solvent and the residual oil was dissolved in methylene dichloride. The resulting solution was washed successively with 0.5N sodium hydroxide solution, water, and finally 0.5N hydrochloric acid. The washed solution was distilled under reduced pressure to give 1-dipropylcarbamoyl-3-ethylthio-1,2,4-triazole, b.p. 130°C./0.5 mm. Elemental analysis satisfactory.

EXAMPLE 41

A solution of 35.75 g. 3-propylthio-1,2,4-triazole in 150 ml. dry tetrahydrofuran was added dropwise to a stirred suspension of sodium hydride in mineral oil (14.4 g. of 50% suspension; 7.2 g. sodium hydride). The resulting mixture was refluxed with stirring for 1 hour. Heating was discontinued, and 40.9 g. dipropylcarbamoyl chloride was added dropwise to the stirred mixture, causing the evolution of heat with consequent refluxing. The reaction mixture was refluxed with stirring overnight, cooled, and filtered to remove sodium chloride formed in the reaction. The filtrate was distilled under reduced pressure to remove solvent, and the residual oil was dissolved in methylene dichloride. The resulting solution was washed successively with 0.5N sodium hydroxide solution, water, and finally 0.5N hydrochloric acid. The washed solution was distilled under pressure to give 1-dipropylcarbamoyl-3-propylthio-1,2,4-triazole, b.p. 118° – 120°C./0.1 mm. Elemental analysis satisfactory.

EXAMPLE 42

A solution of 51.6 g. 3-ethylthio-1,2,4-triazole and 31.6 g. dry pyridine in 100 ml. dry tetrahydrofuran was added dropwise to 200 ml. of a 10% w/v solution of phosgene in dry tetrahydrofuran (20 g. phosgene, 0.5 molecular proportion) with stirring and cooling to maintain the reaction temperature at 25° – 30°C. The mixture was stirred at 25° – 30°C. for a further period of 0.5 hour, and was then filtered to remove pyridine hydrochloride formed in the reaction. To the resulting solution of 1,1'-carbonylbis(3-ethylthio-1,2,4-triazole) was added dropwise with stirring a solution of 20.2 g. dipropylamine in 50 ml. dry tetrahydrofuran. The mixture was stirred for a further period of 0.5 hour, and was then evaporated under reduced pressure to remove solvent. The residual oil was dissolved in methylene dichloride and the resulting solution was washed successively with 0.5N sodium hydroxide solution, water, and finally 0.5N hydrochloric acid. The washed solution was distilled under reduced pressure to give 1-dipropylcarbamoyl-3-ethylthio-1,2,4-triazole, b.p. 130° - 132°C./0.5 mm. Elemental analysis satisfactory.

EXAMPLE 43

A solution of 13.5 g. 1-dipropylcarbamoyl-3-propylthio-1,2,4-triazole and 100 vol. hydrogen peroxide solution (5.7 ml., 1.0 molecular proportion) in 450 ml. glacial acetic acid was kept at room temperature for 14 days. The resulting solution was evaporated to dryness under reduced pressure and the residual oil was dissolved in methylene dichloride. The resulting solution was washed successively with 0.5N sodium hydroxide solution, and 0.5N hydrochloric acid. Solvent was removed from the solution by distillation under reduced pressure to give a residual oil which solidified in cooling. The solid product was recrystallized from benzene/petroleum ether, b.p. 40° - -dipropylcarbomyl- 60°C., to give 1-dipropylcarbamqyl-3-propylsulphinyl-1,2,4-triazole, m.p. 51° - 52.5°C. Elemental analysis satisfactory.

EXAMPLE 44

To a solution of 13.5 g. 1-dipropylcarbamoyl-3-propylthio-1,2,4-triazole in 150 ml. glacial acetic acid was added a 58% w/v solution of peracetic acid in glacial acetic acid (16.5 ml., 2.5 molecular proportions). The resulting mixture was heated at 100°C. for 3 hours, and then the acetic acid was removed by distillation under reduced pressure. The residue was dissolved in methylene dichloride and the resulting solution worked up as described in Example 43 to give 1-dipropylcarbamoyl-3-propylsulphonyl-1,2,4-triazole, m.p. 79° - 80°C. (from benzene/petroleum ether, b.p. 40° - 60°C.). Elemental analysis satisfactory.

EXAMPLE 45

In an analogous manner to that described in Example 30, there was prepared 1-diethylcarbamoyl-3-n-pentylthio-1,2,4-triazole, b.p. 140° - 144°C./0.1 mm. (97.0% 1-isomer by GLC assay.). Elemental analysis satisfactory.

EXAMPLE 46

In an analogous manner to that described in Example 37, the following compounds were prepared.
  1-diallylcarbamoyl-3-(but-2-enylthio)-1,2,4-triazole, b.p. 143° - 145°C./0.3 mm. (94.6% 1-isomer by GLC assay). Elemental analysis satisfactory.
  1-dipropylcarbamoyl-3-(but-2-enylthio)-1,2,4-triazole, b.p. 128° - 130°C./0.1 mm. (85.8% 1-isomer by GLC assay). Elemental analysis satisfactory.
  The intermediate 3-(but-2-enylthio)-1,2,4-triazole, m.p. 57° - 60°C., used in the above preparations was prepared from 3-mercapto-1,2,4-triazole in an analogous manner to that described in Example 1.

EXAMPLE 47

In an analogous manner to that described in Example 1, the following compounds of formula I were prepared.
  1-(N-ethyl-N-butylcarbamoyl)-3-propylsulphonyl-1,2,4-triazole, m.p. 55° - 56°C.
  1-(N-ethyl-N-butylcarbamoyl)-3-butylsulphonyl-1,2,4-triazole, m.p. 35°C.
  1-(N-ethyl-N-propylcarbamoyl)-3-isobutylsulphonyl-1,2,4-triazole, m.p. 57° - 57.5°C.
  1-(N-ethyl-N-propylcarbamoyl)-3-butylsulphonyl-1,2,4-triazole, m.p. 30°C.
  1-(N-ethyl-N-propylcarbamoyl)-3-isopropylsulphonyl-1,2,4-triazole, m.p. 44° - 44.5°C.
  1-(N-ethyl-N-propylcarbamoyl)-3-propylsulphonyl-1,2,4-triazole, m.p. 47.5° - 48°C.
  1-(N-allyl-N-propylcarbamoyl)-3-isobutylsulphonyl-1,2,4-triazole, an oil, $n_D^{22}$ 1.5108 (99.9% 1-isomer by GLC assay)
  1-(N-allyl-N-propylcarbamoyl)-3-butylsulphonyl-1,2,4-triazole, an oil, $n_D^{22}$ 1.5070
  1-(N-allyl-N-propylcarbamoyl)-3-propylsulphonyl-1,2,4-triazole, m.p. 39° - 40°C.
  1-(N-allyl-N-propylcarbamoyl)-3-isopropylsulphonyl-1,2,4-triazole, an oil, $n_D^{22}$ 1.5108 (97.9% 1-isomer by GLC assay)
  1-diethylcarbamoyl-3-sec.butylsulphonyl-1,2,4-triazole, an oil, $n_D^{26}$ 1.5045 (98.1% 1-isomer by GLC assay)
  1-(N-ethyl-N-isopropylcarbamoyl)-3-butylsulphonyl-1,2,4-triazole, an oil, $n_D^{22}$ 1.5010 (95.6% 1-isomer by GLC assay)
  1-(N-allyl-N-isopropylcarbamoyl)3-isobutylsulphonyl-1,2,4-triazole, an oil, $n_D^{22}$ 1.5065 (98.9% 1-isomer by GLC assay)
  1-(N-ethyl-N-isopropylcarbamoyl)-3-isobutylsulphonyl-1,2,4-triazole, m.p. 43° - 44 C.
  1-(N-allyl-N-isopropylcarbamoyl)-3-butylsulphonyl-1,2,4-triazole, an oil $n_D^{22}$ 1.5072 (97.9% 1-isomer by GLC assay)
  1-(N-allyl-N-isopropylcarbamoyl)-3-propylsulphonyl-1,2,4-triazole, an oil $n_D^{22}$ 1.5109 (98.3% 1-isomer by GLC assay)
  1-(N-allyl-N-isopropylcarbamoyl)-3-isopropylsulphonyl-1,2,4-triazole, m.p. 51.5° - 52°C.
  1-(N-ethyl-N-isopropylcarbamoyl)-3-isopropylsulphonyl-1,2,4-triazole, an oil, $n_D^{22}$ 1.5047 (96.1% 1-isomer by GLC assay)
  1-(N-ethyl-N-isopropylcarbamoyl)-3-propylsulphonyl-1,2,4-triazole, an oil, $n_D^{22}$ 1.5038 (93.8% 1-isomer by GLC assay)
  1-(N-ethyl-N-isopropylcarbamoyl)-3-ethylsulphonyl-1,2,4-triazole, an oil, $n_D^{22}$ 1.5078 (93.5% 1-isomer by GLC assay)
  1-(N-allyl-N-ethylcarbamoyl)-3-isopropylsulphonyl-1,2,4-triazole, an oil, $n_D^{26}$ 1.5128 (99.4% 1-isomer by GLC assay)
  1-(N-allyl-N-ethylcarbamoyl)-3-butylsulphonyl-1,2,4-triazole, m.p. 50° - 52°C.
  1-(N-ethyl-N-hexylcarbamoyl)-3-propylsulphonyl-1,2,4-triazole, m.p. 69° - 71°C.
  1-(N-ethyl-N-hexylcarbamoyl)-3-isopropylsulphonyl-1,2,4-triazole, an oil, $n_D^{26}$ 1.4934 (96.0% 1-isomer by GLC assay)
  1-(N-allyl-N-ethylcarbamoyl)-3-propylsulphonyl-1,2,4-triazole, m.p. 46° - 48°C.
  1-(N-ethyl-N-hexylcarbamoyl)-3-butylsulphonyl-1,2,4-triazole, m.p. 58° - 60°C.
  1-(N-allyl-N-isopropylcarbamoyl)-3-ethylsulphonyl-1,2,4-triazole, an oil, $n_D^{22}$ 1.5147 (96.7% 1-isomer by GLC assay)
  1-(N-propyl-N-prop-2-ynylcarbamoyl)-3-isopropylsulphonyl-1,2,4-triazole, m.p. 68.5° - 69°C.

1-(N-propyl-N-prop-2-ynylcarbamoyl)-3-butylsulphonyl-1,2,4-triazole, an oil, $n_D^{25}$ 1.5143 (97.0% 1-isomer by GLC assay)

1-(N-propyl-N-prop-2-ynylcarbamoyl)-3-isobutylsulphonyl-1,2,4-triazole, an oil, $n_D^{22}$ 1.5108 (98.3% 1-isomer by GLC assay)

1-(N-propyl-N-prop-2-ynylcarbamoyl)-3-propylsulphonyl-1,2,4-triazole, m.p. 49° – 50°C.

1-(N-propyl-N-1-methylbutylcarbamoyl)-3-propylsulphonyl-1,2,4-triazole, m.p. 55° – 58°C.

1-(N-ethyl-N-hexylcarbamoyl)-3-isobutylsulphonyl-1,2,4-triazole, m.p. 55° – 57°C.

1-(N-ethyl-N-isopentylcarbamoyl)-3-isobutylsulphonyl-1,2,4-triazole, an oil, $n_D^{22}$ 1.4928

1-(N-ethyl-N-isopentylcarbamoyl)-3-butylsulphonyl-1,2,4-triazole, an oil, $n_D^{22}$ 1.4955

1-(N-ethyl-N-isopentylcarbamoyl)-3-propylsulphonyl-1,2,4-triazole, an oil, $n_D^{22}$ 1.4989

1-(N-propyl-N-pentylcarbamoyl)-3-isobutylsulphonyl-1,2,4-triazole, m.p. 45° – 46°C.

1-(N-propyl-N-pentylcarbamoyl)-3-butylsulphonyl-1,2,4-triazole, m.p. 65° – 66°C., 1-(N-propyl-N-pentylcarbamoyl)-3-propylsulphonyl-1,2,4-triazole, an oil, $n_D^{22}$ 1.4946

1-(N-propyl-N-sec.butylcarbamoyl)-3-butylsulphonyl-1,2,4-triazole, an oil, $n_D^{22}$ 1.4975

1-(N-propyl-N-sec.butylcarbamoyl)-3-propylsulphonyl-1,2,4-triazole, an oil, $n_D^{22}$ 1.5005

1-(N-allyl-N-butylcarbamoyl)-3-butylsulphonyl-1,2,4-triazole, an oil, $n_D^{22}$ 1.5048

1-(N-allyl-N-butylcarbamoyl)-3-propylsulphonyl-1,2,4-triazole, an oil, $n_D^{22}$ 1.5063

1-(N-propyl-N-isopropylcarbamoyl)-3-butylsulphonyl-1,2,4-triazole, an oil, $n_D^{22}$ 1.4998

1-(N-propyl-N-isopropylcarbamoyl)-3-propylsulphonyl-1,2,4-triazole, an oil, $n_D^{22}$ 1.5012

1-(N-ethyl-N-isobutylcarbamoyl)-3-butylsulphonyl-1,2,4-triazole, an oil, $n_D^{22}$ 1.4996

1-(N-ethyl-N-isobutylcarbamoyl)-3-propylsulphonyl-1,2,4-triazole, m.p. 40° – 42°C.

1-(N-allyl-N-isobutylcarbamoyl)-3-propylsulphonyl-1,2,4-triazole, an oil, $n_D^{22}$ 1.5047

1-(N-propyl-N-1-methylbutylcarbamoyl)-3-isopropylsulphonyl-1,2,4-triazole, an oil, $n_D^{22}$ 1.4952 (90.6% 1-isomer by GLC assay)

1-(N-propyl-N-1-methylbutylcarbamoyl)-3-butylsulphonyl-1,2,4-triazole, an oil, $n_D^{26}$ 1.4926 (93.1% 1-isomer by GLC assay)

1-(N-allyl-N-prop-2-ynylcarbamoyl)-3-ethylsulphonyl-1,2,4-triazole, m.p. 63° – 64°C.

1-(N-allyl-N-prop-2-ynylcarbamoyl)-3-propylsulphonyl-1,2,4-triazole, an oil, $n_D^{22}$ 1.5250 (95.7% 1-isomer by GLC assay)

1-(N-allyl-N-prop-2-ynylcarbamoyl)-3-isopropylsulphonyl-1,2,4-triazole, m.p. 64° – 64.5°C.

1-(N-allyl-N-prop-2-ynylcarbamoyl)-3-butylsulphonyl-1,2,4-triazole, m.p. 46° – 46.5°C.

1-(N-allyl-N-prop-2-ynylcarbamoyl)-3-isobutylsulphonyl-1,2,4-triazole, an oil, $n_D^{22}$ 1.5208 (96.9% 1-isomer by GLC assay)

1-(N-propyl-N-pentylcarbamoyl)-3-isobutylsulphonyl-1,2,4-triazole, an oil, $n_D^{26}$ 1.4878 (86.8% 1-isomer by GLC assay)

1-(N-propyl-N-pentylcarbamoyl)-3-butylsulphonyl-1,2,4-triazole, m.p. 64° – 66°C.

1-(N-propyl-N-pentylcarbamoyl)-3-isopropylsulphonyl-1,2,4-triazole, an oil, $n_D^{26}$ 1.4914 (96.7% 1-isomer by GLC assay)

1-(N-propyl-N-pentylcarbamoyl)-3-propylsulphonyl-1,2,4-triazole, an oil, $n_D^{26}$ 1.4906 (93.7% 1-isomer by GLC assay)

1-(N-propyl-N-butylcarbamoyl)-3-isobutylsulphonyl-1,2,4-triazole, m.p. 43° – 45°C.

1-(N-propyl-N-butylcarbamoyl)-3-butylsulphonyl-1,2,4-triazole, an oil, $n_D^{26}$ 1.4922 (98.7% 1-isomer by GLC assay)

1-(N-propyl-N-butylcarbamoyl)-3-isopropylsulphonyl-1,2,4-triazole, an oil, $n_D^{26}$ 1.4958 (99.2% 1-isomer by GLC assay)

1-(N-propyl-N-butylcarbamoyl)-3-propylsulphonyl-1,2,4-triazole, m.p. 58° – 60°C.

1-(N-propyl-N-1-methylbutyl carbamoyl)-3-isobutylsulphonyl-1,2,4-triazole, an oil, $n_D^{26}$ 1.4916 (88.2% 1-isomer by GLC assay)

1-(N-allyl-N-pentylcarbamoyl)-3-propylsulphonyl-1,2,4-triazole, an oil, $n_D^{26}$ 1.5006 (97.7% 1-isomer by GLC assay)

1-(N-allyl-N-pentylcarbamoyl)-3-isopropylsulphonyl-1,2,4-triazole, an oil, $n_D^{26}$ 1.5022 (98.0% 1-isomer by GLC assay)

1-(N-allyl-N-pentylcarbamoyl-3-butylsulphonyl-1,2,4-triazole, an oil, $n_D^{26}$ 1.4992 (98.4% 1-isomer by GLC assay)

1-(N-allyl-N-pentylcarbamoyl)-3-isobutylsulphonyl-1,2,4-triazole, an oil, $n_D^{26}$ 1.4984 (97.4% 1-isomer by GLC assay)

1-(N-ethyl-N-pentylcarbamoyl)-3-isobutylsulphonyl-1,2,4-triazole, m.p. 65° – 67°C.

1-(N-ethyl-N-pentylcarbamoyl)-3-butylsulphonyl-1,2,4-triazole, m.p. 51° – 54°C.

1-(N-ethyl-N-pentylcarbamoyl)-3-isopropylsulphonyl-1,2,4-triazole, an oil, $n_D^{26}$ 1.4986

1-(N-ethyl-N-pentylcarbamoyl)-3-propylsulphonyl-1,2,4-triazole, m.p. 48.5° – 50.5°C.

1-(N-allyl-N-hexylcarbamoyl)-3-isobutylsulphonyl-1,2,4-triazole, an oil, $n_D^{26}$ 1.4964 (96.7% 1-isomer by GLC assay)

1-(N-allyl-N-hexylcarbamoyl)-3-butylsulphonyl-1,2,4-triazole, an oil, $n_D^{26}$ 1.4976 (98.4% 1-isomer by GLC assay)

1-(N-allyl-N-hexylcarbamoyl)-3-isopropylsulphonyl-1,2,4-triazole, an oil, $n_D^{26}$ 1.5004 (98.5% 1-isomer by GLC assay)

1-(N-allyl-N-hexylcarbamoyl)-3-propylsulphonyl-1,2,4-triazole, an oil, $n_D^{26}$ 1.4984 (97.3% 1-isomer by GLC assay)

1-(N-ethyl-N-cyclohexylcarbamoyl)-3-butylsulphonyl-1,2,4-triazole, m.p. 57° – 60°C.

1-(N-ethyl-N-cyclohexylcarbamoyl)-3-propylsulphonyl-1,2,4-triazole, m.p. 56° – 59°C.

1-(N-ethyl-N-cyclohexylcarbamoyl)-3-ethylsulphonyl-1,2,4-triazole, an oil, $n_D^{26}$ 1.5208 (88.0% 1-isomer by GLC assay)

1-(N-ethyl-N-allylcarbamoyl)-3-sec.butylsulphonyl-1,2,4-triazole, m.p. 32° – 33°C.

1-(N-propyl-N-prop-2-ynylcarbamoyl)-3-sec.butylsulphonyl-1,2,4-triazole, m.p. 59° —60°C.

1-(N-hexyl-N-allylcarbamoyl)-3-sec.butylsulphonyl-1,2,4-triazole, m.p. 45° – 46°C.

1-(N-butyl-N-propylcarbamoyl)-3-sec.butylsulphonyl-1,2,4-triazole, m.p. 50° – 51°C.

1-di-isopropylcarbamoyl-3-sec.butylsulphonyl-1,2,4-triazole, m.p. 85° – 87°C.

1-(N-ethyl-N-butylcarbamoyl)-3-sec.butylsulphonyl-1,2,4-triazole, an oil, $n_D^{20}$ 1.4995

1-(N-allyl-N-propylcarbamoyl)-3-sec.butylsulphonyl-1,2,4-triazole, m.p. 47° – 48°C.
1-diethylcarbamoyl-3-t. butylsulphonyl-1,2,4-triazole, m.p. 117° – 118°C.
1-diallylcarbamoyl-3-t. butylsulphonyl-1,2,4-triazole, m.p. 79° – 80°C.
1-(N-allyl-N-propylcarbamoyl)-3-t.butylsulphonyl-1,2,4-triazole, m.p. 78° – 79°C.
1-(N-ethyl-N-butylcarbamoyl)-3-t.butylsulphonyl-1,2,4-triazole, m.p. 71° – 72°C.
1-(N-allyl-N-ethylcarbamoyl)-3-t.butylsulphonyl-1,2,4-triazole, m.p. 79° – 80°C.
1-(N-ethyl-N-prop-2-ynylcarbamoyl)-3-propylsulphonyl-1,2,4-triazole, m.p. 70° – 73°C.
1-(N-ethyl-N-prop-2-ynylcarbamoyl)-3-butylsulphonyl-1,2,4triazole, m.p. 70° – 72°C.
1-(N-ethyl-N-prop-2-ynylcarbamoyl)-3-isobutylsulphonyl-1,2,4-triazole, m.p. 87° – 88°C.
1-(N-ethyl-N-prop-2-ynylcarbamoyl)-3-ethylsulphonyl-1,2,4-triazole, m.p. 57° – 58°C.
1-(N-ethyl-N-isopropylcarbamoyl)-3-pentylsulphonyl-1,2,4-triazole, an oil, $n_D^{21}$ 1.5014 (95.8% 1-isomer by GLC assay)
1-(N-ethyl-N-isopropylcarbamoyl)-3-sec.butylsulphonyl-1,2,4-triazole, an oil, $n_D^{21}$ 1.5045 (96.1% 1-isomer by GLC assay)
1-(N-propyl-N-isopropylcarbamoyl)-3-isobutylsulphonyl-1,2,4-triazole, an oil, $n_D^{21}$ 1.5032 (95.2% 1-isomer by GLC assay)
1-(N-propyl-N-isopropylcarbamoyl)-3-isobutylsulphonyl-1,2,4-triazole, m.p. 61° – 63°C.
1-(N-propyl-N-isopropylcarbamoyl)-3-sec.butylsulphonyl-1,2,4-triazole, m.p. 68° – 70°C.
1-(N-propyl-N-isopropylcarbamoyl)-3-pentylsulphonyl-1,2,4-triazole, m.p. 54.5° – 56.5°C.
1-(N-propyl-N-prop-2-ynylcarbamoyl)-3-pentylsulphonyl-1,2,4-triazole, an oil $n_D^{25}$ 1.5102 (93.4% 1-isomer by GLC assay
1-(N-ethyl-N-prop-2-ynylcarbamoyl)-3-sec.butylsulphonyl-1,2,4-triazole, m.p. 62° – 65°C.
1-(N-propyl-N-sec.butylcarbamoyl)-3-isobutylsulphonyl-1,2,4-triazole, m.p. 35° – 38°C.
1-(N-propyl-N-sec.butylcarbamoyl)-3-pentylsulphonyl-1,2,4-triazole, m.p. 38° – 40°C.
1-(N-ethyl-N-prop-2-ynylcarbamoyl)-3-pentylsulphonyl-1,2,4-triazole, m.p. 47° – 50°C.
1-(N-ethyl-N-prop-2-ynylcarbamoyl)-3-isopropylsulphonyl-1,2,4-triazole, m.p. 90° – 91.5°C.
1-(N-propyl-N-sec.butylcarbamoyl)-3-isopropylsulphonyl-1,2,4-triazole, m.p. 39° – 41°C.
1-(N-propyl-N-sec.butylcarbamoyl)-3-sec.butylsulphonyl-1,2,4-triazole, m.p. 40° – 41°C.
1-(N-ethyl-N-allylcarbamoyl)-3-isobutylsulphonyl-1,2,4-triazole, m.p. 67° – 69°C.
1-(N-ethyl-N-sec.butylcarbamoyl)-3-isobutylsulphonyl-1,2,4-triazole, m.p. 39° – 40.5°C.
1-(N-ethyl-N-sec.butylcarbamoyl)-3-butylsulphonyl-1,2,4-triazole, m.p. 25°C.
1-(N-ethyl-N-butylcarbamoyl)-3-isopropylsulphonyl-1,2,4-triazole, an oil, $n_D^{26}$ 1.5010 (98.1% 1-isomer by GLC assay)
1-(N-ethyl-N-butylcarbamoyl)-3-isobutylsulphonyl-1,2,4-triazole, m.p. 58° – 60°C.
1-(N-ethyl-N-butylcarbamoyl)-3-pentylsulphonyl-1,2,4-triazole, an oil, $n_D^{26}$ 1.4970 (98.6% 1-isomer by GLC assay)
1-(N-allyl-N-ethylcarbamoyl)-3-pentylsulphonyl-1,2,4-triazole, an oil, $n_D^{26}$ 1.5080 (98.7% 1-isomer by GLC assay)
1-(N-allyl-N-hexylcarbamoyl)-3-pentylsulphonyl-1,2,4-triazole, an oil, $n_D^{26}$ 1.5003 (99.4% 1-isomer by GLC assay)
1-(N-allyl-N-propylcarbamoyl)-3-pentylsulphonyl-1,2,4-triazole, an oil, $n_D^{22}$ 1.5059 (99.6% 1-isomer by GLC assay)
1-(N-allyl-N-ethylcarbamoyl)-3-isobutylsulphonyl-1,2,4-triazole, m.p. 67° – 69°C.
1-(N-ethyl-N-isobutylcarbamoyl)-3-isobutylsulphonyl-1,2,4-triazole, m.p. about 25°C.
1-(N-ethyl-N-pentylcarbamoyl)-3-pentylsulphonyl-1,2,4-triazole, m.p. about 25°C.
1-(N-ethyl-N-pentylcarbamoyl)-3-ethylsulphonyl-1,2,4-triazole, m.p. about 25°C.
1-N-di(2-methylallyl)carbamoyl-3-isobutylsulphonyl-1,2,4-triazole, an oil, $n_D^{22}$ 1.5130 (99.5% 1-isomer by GLC assay)
1-N-di(2-methylallyl)carbamoyl-3-pentylsulphonyl-1,2,4-triazole, an oil, $n_D^{22}$ 1.5113 (99.4% 1-isomer by GLC assay)
1-(N-butyl-N-allylcarbamoyl)-3-pentylsulphonyl-1,2,4-triazole, an oil, $n_D^{26}$ 1.5003 (95% 1-isomer by GLC assay)
1-(N-allyl-N-butylcarbamoyl)-3-sec.butylsulphonyl-1,2,4-triazole, an oil, $n_D^{26}$ 1.5040 (95% 1-isomer by GLC assay)
1-(N-allyl-N-butylcarbamoyl)-3-sec.butylsulphonyl-1,2,4-triazole, an oil, $n_D^{26}$ 1.5025 (95.7% 1-isomer by GLC assay)
1-(N-allyl-N-butylcarbamoyl)-3-isopropylsulphonyl-1,2,4-triazole, an oil, $n_D^{25}$ 1.5076 (95.1% 1-isomer by GLC assay)
1-(N-allyl-N-isopropylcarbamoyl)-3-pentylsulphonyl-1,2,4-triazole, an oil, $n_D^{26}$ 1.5058 (97.8% 1-isomer by GLC assay)
1-(N-allyl-N-isopropylcarbamoyl)-3-sec.butylsulphonyl-1,2,4-triazole, an oil, $n_D^{26}$ 1.5076 (96.9% 1-isomer by GLC assay)
1-N-di(2-methylallyl)carbamoyl-3-butylsulphonyl-1,2,4-triazole, an oil, $n_D^{22}$ 1.5118 (99.3% 1-isomer by GLC assay)
1-N-di(2-methylallyl)carbamoyl-3-propylsulphonyl-1,2,4-triazole, an oil, $n_D^{22}$ 1.5152
-N-di(2-methylallyl)carbamoyl-3-isopropylsulphonyl-1,2,4-triazole, an oil, $n_D^{22}$ 1.5163 (98.6% 1-isomer by GLC assay)
1-(N-ethyl-N-hexylcarbamoyl)-3-pentylsulphonyl-1,2,4-triazole, m.p. 56° – 57°C.
1-(N-ethyl-N-hexylcarbamoyl)-3-sec.butylsulphonyl-1,2,4-triazole, an oil, $n_D^{22}$ 1.4966 (95.8% 1-isomer by GLC assay)
1-(N-allyl-N-isobutylcarbamoyl)-3-isopropylsulphonyl-1,2,4-triazole, an oil, $n_D^{26}$ 1.5075 (99.6% 1-isomer by GLC assay)
1-(N-allyl-N-isobutylcarbamoyl)-3-butylsulphonyl-1,2,4-triazole, an oil, $n_D^{26}$ 1.5046 (99.2% 1-isomer by GLC assay)
1-(N-allyl-N-isobutylcarbamoyl)-3-isobutylsulphonyl-1,2,4-triazole, an oil, $n_D^{26}$ 1.5036 (98.1% 1-isomer by GLC assay)
1-(N-allyl-N-isobutylcarbamoyl)-3-sec.butylsulphonyl-1,2,4-triazole, an oil, $n_D^{26}$ 1.5050 (98.3% 1-isomer by GLC assay)

1-(N-allyl-N-isobutylcarbamoyl)-3-pentylsulphonyl-1,2,4-triazole, an oil, $n_D^{26}$ 1.5002 (99.2% 1-isomer by GLC assay)

1-(N-allyl-N-pentylcarbamoyl)-3-pentylsulphonyl-1,2,4-triazole, an oil, $n_D^{22}$ 1.5006 (97.6% 1-isomer by GLC assay)

1-(N-allyl-N-pentylcarbamoyl)-3-sec.butylsulphonyl-1,2,4-triazole, an oil, $n_D^{22}$ 1.5042 (96.4% 1-isomer by GLC assay)

EXAMPLE 48

In an analogous manner to that described in Example 2, the following compounds of formula I were prepared.

1-(N-allyl-N-prop-2-ynylcarbamoyl)-3-ethylthio-1,2,4-triazole, b.p. 127° – 131°C./0.2 mm. (97.2% 1-isomer by GLC assay)

1-(N-allyl-N-isopropylcarbamoyl)-3-ethylthio-1,2,4-triazole, b.p. 117° – 119°C./0.2mm. (81.7% 1-isomer by GLC assay)

1-(N-ethyl-N-isopropylcarbamoyl)-3-ethylthio-1,2,4-triazole, b.p. 112° – 115°C./0.15 – 0.2 mm. (72.7% 1-isomer by GLC assay)

1-(N-allyl-N-prop-2-ynylcarbamoyl)-3-ethylthio-1,2,4-triazole, b.p. 125° – 127°C./0.11 mm. (96.0% 1-isomer by GLC assay)

1-diethylcarbamoyl-3-t.butylthio-1,2,4-triazole, b.p. 141° – 142°C./1.4 mm.

1-diallylcarbamoyl-3-t.butylthio-1,2,4-triazole, b.p. 124°C./0.2 mm. (97.4% 1-isomer by GLC assay)

1-(N-allyl-N-propylcarbamoyl)-3-t.butylthio-1,2,4-triazole, b.p 150° – 151°C./1.3 mm.

1-(N-ethyl-N-butylcarbamoyl)-3-t.butylthio-1,2,4-triazole, b.p. 161° – 162°C./2.7 mm. (93.4% 1-isomer by GLC assay)

EXAMPLE 49

A dispersible powder was prepared by grinding together a mixture of the following ingredients in a hammer mill.

|  | % w/w |
|---|---|
| 1-Dipropylcarbamoyl-3-propylsulphonyl-1,2,4-triazole | 25.0 |
| Sodium N-methyl-N-palmitoyltaurate | 6.0 |
| Sodium di-octylsulphosuccinate | 0.5 |
| Colloidal silicic acid | 25.0 |
| Kaolin | 43.5 |

Similar dispersible powders were prepared using the following active ingredients in place of the triazole compound in the above formulation.

1-dipropylcarbamoyl-3-n-butylsulphonyl-1,2,4-triazole 1-dipropylcarbamoyl-3-ethylsulphonyl-1,2,4-triazole 1-dipropylcarbamoyl-3-isopropylsulphonyl-1,2,4-triazole 1-dipropylcarbamoyl-3-sec.butylsulphonyl-1,2,4-triazole 1-diallylcarbamoyl-3-propylsulphonyl-1,2,4-triazole 1-diethylcarbamoyl-3-methylsulphonyl-1,2,4-triazole 1-diethylcarbamoyl-3-n-butylsulphinyl-1,2,4-triazole 1-(N-n-butyl-N-ethylcarbamoyl)-3-ethylsulphonyl-1,2,4-triazole 1-(N-propyl-N-prop-2-ynylcarbamoyl)-3-ethylsulphonyl-1,2,4-triazole 1-(N-ethyl-N-isobutylcarbamoyl)-3-ethylsulphonyl-1,2,4-triazole

EXAMPLE 50

An emulsifiable concentrate suitable for dilution with water to form an aqueous emulsion was prepared from the following ingredients.

|  | % w/w |
|---|---|
| 1-Diallylcarbamoyl-3-ethylthio-1,2,4-triazole | 20.0 |
| Calcium dodecylbenzenesulphonate | 2.5 |
| Nonylphenoxypolyethoxyethanel * | 2.5 |
| Xylene | to 100.0 |

* A nonylphenol-ethylene oxide condensate containing an average of 14 mols. ethylene oxide per mol. nonylphenol.

Similar emulsifiable concentrates were prepared in which the triazole compound in the above formulation was replaced by the following compounds.

1-dipropylcarbamoyl-3-n-butylsulphonyl-1,2,4-triazole 1-dipropylcarbamoyl-3-ethylsulphonyl-1,2,4-triazole 1-dipropylcarbamoyl-3-n-pentylsulphinyl-1,2,4-triazole 1-diallylcarbamoyl-3-propylsulphinyl-1,2,4-triazole 1-diallylcarbamoyl-3-ethylsulphonyl-1,2,4-triazole 1-diethylcarbamoyl-3-ethylthio-1,2,4-triazole 1-diallylcarbamoyl-3-n-butylsulphonyl-1,2,4-triazole 1-(N-allyl-N-isobutylcarbamoyl)-3-ethylsulphonyl-1,2,4-triazole 1-(N-allyl-N-isobutylcarbamoyl)-3-ethylsulphinyl-1,2,4-triazole 1-(N-propyl-N-sec.butylcarbamoyl)-3-ethylsulphonyl-1,2,4-triazole

EXAMPLE 51

Emulsifiable concentrates (A) and (B) were prepared as described in Example 48, containing the following compounds as active ingredients:

A. 1-diallylcarbamoyl-3-ethylthio-1,2,4-triazole

B. 1-dipropylcarbamoyl-3-ethylsulphonyl-1,2,4-triazole

Rice seedlings were transplanted into paddy plots previously seeded with barnyard grass. Five days later the plots were sprayed with aqueous emulsions prepared from the concentrates (A) and (B), at an application rate of active ingredient of 2lb./acre. The plots were flooded with water six days later and examined 35 days after spraying. No barnyard grass was observed in the plots sprayed with the aqueous emulsions described above, and no phytotoxic effect on the rice plants was observed. A growth of barnyard grass had occurred in control plots that had received no chemical treatment.

EXAMPLE 52

This Example illustrates the preparation of compounds of formula II.

A solution of 4.1 g. 3-(2-ethoxyethylsulphonyl)-1,2,4-triazole, 3.5 g. diallylcarbamoyl chloride and 4 ml. triethylamine in 40 ml. dry tetrahydrofuran was refluxed under anhydrous conditions for 15 hours. The cooled reaction mixture was filtered to remove triethylamine hydrochloride and the filtrate was evaporated to remove solvent. The residue was triturated with petroleum ether (b.p. 40° – 60°C.) to give a solid product. This product was collected and recrystallised from ether/petroleum ether b.p. 40° – 60°C. to give 1-diallyl-carbamoyl-3-(2-ethoxyethylsulphonyl)-1,2,4-triazole, m.p. 62° – 63°C. Elemental analysis satisfactory.

The novel intermediate triazole compounds used in the above preparation were prepared as follows. To a solution of 11.8 g. sodium in 350 ml. absolute ethanol was added 52.5 g. 1,2,4-triazole-3-thiol. To the resulting solution was added 84 g. 1-bromo-2-ethoxyethane and the resulting solution refluxed for 3 hours. The cooled reaction mixture was filtered, the filtrate was evaporated under reduced pressure to remove solvent, and the residue was dissolved in ether. The resulting solution was filtered, the filtrate was evaporated to remove solvent and the residue distilled under reduced pressure to give 3-(2-ethoxyethylthio)-1,2,4-triazole, b.p. 137°–145°C./0.3–0.5 mm. Elemental analysis satisfactory.

Hydrogen peroxide (33.6 ml. of 100 vol. solution) was added in small portions to a solution of 17.3 g. 3-(2-ethoxyethylthio)-1,2,4-triazole in 150 ml. glacial acetic acid, maintaining the temperature of the reaction mixture at 80° – 85°C. When the addition of hydrogen peroxide was complete, the temperature of the reaction mixture was maintained at 80° – 85°C. for an additional period of 2 hours. The reaction mixture was distilled under reduced pressure to remove acetic acid and the solid residue obtained was crystallized from ethyl acetate/petroleum ether, b.p. 40° – 60°C. to give 3-(2-ethoxyethylsulphonyl)-1,2,4-triazole, m.p. 91.5°–91.5° 92.5°C.

In an analogous manner to that described above, the following compounds were prepared:

1-dipropylcarbamoyl-3-(2-methoxyethylsulphonyl)-1,2,4-triazole, m.p. 76° – 77°C.
1-dipropylcarbamoyl-3-(2-ethoxyethylsulphonyl)-1,2,4-triazole, m.p. 51° – 52°C.
1-diallylcarbamoyl-3-(2-methoxyethylsulphonyl)-1,2,4-triazole, m.p. 47° – 47.5°C.
1-diallylcarbamoyl-3-(2-methoxyethylsulphinyl)-1,2,4-triazole, an oil, $n_D^{25}$ 1.5058

Novel intermediates 3-(2-methoxyethylthio)-1,2,4-triazole, m.p. 53° – 54°C.
3-(2-methoxyethylsulphonyl)-1,2,4-triazole, m.p. 80° – 82°C.

Satisfactory elemental analyses were obtained for all the above-mentioned products.

EXAMPLE 53

This Example illustrates the preparation of compounds of formula II.

A solution of 5.67 g. 3-isobutylsulphonyl-1,2,4-triazole, 5.46 g. N-ethyl-N-(2-methoxyethyl)carbamoyl chloride, 6 ml. triethylamine and 40 ml. dry tetrahydrofuran was kept at ambient temperature (20°C.) for 72 hours. The mixture was filtered to remove triethylamine hydrochloride and the filtrate was evaporated to give a residual oil. This oil was washed with petroleum ether, b.p. 40° – 60°C. (3 × 100 ml.) and then dissolved in ether. The ethereal solution was filtered to remove a trace of insoluble material and the filtrate was evaporated to give a residual oil which was kept at 100°C. in vacuo for 2 hours to remove all traces of volatile material. There was thus obtained 1-[N-ethyl-N-(2-methoxyethyl)carbamoyl]-3-isobutylsulphonyl-1,2,4-triazole as an oil, $n_D^{25}$ 1.4984.

In an analogous manner to that described above, the following compounds were prepared.

1-[N-propyl-N-(2-ethoxyethyl)carbamoyl]-3-propylsulphonyl-1,2,4-triazole, an oil, $n_D^{25}$ 1.4918
1-[N-propyl-N-(2-ethoxyethyl)carbamoyl]-3-isopropylsulphonyl-1,2,4-triazole, an oil, $n_D^{23}$ 1.4940
1[N-propyl-N-(2-ethoxyethyl)carbamoyl]-3-n-butylsulphonyl-1,2,4-triazole, an oil, $n_D^{23}$ 1.4906
1-[N-propyl-N-(2-ethoxyethyl)carbamoyl]-3-isobutylsulphonyl-1,2,4-triazole, an oil, $n_D^{23}$ 1.4906
1-[N-ethyl-N-(2-methoxyethyl)carbamoyl]-3-propylsulphonyl-1,2,4-triazole, an oil, $n_D^{24}$ 1.5008
1-[N-ethyl-N-(2-methoxyethyl)carbamoyl]-3-isopropylsulphonyl-1,2,4-triazole, an oil, $n_D^{24}$ 1.5020
1[N-ethyl-N-(2-methoxyethyl)carbamoyl]-3-n-butylsulphonyl-1,2,4-triazole, an oil, $n_D^{24}$ 1.4984
1-[N-propyl-N-(2-methoxyethyl)carbamoyl]-3-propylsulphonyl-1,2,4-triazole, m.p. 45° – 45.5°C.
1-[N-propyl-N-(2-methoxyethyl)carbamoyl]-3-isopropylsulphonyl-1,2,4-triazole, an oil, $n_D^{24}$ 1.4978
1-[N-propyl-N-(2-methoxyethyl)carbamoyl]-3-n-butylsulphonyl-1,2,4-triazole, an oil, $n_D^{24}$ 1.4960
1-[N-propyl-N-(2-methoxyethyl)carbamoyl]-3-isobutylsulphonyl-1,2,4-triazole, an oil, $n_D^{25}$ 1.4942
1-[N-ethyl-N-(2-ethoxyethyl)carbamoyl]-3-ethylsulphonyl-1,2,4-triazole, an oil, $n_D^{25}$ 1.5000
1-[N-ethyl-N-(2-ethoxyethyl)carbamoyl]-3-propylsulphonyl-1,2,4-triazole, an oil, $n_D^{25}$ 1.4960
1-[N-ethyl-N-(2-ethoxyethyl)carbamoyl]-3-isopropylsulphonyl-1,2,4-triazole, an oil, $n_D^{25}$ 1.4952
1-[N-ethyl-N-(2-ethoxyethyl)carbamoyl]-3-n-butylsulphonyl-1,2,4-triazole, an oil, $n_D^{25}$ 1.4918
1-[N-propyl-N-(2-methoxyethyl)carbamoyl]-3-ethylsulphonyl-1,2,4-triazole, an oil, $n_D^{24}$ 1.5005
1-[N-ethyl-N-(2-methoxyethyl)carbamoyl]-3-ethylsulphonyl-1,2,4-triazole, an oil, $n_D^{24}$ 1.5036
1-[N-ethyl-N-(3-ethoxypropyl)carbamoyl]-3-ethylsulphonyl-1,2,4-triazole, an oil, $n_D^{25}$ 1.4975
1-[N-propyl-N-(2-ethoxyethyl)carbamoyl]-3-ethylsulphonyl-1,2,4-triazole, an oil, $n_D^{22}$ 1.4956

Novel intermediate compounds used in the preparation described above were prepared as follows. N-ethyl-N-2-methoxyethylamine, b.p. 115° – 116°C., was prepared by reaction of 3 molecular proportions of ethylamine with 1 molecular proportion of 1-bromo-2-methoxyethane in aqueous solution containing 1 equivalent of sodium hydroxide at 30° – 50°C. To a stirred solution of 89.1 g. phosgene in 500 ml. dry ether at −20°C. was added a solution of 30.9 g. N-ethyl-N-2-methoxyethylamine in 50 ml. dry ether, maintaining the temperature of the reaction mixture at −20°C. The stirred mixture was then allowed to warm to room temperature during 1 hour. The reaction mixture was filtered and the filtrate evaporated in vacuo below 25°C. to remove the solvent and give the product, N-(2-methoxyethyl)-N-ethylcarbamoyl chloride as a pale yellow liquid.

The following novel intermediates were prepared in an analogous manner.

N-propyl-N-2-methoxyethylamine, b.p. 138°C.
N-propyl-N-(2-methoxyethyl)carbamoyl chloride
N-propyl-N-2-ethoxyethylamine, b.p. 154° – 155°C.
N-propyl-N-(2-ethoxyethyl)carbamoyl chloride
N-ethyl-N-2-methoxyethylamine, b.p. 116°C.
N-ethyl-N-(2-methoxyethyl)carbamoyl chloride
N-ethyl-N-3-ethoxypropylamine, b.p. 155°–156°C.
N-ethyl-N-(3-ethoxypropyl)carbamoyl chloride The following novel intermediates were prepared by a method analogous to that described in Example 52.

3-propylsulphonyl-1,2,4-triazole, m.p. 116° – 117°C.
3-isopropylsulphonyl-1,2,4-triazole, m.p. 170° – 171°C.
3-n-butylsulphonyl-1,2,4-triazole, m.p. 96° – 97°C.
3-isobutylsulphonyl-1,2,4-triazole, m.p. 157° – 158.5°C.
3-ethylsulphonyl-1,2,4-triazole, m.p. 145°C.

EXAMPLE 54

This Example illustrates the preparation of compounds of formula II.

A solution of 0.03 mole of 3-(2-methoxyethylsulphonyl)-1,2,4-triazole, 6 ml. of triethylamine and 0.033 mole of N-ethyl-N-isopropylcarbamoyl chloride in 40 ml. of dry tetrahydrofuran was heated under reflux for 15 hours. The cooled reaction mixture was filtered to remove triethylamine hydrochloride and the filtrate was evaporated to remove solvent. The product crystallized on cooling and treatment with 100 ml. of petroleum ether (b.p. 62°–68°C). This solid was collected and recrystallized from 100 ml. benzene/ petroleum ether (b.p. 40°–60°C) to give 1-(N-ethyl-N-isopropylcarbamoyl)-3-(2-methoxyethylsulphonyl)-1,2,4-triazole, m.p. 64°–65°C. Elemental analysis satisfactory.

The intermediate, 3-(2-methoxyethylsulphonyl)-1,2,4-triazole, was prepared by a method analogous to that described in Example 52.

The carbamoyl chloride intermediate was prepared in the following way. Phosgene was passed into 100 ml. of refluxing ethyl acetate until the liquid was saturated with phosgene. To the refluxing, stirred solution was added dropwise a solution of N-ethyl-isopropylamine in 100 ml. ethyl acetate. When the addition was complete the flow of phosgene into the stirred, refluxing reaction mixture was maintained for 30 minutes. The reaction mixture was distilled under reduced pressure to remove the solvent and give the product N-ethyl-N-isopropylcarbamoyl chloride.

In an analogous manner to that described above the following compounds were prepared:

1-dipropylcarbamoyl-3-(2-ethoxyethylsulphonyl)-1,2,4-triazole, m.p. 51° – 52°C.
1-diallylcarbamoyl-3-(2-ethoxyethylsulphonyl)-1,2,4-triazole, m.p. 62° – 63°C.
1-(N-butyl-N-ethylcarbamoyl)-3-(2-ethoxyethylsulphonyl)-1,2,4-triazole, b.p. 185° – 188°C./0.2 mm.
1-(N-allyl-N-propylcarbamoyl)-3-(2-ethoxyethylsulphonyl)-1,2,4-triazole, m.p. 51° – 52°C.
1-(N-propyl-N-2-propynylcarbamoyl)-3-(2-ethoxyethylsulphonyl)-1,2,4-triazole, m.p. 68° – 70°C.
1-(N-allyl-N-ethylcarbamoyl)-3-(2-methoxyethylsulphonyl)-1,2,4-triazole, m.p. 58.5° – 59.5°C.
1-(diethylcarbamoyl)-3-(2-methoxyethylsulphonyl)-1,2,4-triazole, m.p. 46° – 47°C.
1-(N-allyl-N-butylcarbamoyl)-3-(2-ethoxyethylsulphonyl)-1,2,4-triazole, b.p. 192° – 194°C./0.35 mm.
1-(N-allyl-N-butylcarbamoyl)-3-(2-methoxyethylsulphonyl)-1,2,4-triazole, m.p. 48° – 50°C.
1-(N-allyl-N-propylcarbamoyl)-3-(2-methoxyethylsulphonyl)-1,2,4-triazole, m.p. 60° – 61°C.
1-(diethylcarbamoyl)-3-(2-propoxyethylsulphonyl)-1,2,4-triazole, m.p. 57.5° – 58°C.
1-(diethylcarbamoyl)-3-(3-ethoxypropylsulphonyl)-1,2,4-triazole, an oil, $n_D^{21}$ 1.5012 (95.8% 1-isomer by GLC assay)
1-(N-ethyl-N-2-propynylcarbamoyl)-3-(2-methoxyethylsulphonyl)-1,2,4-triazole, m.p. 56° – 58°C.
1-(N-propyl-N-hexylcarbamoyl)-3-(2-ethoxyethylsulphonyl)-1,2,4-triazole, an oil, $n_D^{21}$ 1.4931 (98.4% 1-isomer by GLC assay)
1-(N-ethyl-N-isopropylcarbamoyl)-3-(2-methoxyethylsulphonyl)-1,2,4-triazole, m.p. 85° – 85.5°C.
1-(N-ethyl-N-isopropylcarbamoyl)-3-(2-ethoxyethylsulphonyl)-1,2,4-triazole, m.p. 64° – 65°C.
1-(N-propyl-N-2-propynylcarbamoyl)-3-(2-methoxyethylsulphonyl)-1,2,4-triazole, m.p. 61° – 63°C.
1-(N-propyl-N-isopropylcarbamoyl)-3-(2-methoxyethylsulphonyl)-1,2,4-triazole, m.p. 73.5° – 74.5 C.
1-(diallylcarbamoyl)-3-(3-ethoxypropylsulphonyl)-1,2,4-triazole, an oil, $n_D^{21}$ 1.5128 (97.2% 1-isomer by GLC assay)
1-(diallylcarbamoyl)-3-(2-propoxyethylsulphonyl)-1,2,4-triazole, m.p. 49° – 49.5°C.
1-(N-allyl-N-propylcarbamoyl)-3-(2-methoxyethylsulphonyl)-1,2,4-triazole, m.p. 55° – 55.5°C.
1-(N-propyl-N-sec.butylcarbamoyl)-3-(2-methoxyethylsulphonyl)-1,2,4-triazole, m.p. 42° – 44°C.
1-(N-ethyl-N-2-propynylcarbamoyl)-3-(2-ethoxyethylsulphonyl)-1,2,4-triazole, m.p. 81.5° – 83.5°C.
1-(N-propyl-N-sec.butylcarbamoyl)-3-(2-ethoxyethylsulphonyl)-1,2,4-triazole, m.p. 38° – 40.5°C.
1-(N-propyl-N-isopropylcarbamoyl)-3-(2-ethoxyethylsulphonyl)-1,2,4-triazole, m.p. 73.5° – 75.5°C.
1-(diallylcarbamoyl)-3-(2-butoxyethylsulphonyl)-1,2,4-triazole, an oil, $n_D^{26}$ 1.5082
1-(N-allyl-N-hexylcarbamoyl)-3-(2-methoxyethylsulphonyl)-1,2,4-triazole, an oil, $n_D^{22}$ 1.5031 (99% 1-isomer by GLC assay)
1-(N-allyl-N-hexylcarbamoyl)-3-(2-ethoxyethylsulphonyl)-1,2,4-triazole, an oil, $n_D^{22}$ 1.5016 (97.5% 1-isomer by GLC assay)
1-(N-propyl-N-sec.butylcarbamoyl)-3-(2-ethoxyethylsulphonyl)-1,2,4-triazole, m.p. 38° – 40.5°C.
1-(N-ethyl-N-butylcarbamoyl)-3-(2-methoxyethylsulphonyl)-1,2,4-triazole, an oil, $n_D^{26}$ 1.5006
1-(N-ethyl-N-hexylcarbamoyl)-3-(2-ethoxyethylsulphonyl)-1,2,4-triazole, m.p. 42° – 43°C.
1-(N-ethyl-N-hexylcarbamoyl)-3-(2-methoxyethylsulphonyl)-1,2,4-triazole, an oil, $n_D^{22}$ 1.4977 (96.3% 1-isomer by GLC assay)
1-(N-allyl-N-isobutylcarbamoyl)-3-(2-methoxyethylsulphonyl)-1,2,4-triazole, an oil, $n_D^{26}$ 1.5052
1-(N-allyl-N-isopropylcarbamoyl)-3-(2-methoxyethylsulphonyl)-1,2,4-triazole, m.p. 77° – 80°C.
1-(N-allyl-N-isopropylcarbamoyl)-3-(2-ethoxyethylsulphonyl)-1,2,4-triazole, m.p. 52° – 54°C.
1-(N-ethyl-N-pentylcarbamoyl)-3-(2-ethoxyethylsulphonyl)-1,2,4-triazole, m.p. 125°C.
1-(N-ethyl-N-pentylcarbamoyl)-3-(2-methoxyethylsulphonyl)-1,2,4-triazole, m.p. 25°C.

The following novel carbamoyl chloride and triazole intermediates were prepared:
3-(3-ethoxypropylsulphonyl)-1,2,4-triazole, m.p. 115° – 115.5°C.
3-(2-butoxyethylsulphonyl)-1,2,4-triazole, m.p. 101° – 102°C.
N-allyl-N-propylcarbamoyl chloride, b.p. 102° – 103°C./16–17 mm.
N-propyl-N-(2-propynyl)carbamoyl chloride, b.p. 56° – 60°C./0.25 mm.

N-allyl-N-ethylcarbamoyl chloride, b.p. 36°C./0.05 mm.
N-allyl-N-butylcarbamoyl chloride, b.p. 76°C./0.1 mm.
N-ethyl-N-(2-propynyl)carbamoyl chloride
N-propyl-N-(2-propynyl)carbamoyl chloride

EXAMPLE 55

This Example illustrates the preparation of compounds of formula II.

A solution of 0.03 mole of 3-propylsulphonyl-1,2,4-triazole, 11 ml. of triethylamine, 6.85 g. of N-butyl-N-(2-ethoxyethyl)carbamoyl chloride in 40 ml. of tetrahydrofuran was allowed to stand for 5½ days at room temperature. The reaction mixture was filtered to remove triethylamine hydrochloride and the filtrate was evaporated to remove solvent. The product was treated with 100 ml. of petroleum ether (b.p. 62° – 68°C.) and separated. It was a liquid at room temperature and it was then washed three times by decantation with petroleum ether (b.p. 40° – 60°C.). A solution of the product in methylene chloride was charcoaled, filtered and evaporated by heating in a vacuum on a steam bath for a period of two hours. GLC assay showed that the product, 1-[N-butyl-N-(2-ethoxyethyl)carbamoyl]-3-propylsulphonyl-1,2,4-triazole, contained 95.17% of the 1-isomer. Elemental analysis satisfactory.

The N-butyl-N-(2-ethoxyethyl)carbamoyl chloride used in the above reaction was prepared in an analogous way to that described in Example 53.

The 3-propylsulphonyl-1,2,4-triazole used in the above reaction was prepared as follows.

20.2 g. of 3-mercapto-1,2,4-triazole was added to a solution of 4.8 g. sodium in 150 ml. absolute ethanol. When dissolution was complete 24.6 g. propyl bromide was added. The stirred mixture was gradually heated to boiling under reflux, refluxed for 1 hour, cooled to room temperature and filtered. The filtrate was distilled to dryness under reduced pressure and the residue dissolved in ether. The resulting solution was filtered, dried over anhydrous sodium sulphate and distilled under reduced pressure to give 3-propylthio-1,2,4-triazole, b.p. 143° – 144°C./1 mm. This product solidified, m.p. 53° – 56°C.

To a solution of 14.3 g. 3-propylthio-1,2,4-triazole in 100 ml. glacial acetic acid was added 28.5 ml. 100 vol. hydrogen peroxide solution (2.5 molecular proportions). The solution was heated gradually to 95° – 100°C., kept at this temperature for 2 hours and then distilled to dryness under reduced pressure. The residue was recrystallized from toluene to give 3-propylsulphonyl-1,2,4-triazole, m.p. 116° – 117°C. Elemental analysis satisfactory.

The following compounds were prepared in an analogous manner to that described above:

1-[N-ethyl-N-(2-methoxyethyl)carbamoyl]-3-isobutylsulphonyl-1,2,4-triazole, an oil (97.3% 1-isomer by GLC assay) $n_D^{23}$ 1.5010
1-[N-ethyl-N-(2-ethoxyethyl)carbamoyl]-3-isobutylsulphonyl-1,2,4-triazole, an oil (90.2% 1-isomer by GLC assay) $n_D^{22}$ 1.4941
1-[N-allyl-N-(2-ethoxyethyl)carbamoyl]-3-ethylsulphonyl-1,2,4-triazole, an oil, $n_D^{22}$ 1.5071
1-[N-allyl-N-(2-ethoxyethyl)carbamoyl]-3-propylsulphonyl-1,2,4-triazole, an oil, $n_D^{22}$ 1.5039
1-[N-allyl-N-(2-ethoxyethyl)carbamoyl]-3-butylsulphonyl-1,2,4-triazole, an oil, $n_D^{22}$ 1.5014
1-[N-butyl-N-(2-ethoxyethyl)carbamoyl]-3-ethylsulphonyl-1,2,4-triazole, an oil (95.2% 1-isomer by GLC assay) $n_D^{22}$ 1.4978
1-[N-butyl-N-(2-ethoxyethyl)carbamoyl]-3-propylsulphonyl-1,2,4-triazole, an oil (96.8% 1-isomer by GLC assay) $n_D^{22}$ 1.4949
1-[N-butyl-N-(2-ethoxyethyl)carbamoyl]-3-butylsulphonyl-1,2,4-triazole, an oil (95.8% 1-isomer by GLC assay) $n_D^{22}$ 1.4930
1-[N-allyl-N-(2-methoxyethyl)carbamoyl]-3-ethylsulphonyl-1,2,4-triazole, an oil, $n_D^{24}$ 1.5112 (93.2% 1-isomer by GLC assay)
1-[N-allyl-N-(2-methoxyethyl)carbamoyl]-3-propylsulphonyl-1,2,4-triazole, an oil, $n_D^{24}$ 1.5075
1-[N-allyl-N-(2-methoxyethyl)carbamoyl]-3-butylsulphonyl-1,2,4-triazole, an oil, $n_D^{24}$ 1.5054
1-[N-allyl-N-(2-methoxyethyl)carbamoyl]-3-(2-ethoxyethylsulphonyl)-1,2,4-triazole, an oil, $n_D^{24}$ 1.5041 (83.3% 1-isomer by GLC assay)
1-[butyl-N-(2-methoxyethyl)carbamoyl]-3-ethylsulphonyl-1,2,4-triazole, an oil, $n_D^{19}$ 1.5020 (93.2% 1-isomer by GLC assay)
1-[N-butyl-N-(2-methoxyethyl)carbamoyl]-3-propylsulphonyl-1,2,4-triazole, an oil, $n_D^{19}$ 1.4992 (93.6% 1-isomer by GLC assay)
1-[N-butyl-N-(2-methoxyethyl)carbamoyl]-3-butylsulphonyl-1,2,4-triazole, an oil, $n_D^{19}$ 1.4961 (92.0% 1-isomer by GLC assay)
1-[N-butyl-N-(2-methoxyethyl)carbamoyl]-3-ethoxyethylsulphonyl-1,2,4-triazole, an oil, $n_D^{19}$ 1.4952 (90.6% 1-isomer by GLC assay)
1-[N-ethyl-N-(2-methoxyethyl)carbamoyl]-3-ethoxyethylsulphonyl-1,2,4-triazole, m.p. 51.5° – 52.5°C.
1-[N-allyl-N-(3-ethoxypropyl)carbamoyl]-3-ethylsulphonyl-1,2,4-triazole, an oil, $n_D^{21}$ 1.5101 (99.4% 1-isomer by GLC assay)
1-[N-allyl-N-(3-ethoxypropyl)carbamoyl]-3-propylsulphonyl-1,2,4-triazole, an oil, $n_D^{21}$ 1.5070 (94.9% 1-isomer by GLC assay)
1-[N-allyl-N-(3-ethoxypropyl)carbamoyl]-3-butylsulphonyl-1,2,4-triazole, an oil, $n_D^{21}$ 1.5042 (96.4% 1-isomer by GLC assay)
1-[N-ethyl-N-(2-propoxyethyl)carbamoyl]-3-ethylsulphonyl-1,2,4-triazole, an oil, $n_D^{21}$ 1.5010 (97.0% 1-isomer by GLC assay)
1-[N-ethyl-N-(2-propoxyethyl)carbamoyl]-3-propylsulphonyl-1,2,4-triazole, an oil, $n_D^{21}$ 1.4980 (97.4% 1-isomer by GLC assay)
1-[N-ethyl-N-(2-propoxyethyl)carbamoyl]-3-butylsulphonyl-1,2,4-triazole, an oil, $n_D^{21}$ 1.4973 (96.5% 1-isomer by GLC assay)
1-[N-ethyl-N-(2-propoxyethyl)carbamoyl]-3-(2-ethoxyethylsulphonyl)-1,2,4-triazole, an oil, $n_D^{21}$ 1.4966 (95.3% 1-isomer by GLC assay)
1-[N-propyl-N-(2-methoxyethyl)carbamoyl]-3-sec.-butylsulphonyl-1,2,4-triazole, m.p. 55.5° – 56.5°C.
1-[N-propyl-N-(2-methoxyethyl)carbamoyl]-3-pentylsulphonyl-1,2,4-triazole, an oil, $n_D^{21}$ 1.4970 (97.8% 1-isomer by GLC assay)
1-[N-propyl-N-(2-methoxyethyl)carbamoyl]-3-(2-methoxyethylsulphonyl)-1,2,4-triazole, an oil, $n_D^{21}$ 1.5021 (95.0% 1-isomer by GLC assay)
1-[N-ethyl-N-(2-ethoxyethyl)carbamoyl]-3-pentylsulphonyl-1,2,4-triazole, an oil, $n_D^{21}$ 1.5002 (92.1% 1-isomer by GLC assay)
1-[N-ethyl-N-(2-ethoxyethyl)carbamoyl]-3-(2-methoxyethylsulphonyl)-1,2,4-triazole, an oil, $n_D^{21}$ 1.4966 (96.5% 1-isomer by GLC assay)

1-[N-propyl-N-(2-methoxyethyl)carbamoyl]-3-(2-ethoxyethylsulphonyl)-1,2,4-triazole, an oil, $n_D^{21}$ 1.5004 (93.9% 1-isomer by GLC assay)

1-[N-propyl-N-(2-ethoxyethyl)carbamoyl]-3-(2-ethoxyethylsulphonyl)-1,2,4-triazole, m.p. 42° – 43.5°C.

1-[N-propyl-N-(2-ethoxyethyl)carbamoyl]-3-(2-methoxyethylsulphonyl)-1,2,4-triazole, an oil, $n_D^{22}$ 1.4990 (96.2% 1-isomer by GLC assay)

1-[N-propyl-N-(2-ethoxyethyl)carbamoyl]-3-pentylsulphonyl-1,2,4-triazole, an oil, $n_D^{22}$ 1.4948 (96.7% 1-isomer by GLC assay) 1-[N-ethyl-N-(3-ethoxypropyl)carbamoyl]-3-isopropylsulphonyl-1,2,4-triazole, an oil, $n_D^{23}$ 1.4960 (96.6% 1-isomer by GLC assay).

1-[N-ethyl-N-(3-ethoxypropyl)carbamoyl]-3-butylsulphonyl-1,2,4-triazole, an oil, $n_D^{23}$ 1.4978 (96.5% 1-isomer by GLC assay).

1-[N-ethyl-N-(3-ethoxypropyl)carbamoyl]-3-isobutylsulphonyl-1,2,4-triazole, an oil, $n_D^{25}$ 1.4958 (95.4% 1-isomer by GLC assay).

1-[N-ethyl-N-(3-ethoxypropyl)carbamoyl]-3-pentylsulphonyl-1,2,4-triazole, an oil, $n_D^{25}$ 1.4952 (98.3% 1-isomer by GLC assay).

1-[N-ethyl-N-(3-ethoxypropyl)carbamoyl]-3-propylsulphonyl-1,2,4-triazole, an oil, $n_D^{23}$ 1.4958 (94.2% 1-isomer by GLC assay).

1-[N-ethyl-N-(2-isopropoxyethyl)carbamoyl]-3-ethylsulphonyl-1,2,4-triazole, an oil, $n_D^{22}$ 1.4983 (98.5% 1-isomer by GLC assay).

1-[N-ethyl-N-(2-isopropoxyethyl)carbamoyl]-3-propylsulphonyl-1,2,4-triazole, an oil, $n_D^{22}$ 1.4958 (97.4% 1-isomer by GLC assay).

1-[N-ethyl-N-(2-isopropoxyethyl)carbamoyl]-3-butylsulphonyl-1,2,4-triazole, an oil, $n_D^{22}$ 1.4941 (95.9% 1-isomer by GLC assay).

1-[N-ethyl-N-(2-isopropoxyethyl)carbamoyl]-3-(2-ethoxyethylsulphonyl)-1,2,4-triazole, an oil, $n_D^{22}$ 1.4930 (83.8% 1-isomer by GLC assay). 1-[N-ethyl-(1-methyl-2-propoxyethyl)carbamoyl]-3-propylsulphonyl-1,2,4-triazole, an oil, $n_D^{22}$ 1.4940 (63.8% 1-isomer by GLC assay)

1-[N-ethyl-N-(1-methyl-2-propoxyethyl)carbamoyl]-3-butyl sulphonyl-1,2,4-triazole, an oil, $n_D^{22}$ 1.4930 (67.7% 1-isomer by GLC assay)

1-[N-ethyl-N-(3-methoxypropyl)carbamoyl]-3-ethylsulphonyl-1,2,4-triazole, an oil, $n_D^{22}$ 1.5021 (96.1% 1-isomer by GLC assay)

1-[N-ethyl-N-(3-methoxypropyl)carbamoyl]-3-propylsulphonyl-1,2,4-triazole, an oil, $n_D^{22}$ 1.4992 (96.8% 1-isomer by GLC assay)

1-[N-ethyl-N-(3-methoxypropyl)carbamoyl]-3-butylsulphonyl-1,2,4-triazole, an oil, $n_D^{22}$ 1.4974 (97.8% 1-isomer by GLC assay)

1-[N-ethyl-N-(3-methoxypropyl)carbamoyl]-3-(2-methoxyethylsulphonyl)-1,2,4-triazole, an oil, $n_D^{22}$ 1.5000 (98.0% 1-isomer by GLC assay)

1-(N-propyl-N-methoxymethylcarbamoyl)-3-propylsulphonyl-1,2,4-triazole, an oil, $n_D^{26}$ 1.5012 (93.9% 1-isomer by GLC assay)

1-(N-propyl-N-methoxymethylcarbamoyl)-3-sec.-butylsulphonyl-1,2,4-triazole, m.p. 55.5° – 56.5°C.

1-(N-methyl-N-methoxymethylcarbamoyl)-3-sec.-butylsulphonyl-1,2,4-triazole, an oil, $n_D^{23}$ 1.5160 (90.1% 1-isomer by GLC assay)

1-[N-ethyl-N-(2-allyloxyethyl)carbamoyl]-3-sec.-butylsulphonyl-1,2,4-triazole, an oil, $n_D^{22}$ 1.4983 (97.0% 1-isomer by GLC assay) 1-[N-allyl-N-(2-butoxyethyl)carbamoyl]-3-(2-ethoxyethylsulphonyl)-1,2,4-triazole, an oil, $n_D^{21}$ 1.4991 (96.3% 1-isomer by GLC assay).

Satisfactory elemental analyses were obtained for all of the compounds listed above.

The following novel carbamoyl chloride intermediates were prepared. All of these compounds were oils.

N-butyl-N-(2-ethoxyethyl)carbamoyl chloride
N-ethyl-N-(2-ethoxyethyl)carbamoyl chloride
N-allyl-N-(2-ethoxyethyl)carbamoyl chloride
N-allyl-N-(2-methoxyethyl)carbamoyl chloride
N-butyl-N-(2-methoxyethyl)carbamoyl chloride
N-allyl-N-(2-ethoxypropyl)carbamoyl chloride
N-ethyl-N-(2-propoxyethyl)carbamoyl chloride
N-ethyl-N-(2-allyloxyethyl)carbamoyl chloride
N-ethyl-N-(3-ethoxypropyl)carbamoyl chloride
N-ethyl-N-(2-isopropoxyethyl)carbamoyl chloride
N-ethyl-N-(1-methyl-2-propoxyethyl)carbamoyl chloride
N-ethyl-N-(3-methoxypropyl)carbamoyl chloride
N-propyl-N-methoxymethyl carbamoyl chloride
N-methyl-N-methoxymethyl carbamoyl chloride
N-allyl-N-(2-butoxyethyl)carbamoyl chloride
N-propyl-N-(2-methoxyethyl)carbamoyl chloride
N-propyl-N-(2-ethoxyethyl)carbamoyl chloride

EXAMPLE 56

This Example illustrates the preparation of compounds of formula II.

A solution of 7.4 g. 3-(2-allyloxyethylthio)-1,2,4-triazole, 8ml. triethylamine 6.0 g. diethylcarbamoyl chloride in 40 ml. of tetrahydrofuran was heated under reflux for 15 hours. The cooled reaction mixture was filtered to remove triethylamine hydrochloride and the filtrate was evaporated under vacuum to remove the solvent. Further precipitation of amine hydrochloride was filtered off. The filtrate was dissolved in 50 ml. methylene chloride and washed with ice-cold N/10 sodium hydroxide, with N/10 hydrochloric acid and finally with ice-cold water. The solvent was removed by vacuum distillation to give a liquid product, 1-diethylcarbamoyl-3-(2-allyloxyethylthio)-1,2,4-triazole, b.p. 148° – 153°C./0.05 mm. GLC assay showed that the 1-isomer was present to the extent of 98.33%. Elemental analysis was satisfactory.

The novel 3-(2-allyloxyethylthio)-1,2,4-triazole used in the above reaction was made as follows.

To a solution of 2.15 g. sodium in 70 ml. absolute ethanol was added 9.5 g. 1,2,4-triazole-3-thiol and the resulting mixture filtered to remove insoluble materials. After the addition of 18.2 g. 2-allyloxyethylbromide, the mixture was heated under reflux on a steam bath for 5 hours. Solvent was removed by vacuum distillation and the residue extracted with methylene chloride and filtered. The filtrate was distilled so as to remove the methylene chloride and to give an oily product, 3-(2-allyloxyethylthio)-1,2,4-triazole. GLC assay showed that the product was 95.4% pure. Elemental analysis was satisfactory.

The following compound was prepared in an analogous manner to that described above:

1-diallylcarbamoyl-3-(2-allyloxyethylthio)-1,2,4-triazole, an oil, $n_D^{24}$ 1.5406 (87.6% 1-isomer by GLC assay)

EXAMPLE 57

This Example illustrates the preparation of a compound of formula II.

6.75 g. of 3-(2-methoxyethylsulphinyl)-1,2,4-triazole was dissolved in 40 ml. dry tetrahydrofuran. To this solution was added 8 ml. of triethylamine causing the separation of a lower oily layer. After the addition of 6.75 g. diallyl carbamoyl chloride the mixture was refluxed for 2½ hours. The oil gradually disappeared as triethylamine hydrochloride was precipitated. The mixture was cooled and filtered to remove the triethylamine hydrochloride After evaporating the solvent it was found that the residual oil did not crystallize when treated with petroleum ether (b.p. 40° – 60°C.). It crystallized at 0°C. but melted again at room temperature. After washing with petrol by decantation the product was taken up in methylene chloride and filtered. Finally the methylene chloride was removed by vacuum distillation to give the liquid product, 1-diallylcarbamoyl-3-(2-methoxyethylsulphinyl)-1,2,4-triazole. The refractive index of the compound, $n_D^{25}$, was 1.5058.

The novel triazole compound used in the above reaction was prepared as follows.

A solution of 31.8 g. of 3-(2-methoxyethylthio)-1,2,4-triazole ws dissolved in 300 ml. of acetic acid and heated to 80°C. To this solution was added by portions 67.2 ml. of 100 vol. hydrogen peroxide and the temperature was maintained at 80°C. for two hours with cooling as necessary in the early stages. A small amount of 10% palladium/charcoal catalyst was added to destroy excess hydrogen peroxide. After an hour the solution was filtered and sulphur dioxide passed through the mixture as a precaution in case peroxides had been formed. The solution was vacuum evaporated and crystals of the sulphonyl compound were removed. On the addition of further petroleum ether to the liquors, filtration and vacuum distillation, there was obtained an oily liquid, 3-(2-methoxyethylsulphinyl)-1,2,4-triazole. Elemental analysis satisfactory.

EXAMPLE 58

This Example illustrates the preparation of compounds of formula II.

A solution of 0.03 mole 3-propylsulphonyl-1,2,4-triazole, 10 ml. triethylamine, 0.03 mole N-propyl-N-(2-chloroallyl)carbamoyl chloride in 40 ml. of dry tetrahydrofuran was refluxed for 15 hours. The mixture was then cooled and the triethylamine hydrochloride filtered off. After removal of the solvent the product was dissolved in methylene chloride and the solution washed with water. The product was recrystallized from an ether/petroleum ether (b.p. 40° – 60°C.) mixture. It was 1-[N-propyl-N-(2-chloroallyl)carbamoyl]-3-propylsulphonyl-1,2,4-triazole, m.p. 51.5° – 52°C. Elemental analysis was satisfactory.

The novel carbamoyl chloride used in the above reaction was prepared as follows:

80 g. of sodium hydroxide pellets were dissolved in 350 ml. water in a stirred two liter flask. The solution was cooled and 295 g. propylamine was added. The temperature was adjusted to 40°C. and maintained at this level whilst 222 g. of 2,3-dichloropropene was added over a period of about two hours. Heat evolution was observed. After stirring for a further two hours at 40°C., the mixture was gradually brought to reflux on the steam bath. It was refluxed gently for two hours and then allowed to stand for 15 hours at ambient temperature. Excess propylamine was distilled off through a 40 cm. bead-packed column. After cooling, the upper amine layer was separated and run with stirring into a cooled solution of concentrated hydrochloric acid in water.

The aqueous layer was extracted with ether and the extract stirred for ten minutes with the hydrochloric acid solution. The ether was separated and discarded and the aqueous solution was evaporated in vacuo on the steam bath. Water was added, the solution was cooled in ice and 200 ml. of 18.5N sodium hydroxide added. The amine layer was separated, dried over successive amounts of sodium hydroxide pellets and distilled from an oil bath through a bead-packed column. The product, N-(2-chloroallyl)propylamine, had a b.p. of 148° – 153°C.

250 ml. ethyl acetate was stirred and heated under reflux whilst a brisk stream of phosgene was passed in. A solution of 0.25 mole. N-(2-chloroallyl)propylamine in 75 ml. ethyl acetate was then added dropwise over a period of about 4½ hours. After passing in phosgene for a further fifteen minutes, ethyl acetate was removed in vacuo and the product vacuum distilled; N-propyl-N-(2-chloroallyl)carbamoyl chloride, b.p. 97° – 99°C./17 mm.

The triazole intermediate used in the preparation was made as follows.

3-Mercapto-1,2,4-triazole (20.2 g.) was added to a solution of 4.8 g. sodium in 150 ml. absolute ethanol. When dissolution was complete 24.6 g. propyl bromide was added. The stirred mixture was gradually heated to boiling under reflux, refluxed for 1 hour, cooled to room temperature and filtered. The filtrate was distilled to dryness under reduced pressure and the residue was dissolved in ether. The resulting solution was filtered, dried over anhydrous sodium sulphate and distilled under reduced pressure to give 3-propylthio-1,2,4-triazole, b.p. 143° – 144°C./1 mm. This product solidified, m.p. 53° – 56°C.

To a solution of 14.3 g. 3-propylthio-1,2,4-triazole in 100 ml. glacial acetic acid was added 28.5 ml. 100 vol. hydrogen peroxide solution (2.5 molecular proportions). The solution was heated gradually to 95° – 100°C., kept at this temperature for 2 hours and then distilled to dryness under reduced pressure. The residue was recrystallized from toluene to give 3-propylsulphonyl-1,2,4-triazole, m.p. 116° – 117°C. Elemental analysis satisfactory.

The following compounds were produced by an analogous method:

1-[N-propyl-N-(2-chloroethyl)carbamoyl]-3-methylsulphonyl-1,2,4-triazole, m.p. 106.5° – 107°C.

1-[N-propyl-N-(2-chloroallyl)carbamoyl]-3-sec.-butylsulphonyl-1,2,4-triazole, an oil, $n_D^{26}$ 1.5178.

1-[N-ethyl-N-(2-chloroallyl)carbamoyl]-3-isopropylsulphonyl-1,2,4-triazole, m.p. 75.5° – 76.5°C.

1-[N-ethyl-N-(2-chloroallyl)carbamoyl]-3-butylsulphonyl-1,2,4-triazole, an oil, $n_D^{22}$ 1.5198 (97.1% 1-isomer by GLC assay)

1-[N-ethyl-N-(2-chloroallyl)carbamoyl]-3-isobutylsulphonyl-1,2,4-triazole, an oil, $n_D^{22}$ 1.5195 (97.9% 1-isomer by GLC assay)

1-[N-ethyl-N-(2-chloroallyl)carbamoyl]-3-sec.butylsulphonyl-1,2,4-triazole, an oil, $n_D^{22}$ 1.5231 (98.1% 1-isomer by GLC assay)

1-[N-ethyl-N-(2-chloroallyl)carbamoyl]-3-ethylsulphonyl-1,2,4-triazole, an oil, $n_D^{22}$ 1.5298 (96.4% 1-isomer by GLC assay)

1-[N-ethyl-N-(2-chloroallyl)carbamoyl]-3-propyl-sulphonyl-1,2,4-triazole, an oil, $n_D^{22}$ 1.5243 (97.2% 1-isomer by GLC assay)

1-[N-allyl-N-(2-chloroallyl)carbamoyl]-3-ethylsulphonyl-1,2,4-triazole, an oil, $n_D^{26}$ 1.5306

1-[N-allyl-N-(2-chloroallyl)carbamoyl]-3-propylsulphonyl-1,2,4-triazole, an oil, $n_D^{26}$ 1.5260

1-[N-allyl-N-(2-chloroallyl)carbamoyl]-3-isopropylsulphonyl-1,2,4-triazole, an oil, $n_D^{26}$ 1.5274

1-[N-allyl-N-(2-chloroallyl)carbamoyl]-3-butylsulphonyl-1,2,4-triazole, an oil, $n_D^{26}$ 1.5220 (94.9% 1-isomer by GLC assay)

1-[N-allyl-N-(2-chloroallyl)carbamoyl]-3-isobutylsulphonyl-1,2,4-triazole, an oil, $n_D^{26}$ 1.5214 (94.8% 1-isomer by GLC assay)

1-[N-allyl-N-(2-chloroallyl)carbamoyl]-3-sec.butylsulphonyl-1,2,4-triazole, an oil, $n_D^{26}$ 1.5248 (95.3% 1-isomer by GLC assay)

The following novel intermediate carbamoyl chloride was prepared:

N-ethyl-N-(2-chloroallyl)carbamoyl chloride, b.p. 62.5° – 66°C./0.1 mm. (98.9% 1-isomer by GLC assay)

EXAMPLE 59

This Example illustrates the preparation of compounds of the formula II.

A solution of 6.15 g. 3-(2-ethoxyethylsulphonyl)-1,2,4-triazole, 6 ml. triethylamine, 7.15 g N-ethyl-N-(2,3-dichloroallyl)carbamoyl chloride in 40 ml. of dry tetrahydrofuran was heated under reflux for six hours. After cooling the amine hydrochloride was filtered off. The solvent was removed and the product solidified on cooling. It was crystallized from benzene/petroleum ether (b.p. 62°– 68°C.) mixture and was found to have a m.p. of 82° – 83.5°C. The product was 1-[N-ethyl-N-(2,3-dichoroallyl)carbamoyl]-3-(2-ethoxyethylsulphonyl)-1,2,4-triazole. Elemental analysis was satisfactory.

The triazole and carbamoyl chloride intermediates were prepared a similar way to that described in Example 58.

The following compounds were prepared in an analogous way:

1-[N-ethyl-N-(2-chloroallyl)carbamoyl]-3-(2-methoxyethylsulphonyl)-1,2,4-triazole, m.p. 52° – 53°C.

1-[N-ethyl-N-(2-chloroallyl)carbamoyl]-3-(2-ethoxyethylsulphonyl)1,2,4-triazole, m.p. 79.5° – 80°C.

1-[N-propyl-N-chloroallyl)carbamoyl]-3-(2-methoxyethylsulphonyl)-1,2,4-triazole, m.p. 58° – 60°C.

1-[N-propyl-N-(2-chloroallyl)carbamoyl]-3-(2-ethoxyethylsulphonyl)-1,2,4-triazole, m.p. 47° – 49°C.

1-(N-ethyl-N-chloromethylcarbamoyl)-3-(2-ethoxyethylsulphonyl)-1,2,4-triazole, m.p.71° – 72°C.

1-[N-allyl-N-(2-chloroallyl)carbamoyl]-3-(2-methoxyethylsulphonyl)-1,2,4-triazole, an oil, $n_D^{26}$ 1.5256 (93.4% 1-isomer by GLC)

1-[N-allyl-N-(2-chloroallyl)carbamoyl]-3-(2-ethoxyethylsulphonyl)-1,2,4-triazole, m.p. 71° – 80°C.

EXAMPLE 60

This Example illustrates the preparation of a compound of formula II.

A solution of 7.5 g. 1-dipropylcarbamoyl-3-butylsulphinyl-1,2,4-triazole and 4 ml. dry pyridine in 15 ml. of methylene chloride was cooled in ice and stirred whilst a solution of 2 ml. sulphuryl chloride in 10 ml. methylene chloride was slowly added. Stirring in the ice-bath was continued for one hour, followed by stirring at ambient temperature for a further hour. The solution was rapidly washed with ice-cold water, dried over magnesium sulphate and the solvent removed in vacuo. The product, 1-dipropylcarbamoyl-3-(1-chlorobutylsulphinyl)-1,2,4-triazole was a viscous gum which did not crystallize even when cooled in solid carbon dioxide/acetone. Elemental analysis was satisfactory.

EXAMPLE 61

In an analogous manner to that described in Example 58, the following compounds were prepared.

1[N-propyl-N-(2-chloroallyl)carbamoyl]-3-n-butylsulphonyl-1,2,4-triazole, an oil, $n_D^{25}$ 1.5136

1-[N-propyl-N-(2-chloroallyl)carbamoyl]-3-ethylsulphonyl-1,2,4-triazole, m.p. 50° – 50.5°C.

1-[N-propyl-N-(2-chloroallyl)carbamoyl]-3-isobutylsulphonyl-1,2,4-triazole, an oil, $n_D^{25}$ 1.5125

1-[N-propyl-N-(2-chloroallyl)carbamoyl]-3-isopropylsulphonyl-1,2,4-triazole, an oil, $n_D^{25}$ 1.5168

1-[N-ethyl-N-(2-chloroethyl)carbamoyl]-3-ethylsulphonyl-1,2,4-triazole, m.p. 73° – 74°C.

1-[N-propyl-N-(2-chloroethyl)carbamoyl]-3-ethylsulphonyl-1,2,4-triazole, m.p. 55° – 56°C.

The following novel intermediate carbamoyl chlorides were prepared.

N-ethyl-N-(2-chloroethyl)carbamoyl chloride

N-propyl-N-(2-chloroethyl)carbamoyl chloride

EXAMPLE 62

This Example illustrates the preparation of compounds of formula II.

A solution of 0.03 mole 3-propylsulphonyl-1,2,4-triazole, 6 ml. triethylamine and 0.033 mole N-ethyl-N-cyclopropylcarbamoyl chloride in 40 ml. dry tetrahydrofuran was heated under reflux for 5 hours. The cooled reaction mixture was filtered to remove triethylamine hydrochoride and the filtrate was evaporated to remove solvent. An ether solution of the liquid product was charcoaled, the ether evaporated and the residue heated to 120°C in a high vacuum to remove excess carbamoyl chloride, 1-(N-ethyl-N-cyclopropylcarbamoyl)-3-propylsulphonyl-1,2,4-triazole $n_D^{22}$ 1.5148 (96.6% 1-isomer by GLC assay). Elemental analysis was satisfactory.

The novel carbamoyl chloride used in the above reaction was prepared as follows.

First the novel N-ethyl-N-cyclopropylamine was prepared. 28.5 g. cyclopropylamine was diluted with 75 ml. absolute ethanol and cooled below 20°C whilst 19.8 g. acetaldehyde was added over a period of fifteen minutes. The solution was added to 75 ml. absolute ethanol in which 0.3 g. of platinum oxide has been reduced at ambient temperature and pressure. The solution was added and hydrogenated likewise and the theoretical amount of hydrogen was absorbed in about five hours. After separation from the catalyst be decantation, the solution was made definitely acid by the addition of 50 ml. of concentrated hydrochloride acid and evaporated in vacuo on a steam bath. The residue was dissolved in 70 ml. water and the amine liberated by the addition of 50 ml. of 18.5N sodium hydroxide.

The amine layer was separated and dried over successive amounts of sodium hydroxide pellets. It was distilled from barium oxide to give a liquid product, b.p. 82° – 85°C.

250 ml. of ethyl acetate was stirred and refluxed whilst a brisk stream of phosgene was passed in. After about ten minutes a solution of 21.95g. cyclopropylamine in 75 ml. ethyl acetate was added dropwise below the surface of the liquid over a period of 2½ hours. After a further fifteen minutes the ethyl acetate was distilled off and the residual oil distilled in vacuo, b.p. 96°C/17 mm.

The following compounds were prepared in an analogous way:

1-(N-ethyl-N-cyclopropylcarbamoyl)-3-butylsulphonyl-1,2,4-triazole, m.p. 68° – 68.5°C.

1-(N-ethyl-N-cyclopropylcarbamoyl)-3-isopropylsulphonyl-1,2,4-triazole, m.p. 51° – 52°C.

1-(N-ethyl-N-cyclopropylcarbamoyl)-3-ethylsulphonyl-1,2,4-triazole, an oil, $n_D^{15}$ 1.5214 (94.7% 1-isomer by GLC assay)

1-(N-propyl-N-cyclopropylcarbamoyl)-3-ethylsulphonyl-1,2,4-triazole, an oil, $n_D^{22}$ 1.5147 (94.5% 1-isomer by GLC assay)

1-(N-propyl-N-cyclopropylcarbamoyl)-3-propylsulphonyl-1,2,4-triazole, an oil, $n_D^{22}$ 1.5100 (95.1% 1-isomer by GLC assay)

1-(N-propyl-N-cyclopropylcarbamoyl)-3-isopropylsulphonyl-1,2,4-triazole, an oil, $n_D^{22}$ 1.5114 (98.4% 1-isomer by GLC assay)

1-(N-propyl-N-cyclopropylcarbamoyl)-3-butylsulphonyl-1,2,4-triazole, an oil, $n_D^{22}$ 1.5079 (97.3% 1-isomer by GLC assay)

The following novel intermediates were prepared.

N-propyl-N-cyclopropylamine, b.p. 108° – 110°C.

N-propyl-N-cyclopropylcarbamoyl chloride, b.p. 112° – 114°C./20 mm.

EXAMPLE 63

This Example illustrates the preparation of compounds of formula II.

A solution of 6.15 g. 3-(2-ethoxyethylsulphonyl)-1,2,4-triazole, 6 ml. triethylamine and 4.9 g. N-ethyl-N-chloropropylcarbamoyl chloride in 40 ml. of dry tetrahydrofuran was heated under reflux for 15 hours. The cooled reaction mixture was filtered to remove triethylamine hydrochloride and the filtrate was evaporated to remove solvent. The product was treated with 100 ml. petrol (b.p. 62° – 68°C.) and stirred. Crystals were collected and recrystallized from benzene/petrol (b.p. 62° – 68°C.) mixture. 1-N-ethyl-N-cyclopropylcarbamoyl-3-(2-ethoxyethylsulphonyl)-1,2,4-triazole was found to have a melting point of 89.5° – 90.5°C. Elemental analysis was satisfactory.

EXAMPLE 64

This Example illustrates the preparation of a composition comprising a compound of the formula II.

A dispersible powder was prepared by grinding together a mixture of the following ingredients in a hammer mill.

|  | % w/w |
|---|---|
| 1-Diallylcarbamoyl-3-(2-ethoxyethylsulphonyl)-1,2,4-triazole | 25.0 |
| Sodium N-methyl-N-palmitoyltaurate | 6.0 |
| Sodium di-octylsulphosuccinate | 0.5 |
| Colloidal silicic acid | 25.0 |
| Kaolin | 43.5 |

Similar dispersible powders were prepared in which the triazole compound in the above formulation was replaced by the following compounds.

1-Diallylcarbamoyl-3-(2-methoxyethylsulphonyl)-1,2,4-triazole

1-Dipropylcarbamoyl-3-(2-ethoxyethylsulphonyl)-1,2,4-triazole

EXAMPLE 65

This Example illustrates the preparation of a composition comprising a compound of the formula II.

An emulsifiable concentrate suitable for dilution with water to form an aqueous emulsion was prepared from the following ingredients.

|  | % w/v |
|---|---|
| 1-(N-ethyl-N-2-methoxyethylcarbamoyl)-3-ethylsulphonyl-1,2,4-triazole | 20.0 |
| Calcium dodecylbenzenesulphonate | 2.5 |
| Nonylphenoxypolyethoxyethanol * | 2.5 |
| Xylene | to 100.0 |

* A nonylphenol-ethylene oxide condensate containing an average of 14 mols. ethylene oxide per mol. nonylphenol.

Similar emulsifiable concentrates were prepared in which the triazole compound in the above formulation was replaced by the following compounds.

1-(N-ethyl-N-2-ethoxyethylcarbamoyl)-3-n-butylsulphonyl-1,2,4-triazole 1-(N-ethyl-N-2-ethoxyethylcarbamoyl)-3-isobutylsulphonyl-1,2,4-triazole 1-(N-propyl-N-2-methoxyethylcarbamoyl)-3-n-butylsulphonyl-1,2,4-triazole.

EXAMPLE 66

This Example illustrates the herbicidal use of a composition comprising a compound of the formula II.

In tests carried out in the glasshouse, trays of soil were sown with seeds of various weeds and then immediately sprayed with aqueous suspensions of compounds under test at various application rates of test compound. Seeded trays of soil receiving no chemical treatment were used as controls. At an application rate of 0.5 lb./acre, all the triazoles mentioned in Examples 64 and 65 controlled the weeds crabgrass, barnyard grass, yellow foxtail and Johnson grass (no germination or emergent seedlings severely and irrecoverably stunted).

EXAMPLE 67

This Example illustrates the preparation of a compound of formula III.

A mixture of 6.9 g. 3-diallylsulphamoyl-1,2,4-triazole, 4.5 g. diethylcarbamoyl chloride, 6 ml. triethylamine and 25 ml. dry tetrahydrofuran was refluxed under anhydrous conditions for 1.5 hours. The cooled reaction mixture was filtered to remove triethylamine hydrochloride and the filtrate was evaporated to remove solvent. The solid residue was recrystallized from petroleum ether, b.p. 60° – 80°C., to give 1-diethylcarbamoyl-3-diallylsulphamoyl-1,2,4-triazole, m.p. 49° – 51°C. Elemental analysis satisfactory.

The novel intermediate 3-diallylsulphamoyl-1,2,4-triazole was prepared in the following way. A stream of chlorine was passed into a solution of 20.2 g. 1,2,4-triazole-3-thiol in 330 ml. 2N hydrochloric acid, maintaining the temperature of the reaction mixture at 0° to −2°C. by means of external cooling. When excess chlorine was present (after 1.5 hours) the solid product was collected by filtration, washed with water, and sucked as dry as possible on a suction filter. There was thus obtained 1,2,4-triazole-3-sulphonyl chloride in the form of a damp solid, which was used immediately in the next stage of the preparation. This damp solid was gradually added to a stirred solution of 48.5 g. diallylamine in 100 ml. water, maintaining the temperature of the reaction mixture at 20°C. The reaction mixture was allowed to stand at 20°C. for 20 minutes, and was then acidified to pH 4.0 with concentrated hydrochloric acid. The resulting solid product was collected by filtration, washed with water, and recrystallized from water to give 3-diallylsulphamoyl-1,2,4-triazole, m.p. 131° – 133°C. Elemental analysis satiscactory.

EXAMPLE 68

This Example illustrates the preparation of compounds of formula III.

By reacting the appropriate carbamoyl chloride with the appropriate 3-sulphamoyl-1,2,4-triazole in an analogous manner to that described in Example 67, the following compounds were prepared.

1-diallylcarbamoyl-3-dimethylsulphamoyl-1,2,4-triazole, m.p. 58°C.
1-(N-methyl-N-n-butylcarbamoyl)-3-dimethylsulphamoyl-1,2,4-triazole, b.p. 191° – 193°C./0.5 mm.
1-diethylcarbamoyl-3-morpholinosulphonyl-1,2,4-triazole, m.p. 113° – 114°C.
1-diallylcarbamoyl-3-(1-piperidylsulphonyl)-1,2,4-triazole, m.p. 72° – 73°C.
1-(N-methyl-N-n-butylcarbamoyl)-3-(1-piperidylsulphonyl)-1,2,4-triazole, m.p. 70° – 71°C.
1-(N-allyl-N-propylcarbamoyl)-3-(1-piperidylsulphonyl)-1,2,4-triazole, an oil, $n_D^{23}$ 1.519
1-diethylcarbamoyl-3-(1-piperidylsulphonyl)-1,2,4-triazole, m.p. 108° – 110°C.
1-(N-methyl-N-cyclohexylcarbamoyl)-3-(1-piperidylsulphonyl)-1,2,4-triazole, m.p. 117° – 118°C.
1-(N-allyl-N-ethylcarbamoyl)-3-(1-piperidylsulphonyl)-1,2,4-triazole, m.p. 50° – 52°C.
1-diallylcarbamoyl-3-diallylsulphamoyl-1,2,4-triazole, an oil, $n_D^{21}$ 1.5226
1-diethylcarbamoyl-3-diallylsulphamoyl-1,2,4-triazole, m.p. 49° – 51°C.
1-N-methyl-N-cyclohexylcarbamoyl)-3-diallylsulphamoyl-1,2,4-triazole, m.p. 55° – 56°C.
1-(N-allyl-N-ethylcarbamoyl)-3-diallylsulphamoyl-1,2,4-triazole, m.p. 40° – 41°C.
1-(N-allyl-N-propylcarbamoyl)-3-diallylsulphamoyl-1,2,4-triazole, an oil, $n_D^{23}$ 1.513
1-diallylcarbamoyl-3-diethylsulphamoyl-1,2,4-triazole, m.p. 62° – 63°C.
1-diethylcarbamoyl-3-diethylsulphamoyl-1,2,4-triazole, m.p. 105°C.
1-(N-methyl-N-cyclohexylcarbamoyl)-3-diethylsulphamoyl-1,2,4-triazole, m.p. 83° – 85°C.
1-(N-allyl-N-propylcarbamoyl)-3-diethylsulphamoyl-1,2,4-triazole, m.p. 34° – 35°C.
1-diallylcarbamoyl-3-pyrrolidinosulphonyl-1,2,4-triazole, m.p. 67° – 68°C.
1-(N-methyl-N-cyclohexylcarbamoyl)-3-pyrrolidinosulphonyl-1,2,4-triazole, m.p. 109° – 110°C.
1-diethylcarbamoyl-3-pyrrolidinosulphonyl-1,2,4-triazole, m.p. 87° – 88°C.
1-(N-methyl-N-n-butylcarbamoyl)-3-pyrrolidinosulphonyl-1,2,4-triazole, m.p. 75° – 76°C.
1-(N-allyl-N-propylcarbamoyl)-3-pyrrolidinosulphonyl-1,2,4-triazole, m.p. 38° – 40°C.
1-(N-allyl-N-ethylcarbamoyl)-3-pyrrolidinosulphonyl-1,2,4-triazole, m.p. 61° – 63°C.

By reacting 1,2,4-triazole-3-sulphonyl chloride with the appropriate amine in an analogous manner to that described in Example 67, the following novel intermediates were prepared.

3-morpholinosulphonyl-1,2,4-triazole, m.p. 227° – 229°C.
3-diallylsulphamoyl-1,2,4-triazole, m.p. 131° – 133°C.
3-diethylsulphamoyl-1,2,4-triazole, m.p. 143° – 144°C.
3-pyrrolidinosulphonyl-1,2,4-triazole, m.p. 240° – 241°C.

Satisfactory elemental analyses were obtained for all the compounds listed above.

EXAMPLE 69

This Example illustrates the preparation of compounds of formula III.

By reacting the appropriate carbamoyl chloride with the appropriate 3-sulphamoyl-1,2,4-triazole in an analogous manner to that described in Example 67, the following compounds were prepared.

1-diallylcarbamoyl-3-dipropylsulphamoyl-1,2,4-triazole, m.p. 54° – 55°C.
1-diallylcarbamoyl-3-di-n-butylsulphamoyl-1,2,4-triazole, m.p. 83° – 84°C.
1-diallylcarbamoyl-3-(N-ethyl-N-hexylsulphamoyl)-1,2,4-triazole, an oil, $n_D^{23}$ 1.5032
1-diallylcarbamoyl-3-(N-n-butyl-N-propylsulphamoyl)-1,2,4-triazole, an oil, $n_D^{23}$ 1.5052
1-diallylcarbamoyl-3-(2,6-dimethylmorpholinosulphonyl)-1,2,4-triazole, m.p. 87° – 88.5°C.
1-diallylcarbamoyl-3-(N-methyl-N-n-butylsulphamoyl)-1,2,4-triazole, an oil, $n_D^{23}$ 1.509
1-N-methyl-N-cyclohexylcarbamoyl)-3-(N-methyl-N-n-butylsulphamoyl)--triazole, m.p. 109° – 110°C.
1-(N-allyl-N-ethylcarbamoyl)-3-(N-methyl-N-n-butylsulphamoyl)-1,2,4-triazole, m.p. 37° – 38°C.
1-(N-allyl-N-propylcarbamoyl)-3-(N-methyl-N-n-butylsulphamoyl)-1,2,4-triazole, an oil, $n_D^{23}$ 1.501
1-diallylcarbamoyl-3-(N-methyl-N-cyclohexylsulphamoyl)-1,2,4-triazole, m.p. 68° – 69.5°C.
1-diethylcarbamoyl-3-(N-methyl-N-cyclohexylsulphamoyl)-1,2,4-triazole, m.p. 74° – 75°C.
1-diethylcarbamoyl-3-(N-methyl-N-sec.butylsulphamoyl)-1,2,4-triazole, m.p. 47° – 50°C.
1-diallylcarbamoyl-3-(N-methyl-N-sec.butylsulphamoyl)-1,2,4-triazole, an oil, $n_D^{23}$ 1.5068
1-diallylcarbamoyl-3-(N-allyl-N-methylsulphamoyl)-1,2,4-triazole, an oil, $n_D^{23}$ 1.519
1-diethylcarbamoyl-3-(N-allyl-N-methylsulphamoyl)-1,2,4-triazole, m.p. 58° – 60°C.
1-(N-methyl-N-cyclohexylcarbamoyl)-3-(N-allyl-N-methylsulphamoyl)-1,2,4-triazole, m.p. 72° – 74°C.
1-(N-allyl-N-ethylcarbamoyl)-3-(N-allyl-N-methylsulphamoyl)-1,2,4-triazole, an oil, $n_D^{23}$ 1.515
1-(N-allyl-N-propylcarbamoyl)-3-(N-allyl-N-methylsulphamoyl)-1,2,4-triazole, an oil, $n_D^{23}$ 1.511
1-diallylcarbamoyl-3-[N,N-di(2-methylallyl)sulphamoyl]-1,2,4-triazole, m.p. 66° – 67°C.

By reacting 1,2,4-triazole-3-sulphonyl chloride with the appropriate amine in an analogous manner to that described in Example 67, the following novel intermediates were prepared:

3-dipropylsulphamoyl-1,2,4-triazole, m.p. 111° – 112°C.
3-di-n-butylsulphamoyl-1,2,4-triazole, m.p. 83° – 84°C.
3-(N-ethyl-N-n-hexylsulphamoyl)-1,2,4-triazole, m.p. 100° – 100.5°C.
3-(N-n-butyl-N-propylsulphamoyl)-1,2,4-triazole, m.p. 78.5° – 79°C.
3-(2,6-dimethylmorpholinosulphonyl)-1,2,4-triazole, m.p. 231° – 232°C.
3-(N-methyl-N-n-butylsulphamoyl)-1,2,4-triazole, m.p. 119° – 120°C.
3-(N-methyl-N-cyclohexylsulphamoyl)-1,2,4-triazole, m.p. 156°157.5°– 151.5°C.
3-(N-methyl-N-sec.butylsulphamoyl)-1,2,4-triazole, m.p. 132° – 133°C.
3-(N-allyl-N-methylsulphamoyl)-1,2,4-triazole, m.p. 140° – 142°C.
3-N,N-di(2-methylallyl)sulphamoyl-1,2,4-triazole, m.p. 151° – 152°C.

Satisfactory elemental analyses were obtained for all the compounds listed above.

EXAMPLE 70

This Example illustrates the preparation of compounds of formula III.

A solution of 7.04 g. 3-dimethylsulphamoyl-1,2,4-triazole, 8 ml. triethylamine and 6.0 g. diethylcarbamoyl chloride in 25 ml. dry tetrahydrofuran was refluxed for 1½ hours.

Triethylamine hydrochloride precipitated and was filtered off. Light petroleum was added to the filtrate to precipitate the product which was separated and recrystallized from light petroleum (b.p. 80° – 100°C.). The product, 1-diethylcarbamoyl-3-dimethylsulphamoyl-1,2,4-triazole had a melting point of 83°C.

The triazole intermediate used in the above reaction was prepared as follows. 50.5 g. 1,2,4-Triazole-3-thiol was suspended in 800 ml. of 2N hydrochloric acid and stirred at 0° – 2°C. while a stream of chlorine was passed in. The thiol reactant passed into solution and later 1,2,4-triazole-3-sulphonyl chloride separated. After 2 hours excess of chlorine was present and the sulphonyl chloride was filtered off, wased with ice-cold water and used immediately.

The sulphonyl chloride was gradually added with stirring to 210 ml. of 25% aqueous dimethylamine at 15° – 20°C. A solution resulted. After 30 minutes, acidification with hydrochloric acid precipitated the product which was recrystallized from ethanol, giving a product with a melting point 192° – 194°C.

The following compounds were prepared in an analogous manner.

1-diethylcarbamoyl-3-(N-methyl-N-butylsulphamoyl)-1,2,4-triazole, m.p. 52° – 53.5°C.
1-diallylcarbamoyl-3-(N-propyl-N-isopropylsulphamoyl)-1,2,4-triazole, m.p. 51° – 52°C.
1-(N-methyl-N-butylcarbamoyl)-3-(N-methyl-N-butylsulphamoyl)-1,2,4-triazole, an oil, $n_D^{20}$ 1.496
1-(N-allyl-N-ethylcarbamoyl)-3-diethylsulphamoyl-1,2,4-triazole, m.p. 74° – 75°C.
1-(N-ethyl-N-butylcarbamoyl)-3-(N-allyl-N-methylsulphamoyl)-1,2,4-triazole, an oil, $n_D^{20}$ 1.504
1-(N-ethyl-N-butylcarbamoyl)-3-diethylsulphamoyl-1,2,4-triazole, m.p. 56° – 57.5°C.
1-(N-ethyl-N-butylcarbamoyl)-3-diallylsulphamoyl-1,2,4-triazole, an oil, $n_D^{20}$ 1.5065
1-(N-ethyl-N-butylcarbamoyl)-3-(N-methyl-N-butylsulphamoyl)-1,2,4-triazole, an oil, $n_D^{20}$ 1.495
1-(N-propyl-N-propynylcarbamoyl)-3-(N-allyl-N-methylsulphamoyl)-1,2,4-triazole, an oil, $n_D^{20}$ 1.5175 (98.6% 1-isomer by GLC assay)
1-(N-propyl-N-propynylcarbamoyl)-3-(N-methyl-N-butylsulphamoyl-1,2,4-triazole, $n_D^{20}$ 1.5065 (97.3% 1-isomer by GLC assay)
1-(N-propyl-N-propynylcarbamoyl)-3-diallylsulphamoyl-1,2,4-triazole, m.p. 33° – 34°C.
1-(N-ethyl-N-butylcarbamoyl)-3-diethylsulphamoyl-1,2,4-triazole, m.p. 56° – 57.5°C.
1-(N-allyl-N-cyclohexylcarbamoyl)-3-diethylsulphamoyl-1,2,4-triazole, m.p. 71° – 72°C.
1-(N-propyl-N-2-chloroethylcarbamoyl)-3-diethylsulphamoyl-1,2,4-triazole, m.p. 40° – 42°C.
1-diallylcarbamoyl-3-(N-propyl-N-propynylsulphamoyl)-1,2,4-triazole, m.p. 54° – 55°C.
1-diallylcarbamoyl-3-di(2-ethoxyethyl)sulphamoyl-1,2,4-triazole, an oil, $n_D^{20}$ 1.521 (97.3% 1-isomer by GLC assay)
1-diallylcarbamoyl-3-(N-propyl-N-hexylsulphamoyl)-1,2,4-triazole, an oil, $n_D^{20}$ 1.526 (96.6% 1-isomer by GLC assay)
1-(N-methyl-N-ethylcarbamoyl)-3-dimethylsulphamoyl-1,2,4-triazole, m.p. 34° – 37°C.
1-(N-ethyl-N-cyclopropylcarbamoyl)-3-diethylsulphamoyl-1,2,4-triazole, m.p. 60° – 62°C.
1-(N-allyl-N-hexylcarbamoyl)-3-diethylsulphamoyl 1,2,4-triazole, m.p. 42° – 43°C.
1-(N-allyl-N-isopropylcarbamoyl)-3-diethylsulphamoyl-1,2,4-triazole, m.p. 64° – 70°C.
1-(N-allyl-N-isopropylcarbamoyl)-3-(N-methyl-N-butylsulphamoyl-1,2,4-triazole, m.p. 35° – 38°C.
1-(N-allyl-N-isopropylcarbamoyl)-3-diallylsulphamoyl-1,2,4-triazole, m.p. 32° – 35°C.
1-(N-allyl-N-isopropylcarbamoyl)-3-(N-methyl-N-allylsulphamoyl)-1,2,4-triazole, an oil, $n_D^{20}$ 1.515
1-di-(2-methylallyl)carbamoyl-3-diethylsulphamoyl-1,2,4-triazole, an oil, $n_D^{20}$ 1.5096 (99.8% 1-isomer by GLC assay)
1-(N-allyl-N-hexylcarbamoyl)-3-diallylsulphamoyl-1,2,4-triazole, an oil, $n_D^{20}$ 1.5075 (94.9% 1-isomer by GLC assay).
1-(N-allyl-N-hexylcarbamoyl)-3-(N-butyl-N-methylsulphamoyl)-1,2,4-triazole, an oil, $n_D^{20}$ 1.497 (95.9% 1-isomer by GLC assay).
1-diethylcarbamoyl-3-(N-hexyl-N-propylsulphamoyl)-1,2,4-triazole, m.p. 59° – 60°C.
1-(N-ethyl-N-5-chloropentylcarbamoyl)-3-diethylsulphamoyl-1,2,4-triazole, an oil, $n_D^{20}$ 1.506 (88.1% 1-isomer by GLC assay).
1-diethylcarbamoyl-3-di-(2-ethoxyethyl)sulphamoyl-1,2,4-triazole, m.p. 44° – 45°C.
1-(N-propyl-N-prop-2-ynylcarbamoyl)-3-diethylsulphamoyl-1,2,4-triazole, m.p. 52° – 54°C.
1-di-(2-methylallylcarbamoyl)-3-diallylsulphamoyl-1,2,4-triazole, an oil, $n_D^{20}$ 1.5185
1-diethylcarbamoyl-3-dipropylsulphamoyl-1,2,4-triazole, m.p. 110°C.
1-diallylcarbamoyl-3-(N-propyl-N-2-chloroallylsulphamoyl)-1,2,4-triazole, an oil, $n_D^{23}$ 1.5200 (98.5% 1-isomer by GLC assay).
1-diallylcarbamoyl-3-[N-propyl-N-(2-methoxyethyl)sulphamoyl]-1,2,4-triazole, an oil, $n_D^{23}$ 1.5080 (99.9% 1-isomer by GLC assay)

1-diallylcarbamoyl-3-(N-allyl-N-hexylsulphamoyl)-1,2,4-triazole, an oil, $n_D^{23}$ 1.5078 (98.5% 1-isomer by GLC assay).

1-diallylcarbamoyl-3-(N-cyclopropyl-N-ethylsulphamoyl)-1,2,4-triazole, m.p. 68° – 70°C.

1-diallylcarbamoyl-3-[N-allyl-N-(2-butoxyethyl)sulphamoyl]-1,2,4-triazole, an oil, $n_D^{24}$ 1.5073 (97.8% 1-isomer by GLC assay).

1-diallylcarbamoyl-3-[N-ethyl-N-(2-allyloxyethyl)sulphamoyl]-1,2,4-triazole, an oil, $n_D^{24}$ 1.5137 (99% 1-isomer by GLC assay)

1-(N-allyl-N-propylcarbamoyl)-3-(N-methyl-N-sec.-butylsulphamoyl)-1,2,4-triazole, m.p. 42° – 44°C.

1-diallylcarbamoyl-3-(N-methyl-N-pentylsulphamoyl)-1,2,4-triazole, m.p. 29° – 31°C.

1-diallylcarbamoyl-3-[N-propyl-N-(2-chloroallyl)sulphamoyl]-1,2,4-triazole, m.p. 42° – 43°C.

1-(N-butyl-N-ethylcarbamoyl)-3-(N-methyl-N-sec.-butylsulphamoyl)-1,2,4-triazole, an oil, $n_D^{24}$ 1.4945 (94.7% 1-isomer by GLC assay)

1-diallylcarbamoyl-3-[N-ethyl-N-(2,3-dichloroallyl)sulphamoyl]-1,2,4-triazole, m.p. 25°C.

1-(N-ethyl-N-hexylcarbamoyl)-3-diethylsulphamoyl-1,2,4-triazole, m.p. 54° – 55°C.

1-(N-ethyl-N-methylcarbamoyl)-3-diethylsulphamoyl-1,2,4-triazole, m.p. 49° – 50°C.

1-(N-ethyl-N-methylcarbamoyl)-3-diallylsulphamoyl-1,2,4-triazole, m.p. 26° – 27°C.

1-(N-ethyl-N-isopropylcarbamoyl)-3-diethylsulphamoyl-1,2,4-triazole, m.p. 80° – 81°C.

1-(N-ethyl-N-isopropylcarbamoyl)-3-diallylsulphamoyl-1,2,4-triazole, m.p. 45° – 46°C.

1-(N-butyl-N-methylcarbamoyl)-3-diethylsulphamoyl-1,2,4-triazole, an oil, $n_D^{20}$ 1.5005 (98.3% 1-isomer by GLC assay)

1-(N-butyl-N-methylcarbamoyl)-3-diallylsulphamoyl-1,2,4-triazole, an oil, $n_D^{20}$ 1.5115 (98.2% 1-isomer by GLC assay)

1-(N-allyl-N-isobutylcarbamoyl)-3-diethylsulphamoyl-1,2,4-triazole, m.p. 39° – 40°C.

1-(N-allyl-N-butylcarbamoyl)-3-diallylsulphamoyl-1,2,4-triazole, an oil, $n_D^{20}$ 1.510 (93.0% 1-isomer by GLC assay)

1-(N-allyl-N-isobutylcarbamoyl)-3-diallylsulphamoyl-1,2,4-triazole, an oil, $n_D^{20}$ 1.509 (98.8% 1-isomer by GLC assay)

1-(N-ethyl-N-isobutylcarbamoyl)-3-diallylsulphamoyl-1,2,4-triazole, an oil, $n_D^{20}$ 1.505 (98.4% 1-isomer by GLC assay)

1-(N-ethyl-N-isobutylcarbamoyl)-3-diethylsulphamoyl-1,2,4-traizole, m.p. 55° – 56°C.

1-diethylcarbamoyl-3-(N-methyl-N-pentylsulphamoyl)-1,2,4-triazole, m.p. 48° – 49°C.

1-diallylcarbamoyl-3-(N-butyl-N-ethylsulphamoyl)-1,2,4-triazole, m.p. 29° – 32°C.

1-diethylcarbamoyl-3-(N-butyl-N-ethylsulphamoyl)-1,2,4-triazole, m.p. 78° – 79°C.

1-diallylcarbamoyl-3-(N-allyl-N-propylsulphamoyl)-1,2,4-triazole, an oil, $n_D^{22}$ 1.5168

1-(N-ethyl-N-isopentylcarbamoyl)-3-diallylsulphamoyl)-1,2,4-triazole, an oil, $n_D^{22}$ 1.5028 (96.9% 1-isomer by GLC assay)

1-(N-ethyl-N-isopentylcarbamoyl)-3-diethylsulphamoyl)-1,2,4-triazole, m.p. 78° – 80°C.

1-diethylcarbamoyl-3-(N-allyl-N-propylsulphamoyl)-1,2,4-triazole, m.p. 75° – 77°C.

1-(N-ethyl-N-isopentylcarbamoyl)-3-(N-butyl-N-methylsulphamoyl)-1,2,4-triazole, an oil, $n_D^{25}$ 1.4896 (95.4% 1-isomer by GLC assay)

1-(N-ethyl-N-prop-2-ynylcarbamoyl)-3-diallylsulphamoyl-1,2,4-triazole, m.p. 72° – 74°C.

1-(N-ethyl-N-prop-2-ynylcarbamoyl)-3-diethylsulphamoyl-1,2,4-triazole, m.p. 104° – 106°C.

1-(N-methyl-N-pentylcarbamoyl)-3-diethylsulphamoyl-1,2,4-triazole, m.p. 43° – 44°C.

1-(N-methyl-N-pentylcarbamoyl)-3-diallylsulphamoyl-1,2,4-triazole, an oil, $n_D^{20}$ 1.504 (98.3% 1-isomer by GLC assay)

1-(N-ethyl-N-propylcarbamoyl)-3-diallylsulphamoyl-1,2,4-triazole, m.p. 38° – 40°C.

1-(N-allyl-N-pentylcarbamoyl)-3-diethylsulphamoyl-1,2,4-triazole, m.p. 40° – 41°C.

1-(N-ethyl-N-prop-2-ynylcarbamoyl)-3-(N-butyl-N-methylsulphamoyl)-1,2,4-triazole, an oil, $n_D^{26}$ 1.5073 (98.9% 1-isomer by GLC assay)

1-(N-ethyl-N-pentylcarbamoyl)-3-diallylsulphamoyl-1,2,4-triazole, an oil, $n_D^{26}$ 1.5005 (98% 1-isomer by GLC assay)

1-(N-ethyl-N-pentylcarbamoyl)-3-diethylsulphamoyl-1,2,4-triazole, an oil, $n_D^{26}$ 1.4929 (99.3% 1-isomer by GLC assay)

1(N-ethyl-N-pentylcarbamoyl)-3-(N-butyl-N-methylsulphamoyl)-1,2,4-triazole, an oil, $n_D^{26}$ 1.4908 (99.2% 1-isomer by GLC assay)

1-(N-allyl-N-pentylcarbamoyl)-3-diallylsulphamoyl-1,2,4-triazole, an oil, $n_D^{20}$ 1.5065 (99.7% 1-isomer by GLC assay)

1-(N-ethyl-N-propylcarbamoyl)-3-(N-allyl-N-hexylsulphamoyl)-1,2,4-triazole, an oil, $n_D^{20}$ 1.495 (99.9% 1-isomer by GLC assay)

1-(N-allyl-N-ethylcarbamoyl)-3-[N-propyl-N-(2-methoxyethyl)sulphamoyl]-1,2,4-triazole, m.p. 40° – 41°C.

1-(N-allyl-N-ethylcarbamoyl)-3-(N-allyl-N-propylsulphamoyl)-1,2,4-triazole, m.p. 35° – 37°C.

1-(N-butyl-N-ethylcarbamoyl)-3-(N-allyl-N-propylsulphamoyl)-1,2,4-triazole, an oil, $n_D^{20}$ 1.498 (99.3% 1-isomer by GLC assay)

1-(N-allyl-N-ethylcarbamoyl)-3-dimethylsulphamoyl-1,2,4-triazole, m.p. 68° – 70°C.

1-(N-ethyl-N-isopropylcarbamoyl)-3-dimethylsulphamoyl)-1,2,4-triazole, m.p. 71° – 74°C.

1-(N-allyl-N-isobutylcarbamoyl)-3-dimethylsulphamoyl-1,2,4-triazole, an oil, $n_D^{20}$ 1.504 (99.3% 1-isomer by GLC assay)

1-(N-allyl-N-propylcarbamoyl)-3-(N-butyl-N-ethylsulphamoyl)-1,2,4-triazole, an oil, $n_D^{20}$ 1.497 (99.7% 1-isomer by GLC assay)

1-diallylcarbamoyl-3-[N-ethyl-N-(2-methoxyethyl)sulphamoyl]-1,2,4-triazole, m.p. 32° – 33°C.

1-diethylcarbamoyl-3-[N-ethyl-N-(2-methoxyethyl)sulphamoyl]-1,2,4-triazole, m.p. 74° – 76°C.

1-diallylcarbamoyl-3-(N-hexyl-N-methylsulphamoyl)-1,2,4-triazole, an oil, $n_D^{23}$ 1.5070 (99.1% 1-isomer by GLC assay)

1-diethylcarbamoyl-3-(N-hexyl-N-methylsulphamoyl)-1,2,4-triazole, m.p. 63° – 64°C.

1-(N-allyl-N-methylcarbamoyl)-3-diallylsulphamoyl-1,2,4-triazole, an oil, $n_D^{27}$ 1.5192 (98.8% 1-isomer by GLC assay)

1-(N-allyl-N-methylcarbamoyl)-3-diethylsulphamoyl-1,2,4-triazole, m.p. 59° – 61°C.

1-(N-allyl-N-methylcarbamoyl)-3-(N-butyl-N-methylsulphamoyl)-1,2,4-triazole, an oil, $n_D^{27}$ 1.5055 (99.9% 1-isomer by GLC assay)

1-diethylcarbamoyl-3-dibutylsulphamoyl-1,2,4-triazole, m.p. 90° – 91°C.

1-diallylcarbamoyl-3-(N-ethyl-N-pentylsulphamoyl)-1,2,4triazole, m.p. 38° – 39°C.

1-diethylcarbamoyl-3-(N-ethyl-N-pentylsulphamoyl)-1,2,4-triazole, m.p. 86° – 87°C.

1-diethylcarbamoyl-3-di-(2-methylallyl)sulphamoyl-1,2,4-triazole, m.p. 84° – 85°C.

1-diallylcarbamoyl-3-(N-allyl-N-ethylsulphamoyl)-1,2,4-triazole, an oil, $n_D^{22}$ 1.5192 (99.9% 1-isomer by GLC assay)

1-(N-ethyl-N-sec.butylcarbamoyl)-3-diallylsulphamoyl-1,2,4-triazole, an oil, $n_D^{26}$ 1.5045 (96.4% 1-isomer by GLC assay)

1-(N-ethyl-N-sec.butylcarbamoyl)-3-diethylsulphamoyl-1,2,4-triazole, an oil, $n_D^{26}$ 1.4952 (94.6% 1-isomer by GLC assay)

1-(N-ethyl-N-sec.butylcarbamoyl)-3-(N-butyl-N-methylsulphamoyl)-1,2,4-triazole, an oil, $n_D^{26}$ 1.4928 (94.8% 1-isomer by GLC assay)

1-(N-methyl-N-hexylcarbamoyl)-3-(N-butyl-N-methylsulphamoyl)-1,2,4-triazole, an oil, $n_D^{27}$ 1.4912 (99.3% 1-isomer by GLC assay)

1-(N-ethyl-N-isopropylcarbamoyl)-3-(N-butyl-N-ethylsulphamoyl)-1,2,4-triazole, m.p. 39° – 41°C.

1-diethylcarbamoyl-3-(N-ethyl-N-methylsulphamoyl)-1,2,4-triazole, m.p. 61° – 62°C.

1-diallylcarbamoyl-3-(N-ethyl-N-methylsulphamoyl)-1,2,4-triazole, an oil $n_D^{20}$ 1.515 (99.9% 1-isomer by GLC assay)

1-(N-allyl-N-propylcarbamoyl)-3-(N-ethyl-N-methylsulphamoyl)-1,2,4-triazole, an oil, $n_D^{20}$ 1.504 (99.2% 1-isomer by GLC assay)

1-(N-butyl-N-ethylcarbamoyl)-3-(N-ethyl-N-methylsulphamoyl)-1,2,4-triazole, an oil, $n_D^{20}$ 1.495 (99.3% 1-isomer by GLC assay)

1-diethylcarbamoyl-3-(N-allyl-N-ethylsulphamoyl)1,2,4-triazole, m.p. 58° – 60°C.

1-diethylcarbamoyl-3-(N-ethyl-N-propylsulphamoyl)-1,2,4-triazole, m.p. 97° – 100°C.

1-diallylcarbamoyl-3-(N-ethyl-N-propylsulphamoyl)-1,2,4-triazole, m.p. 44° – 45°C.

1-(N-butyl-N-ethylcarbamoyl)-3-(N-ethyl-N-propylsulphamoyl)-1,2,4-triazole, m.p. 58° – 59°C.

1-(N-methyl-N-propylcarbamoyl)-3-diethylsulphamoyl-1,2,4-triazole, m.p. 54° – 55°C.

1-(N-methyl-N-propylcarbamoyl)-3-(N-butyl-N-methylsulphamoyl)-1,2,4-triazole, an oil, $n_D^{23}$ 1.5025 (99.0% 1-isomer by GLC assay)

1-(N-methyl-N-propylcarbamoyl)-3-diallylsulphamoyl-1,2,4-triazole, an oil, $n_D^{23}$ 1.5160 (98.5% 1-isomer by GLC assay)

1-diethylcarbamoyl-3-(N-methyl-N-isobutylsulphamoyl)-1,2,4-triazole, m.p. 84° – 86°C.

1-diallylcarbamoyl-3-(N-pentyl-N-propylsulphamoyl)-1,2,4-triazole, m.p. 43° – 44°C.

1-diethylcarbamoyl-3-(N-pentyl-N-propylsulphamoyl)-1,2,4-triazole, m.p. 72° – 73°C.

1-diethylcarbamoyl-3-(N-propyl-N-isopropylsulphamoyl)-1,2,4-triazole, m.p. 106° – 108°C.

1-diallylcarbamoyl-3-(N-isobutyl-N-methylsulphamoyl)-1,2,4-triazole, m.p. 63° – 64°C.

1-(N-allyl-N-ethylcarbamoyl)-3-[N-methyl-N-(4-fluorophenyl) sulphamoyl]-1,2,4-triazole, m.p. 68° – 71°C.

1-(N-ethyl-N-pentylcarbamoyl)-3-[N-methyl-N-(4-fluorophenyl) sulphamoyl]-1,2,4-triazole, an oil, $n_D^{27}$ 1.5223

1-(N-allyl-N-methylcarbamoyl)-3-[N-methyl-N-(4-fluorophenyl) sulphamoyl]-1,2,4-triazole, an oil, $n_D^{27}$ 1.5425

1-(N-ethyl-N-sec.butylcarbamoyl)-3-[N-methyl-N-(4-fluorophenyl)sulphamoyl]-1,2,4-triazole, an oil, $n_D^{26}$ 1.5260

1-(N-hexyl-N-methylcarbamoyl)-3-[N-methyl-N-(4-fluorophenyl) sulphamoyl]-1,2,4-triazole, an oil, $n_D^{26}$ 1.5222

1-(N-ethyl-N-propylcarbamoyl)-3-[N-methyl-N-(4-fluorophenyl) sulphamoyl]-1,2,4-traizole, m.p. 80° – 82°C.

1-(N-butyl-N-ethylcarbamoyl)-3-[N-methyl-N-(4-fluorophenyl) sulphamoyl]-1,2,4-triazole, m.p. 48° – 52°C.

1-(N-allyl-N-propylcarbamoyl)-3-[N-methyl-N-(4-fluorophenyl) sulphamoyl]-1,2,4-triazole, m.p. 76° – 77°C.

1-(N-butyl-N-methylcarbamoyl)-3-[N-methyl-N-(4-fluorophenyl)sulphamoyl]-1,2,4-triazole m.p. 87° – 89°C.

1-(N-methyl-N-cyclohexylcarbamoyl)-3-[N-methyl-N-(4-fluorophenyl)sulphamoyl]-1,2,4-triazole, m.p. 117° – 118°C.

1-(N-allyl-N-isobutylcarbamoyl)-3-[N-methyl-N-(4-fluorophenyl)sulphamoyl]-1,2,4-triazole, an oil, $n_D^{20}$ 1.530 (99.7% 1-isomer by GLC assay)

1-(N-methyl-N-propylcarbamoyl)-3-[N-methyl-N-(4-fluorophenyl) sulphamoyl]-1,2,4-triazole, m.p. 71° – 72.5°C.

1-diallycarbamoyl-3-[N-methyl-N-(4-fluorophenyl)-sulphamoyl]-1,2,4-triazole, m.p. 75° – 76°C.

1-diethylcarbamoyl-3-[N-ethyl-N-(4-fluorophenyl)-sulphamoyl]-1,2,4-triazole, m.p. 121° – 123°C.

1-diallylcarbamoyl-3-[N-ethyl-N-(4-chlorophenyl)-sulphamoyl]-1,2,4-triazole, m.p. 61° – 63°C.

1-diethylcarbamoyl-3-[N-ethyl-N-(4-chlorophenyl)-sulphamoyl]-1,2,4-triazole, m.p. 99° – 101°C.

Satisfactory elemental analyses were obtained for all the compounds listed above.

The following novel intermediate triazoles were prepared.

3-(N-propyl-N-isopropylsulphamoyl)-1,2,4-triazole, m.p. 167° – 168°C.

3-di-(2-ethoxyethyl)sulphamoyl-1,2,4-triazole, m.p. 79° – 80°C.

3-(N-propyl-N-hexylsulphamoyl)-1,2,4-triazole, m.p. 70° – 72°C.

3-(N-propyl-N-prop-2-ynylsulphamoyl)-1,2,4,-triazole, m.p. 164° – 166°C.

3-(N-propyl-N-2-chloroallylsulphamoyl)-1,2,4-triazole m.p. 137° – 138°C.

3-[N-propyl-N-(2-methoxyethyl)sulphamoyl]-1,2,4-triazole m.p. 86° – 88°C.

3-(N-allyl-N-hexylsulphamoyl)-1,2,4-triazole m.p. 95° – 96°C.

3-(N-cyclopropyl-N-ethylsulphamoyl)-1,2,4-triazole m.p. 153° – 155°C.

3-[N-allyl-N-(2-butoxyethyl)sulphamoyl]-1,2,4-triazole m.p. 69° – 71°C.

3-[N-ethyl-N-(2-allyloxyethyl)sulphamoyl]-1,2,4-triazole m.p. 124° – 125°C.

3-(N-methyl-N-pentylsulphamoyl)-1,2,4-triazole m.p. 124° – 125°C.

3-[N-ethyl-N-(2,3-dichloroallyl)sulphamoyl]-1,2,4-triazole m.p. 116° – 117°C.
3-(N-butyl-N-ethylsulphamoyl)-1,2,4-triazole, m.p. 101° – 103°C.
3-(N-allyl-N-propylsulphamoyl)-1,2,4-triazole, m.p. 125° – 127°C.
3-[N-ethyl-N-(2-methoxyethyl)sulphamoyl]-1,2,4-triazole m.p. 102° – 104°C.
3-(N-methyl-N-hexylsulphamoyl)-1,2,4-triazole, m.p. 123° – 124°C.
3-(N-ethyl-N-pentylsulphamoyl)-1,2,4-triazole, m.p. 111° – 113°C.
3-(N-ethyl-N-methylsulphamoyl)-1,2,4-triazole, m.p. 177° – 180°C.
3-(N-allyl-N-ethylsulphamoyl)-1,2,4-triazole, m.p. 131° – 132°C.
3-(N-ethyl-N-propylsulphamoyl)-1,2,4-triazole, m.p. 120° – 123°C.
3-(N-methyl-N-isobutylsulphamoyl)-1,2,4-triazole, m.p. 150° – 151°C.
3-(N-propyl-N-pentylsulphamoyl)-1,2,4-triazole, m.p. 61° – 62°C.
3-[N-methyl-N-(4-fluorophenyl)sulphamoyl]-1,2,4-triazole, m.p. 137.5° – 138.5°C.
3-[N-methyl-N-(4-chlorophenyl)sulphamoyl]-1,2,4-triazole, m.p. 156° – 157°C.

EXAMPLE 71

This Example illustrates the preparation of compounds of formula III.

A solution of 8.64 g. piperidinosulphonyl-1,2,4-triazole, 8 ml. triethylamine and 6.0 g. diethylcarbamoyl chloride in 25 ml. dry tetrahydrofuran was refluxed for 1½ hours.

Triethylamine hydrochloride precipitated and was filtered off. Light petroleum was added to the filtrate to precipitate the product which was separated and recrystallized from light petroleum (b.p. 80° – 100°C.). The product 1-diethylcarbamoyl-3-piperidinosulphonyl-1,2,4-triazole had a melting point of 108° – 110°C.

The triazole intermediate used in the above reaction was prepared as follows. Firstly the 1,2,4-triazole-3-sulphonyl chloride was prepared as in Example 70. The sulphonyl chloride thus prepared was gradually added with stirring to 100 ml. of water and 85 g. piperidine maintained at 15° – 20°C. A solution resulted. After 30 minutes, acidification with hydrochloric acid precipitated the product which was recrystallized from ethanol, giving a product with a melting point 196° – 198°C.

The following compounds were prepared in an analogous manner.

1-diethylcarbamoyl-3-(2,6-dimethylmorpholinosulphonyl)-1,2,4-triazole, m.p. 116° – 120°C.
1-(N-ethyl-N-butylcarbamoyl)-3-piperidinosulphonyl-1,2,4-triazole, an oil, $n_D^{20}$ 1.512
1-(N-propyl-N-propynylcarbamoyl)-3-piperidinosulphonyl-1,2,4-triazole, an oil, $n_D^{20}$ 1.5275
1-diallylcarbamoyl-3-hexamethyleneiminosulphonyl-1,2,4-triazole, m.p. 40° – 41°C.
1-diallylcarbamoyl-3-(4-methylpiperidino)sulphonyl-1,2,4-triazole, m.p. 64° – 65°C.
1-diallylcarbamoyl-3-heptamethyleneiminosulphonyl-1,2,4-triazole, m.p. 54° – 55°C.
1-(N-methyl-N-ethylcarbamoyl)-3-pyrrolidinosulphonyl-1,2,4-triazole, m.p. 83° – 84°C.
1-(N-ethyl-N-isopentylcarbamoyl)-3-piperidinosulphonyl-1,2,4-triazole, an oil, $n_D^{25}$ 1.4896 (96.3% 1-isomer by GLC assay)
1-(N-ethyl-N-prop-2-ynylcarbamoyl)-3-piperidinosulphonyl-1,2,4-triazole, m.p. 92° – 94°C.
1-(N-ethyl-N-pentylcarbamoyl)-3-piperidinosulphonyl-1,2,4-triazole, an oil, $n_D^{26}$ 1.5078 (98.9% 1-isomer by GLC assay)
1-(N-allyl-N-methylcarbamoyl)-3-piperidinosulphonyl-1,2,4-triazole, an oil, $n_D^{27}$ 1.5266 (99.6% 1-isomer by GLC assay)
1-(N-ethyl-N-sec.butylcarbamoyl)-3-piperidinosulphonyl-1,2,4-triazole, an oil, $n_D^{26}$ 1.5086 (95.3% 1-isomer by GLC assay)
1-(N-hexyl-N-methylcarbamoyl)-3-piperidinosulphonyl-1,2,4-triazole, an oil, $n_D^{26}$ 1.5070 (97.8% 1-isomer by GLC assay)
1-(N-methyl-N-propylcarbamoyl)-3-piperidinosulphonyl-1,2,4-triazole, m.p. 91° – 92.5°C.

Satisfactory elemental analyses were obtained for all the compounds listed above.

The following novel intermediate triazoles were prepared:

3-hexamethyleneiminosulphonyl-1,2,4-triazole, m.p. 203° – 204°C.
3-(4-methylpiperidyl)sulphonyl-1,2,4-triazole, m.p. 230° – 232°C.
3-heptamethyleneiminosulphonyl-1,2,4-triazole, m.p. 225° – 227°C.
3-pyrrolidinosulphonyl-1,2,4-triazole
3-(2,6-dimethylmorpholinosulphonyl-1,2,4-triazole

EXAMPLE 72

This Example illustrates the preparation of compounds of formula III.

A solution of 6.9 g. 3-diallylsulphamoyl-1,2,4-triazole, 6 ml. triethylamine and 5.9 g. N-propyl-N-(2-chloroallyl)carbamoyl chloride in 25 ml. dry tetrahydrofuran was refluxed for two hours.

Triethylamine hydrochloride precipitated and was filtered off. The filtrate was diluted with ether, washed twice with ice-cold 0.1N sodium hydroxide solution and once with water, dried over sodium sulphate and distilled to dryness, finally at 100°C/0.5 mm. The product 1-[N-propyl-N-(2-chloroallyl)carbamoyl]-3-diallylsulphamoyl-1,2,4-triazole was a viscous oily residue, $n_D^{20}$ 1.5230.

The following compounds were prepared in an analogous manner:

1-[N-propyl-N-(2-chloroallyl)carbamoyl]-3-diethylsulphamoyl-1,2,4-triazole, m.p. 50°C.
1-[N-propyl-N-(2-chloroallyl)carbamoyl]-3-(N-methyl-N-allylsulphamoyl)-1,2,4-triazole, an oil, $n_D^{20}$ 1.5216 (98.9% 1-isomer by GLC assay)
1-[N-ethyl-N-(2,3-dichloroallyl)carbamoyl]-3-diethylsulphamoyl-1,2,4-triazole, an oil, $n_D^{20}$ 1.5282 (98.6% 1-isomer by GLC assay)
1-[N-propyl-N-(2-chloroallyl)carbamoyl]-3-(N-methyl-N-butylsulphamoyl)-1,2,4-triazole, an oil, $n_D^{20}$ 1.512
1-[N-ethyl-N-(2-chloroallyl)carbamoyl]-3-diallylsulphamoyl-1,2,4-triazole, m.p. 63° – 64°C.
1-[N-ethyl-N-(2-chloroallyl)carbamoyl]-3-diethylsulphamoyl-1,2,4-triazole, m.p. 87° – 88°C.
1-[N-allyl-N-(2-chloroallyl)carbamoyl]-3-diethylsulphamoyl-1,2,4-triazole, m.p. 57° – 58°C.
1-[N-allyl-N-(2-chloroallyl)carbamoyl]-3-dimethylsulphamoyl-1,2,4-triazole, an oil, $n_D^{20}$ 1.527 (97.9% 1-isomer by GLC assay)

1-[N-ethyl-N-(2-chloroallyl)carbamoyl]-3-N-methyl-N-(4-fluorophenyl)sulphamoyl-1,2,4-triazole, an oil, $n_D^{20}$ 1.547 (94.9% 1-isomer by GLC assay)

Satisfactory elemental analyses were obtained for all the compounds listed above.

EXAMPLE 73

This Example illustrates the preparation of compounds of formula III.

A solution of 0.03 mole 3-diallylsulphamoyl-1,2,4-triazole, 8 ml. triethylamine and 0.03 mole of N-ethyl-N-2-methoxyethylcarbamoyl chloride in 40 ml. of dry tetrahydrofuran was held at room temperature for 3 days. The amine hydrochloride was filtered off and the solvent removed by evaporation. 100 ml. of petroleum ether were added to the mixture and petroleum ether decanted from the liquid layer formed. This was then dissolved in ether, filtered and the solvent removed by evaporation on the steam bath. The liquid product, 1-[N-ethyl-N-(2-methoxyethyl)carbamoyl]-3-diallyl-sulphamoyl-1,2,4-triazole was heated at 100°C. in vacuo for 3 hours at a pressure of lower than 0.2 mm. in order to remove all traces of carbamoyl chloride. The compound which was an oily liquid had a refractive index $n_D^{23}$ 1.5100. Assay by GLC showed that 96.1% of 1-isomer was present. Elemental analysis was satisfactory.

The 3-diallylsulphamoyl-1,2,4-triazole intermediate used in the above preparation was prepared as in Example 70.

The preparation of the carbamoyl chloride reactant was as follows.

N-ethyl-N-2-methoxyethylamine, b.p. 115° – –°C. was first prepared by reaction of 3 molecular proportions of ethylamine with 1 molecular proporation of 1-bromo-2-methoxyethane in aqueous solution containing 1 equivalent of sodium hydroxide at 30° – 50°C.

To a stirred solution of 89.1 g. phosgene in 500 ml. dry ether at −20°C. was added a solution of 30.9 g. N-ethyl-N-2-methoxyethylamine in 50 ml. dry ether, whilst the temperature of the reaction mixture was maintained at −20°C. The stirred mixture was then allowed to warm to room temperature during 1 hour. The reaction mixture was filtered and the filtrate evaporated in vacuo below 25°C. to remove the solvent and give the product, N-(2-methoxyethyl)-N-ethylcarbamoyl chloride as a pale yellow liquid.

The following compounds were prepared in an analogous manner.

1-[N-ethyl-N-(2-allyloxyethyl)carbamoyl]-3-diethylsulphamoyl-1,2,4-triazole, an oil, $n_D^{22}$ 1.5035 (98.4% 1-isomer by GLC assay)

1-[N-propyl-N-(2-methoxyethyl)carbamoyl]-3-diethylsulphamoyl-1,2,4-triazole, an oil, $n_D^{22}$ 1.4982 (97.5% 1-isomer by GLC asay)

1-[N-ethyl-N-(2-methoxyethyl)carbamoyl]-3-diallyl-sulphamoyl-1,2,4-triazole, an oil, $n_D^{23}$ 1.5100 (96.7% 1-isomer by GLC assay)

1-[N-ethyl-N-(2-methoxyethyl)carbamoyl]-3-diethylsulphamoyl-1,2,4-triazole, an oil, $n_D^{23}$ 1.5005 (96.8% 1-isomer by GLC assay)

1-[-N-ethyl-N-(3-methoxypropyl)carbamoyl]-3-diethylsulphamoyl-1,2,4-triazole, an oil, $n_D^{22}$ 1.4965 (97.8% 1 -isomer by GLC assay)

1-[N-ethyl-N-(3-methoxypropyl)carbamoyl]-3-diallylsulphamoyl-1,2,4-triazole, an oil, $n_D^{22}$ 1.5061 (96.6% 1-isomer by GLC assay)

1-(N-propyl-N-methoxymethylcarbamoyl)-3-diethylsulphamoyl-1,2,4-triazole, m.p. 37.5° – 38.5°C.

1-[N-propyl-N-(2-methoxyethyl)carbamoyl]-3-diallylsulphamoyl-1,2,4-triazole, an oil, $n_D^{28}$ 1.5025 (95.9% 1-isomer by GLC assay)

1-[N-propyl-N-(2-methoxyethyl)carbamoyl]-3-(N-butyl-N-methylsulphamoyl)-1,2,4-triazole, an oil, $n_D^{28}$ 1.4914 (96.0% 1-isomer by GLC assay)

1-[N-propyl-N-(2-methoxyethyl)carbamoyl]-3-piperidinosulphonyl-1,2,4-triazole, m.p. 73.5° – 75.5°C.

1-[N-propyl-N-(2-methoxyethyl)carbamoyl]-3-[N-methyl-N-(4-fluorophenyl)sulphamoyl]-1,2,4-triazole, an oil, $n_D^{28}$ 1.5224

1-[N-propyl-N-(2-ethoxyethyl)carbamoyl]-3-diethylsulphamoyl-1,2,4-triazole, an oil, $n_D^{23}$ 1.4925 (97.1% 1-isomer by GLC assay)

1-[N-propyl-N-(1-ethoxyethyl)carbamoyl]-3-(N-butyl-N-methylsulphamoyl-1,2,4-triazole, an oil, $n_D^{23}$ 1.4900 (97.1% 1-isomer by GLC assay)

1-[N-ethyl-N-(2-ethoxyethyl)carbamoyl]-3-diallyl-sulphamoyl-1,2,4-triazole, an oil $n_D^{23}$ 1.5026 (98.1% 1-isomer by GLC assay)

1-[N-ethyl-N-(2-ethoxyethyl)carbamoyl]-3-diethylsulphamoyl-1,2,4-triazole, an oil, $n_D^{23}$ 1.4930 (98.1% 1-isomer by GLC assay)

1-[N-ethyl-N-(2-ethoxyethyl)carbamoyl]-3-(N-butyl-N-methylsulphamoyl)-1,2,4-triazole, an oil, $n_D^{23}$ 1.4910 (97.8% 1-isomer by GLC assay)

1-[N-ethyl-N-(2-ethoxyethy(carbamoyl))-3-piperidinosulphonyl-1,2,4-triazozle, m.p. 73.5° – 77.5°C.

Satisfactory elemental analyses were obtained for all of the compounds listed above.

EXAMPLE 74

This Example illustrates compositions comprising a compound of formula III.

A dispersible powder was prepared by grinding together a mixture of the following ingredients in a hammer mill.

| | % w/w |
|---|---|
| 1-Diallylcarbamoyl-3-(1-piperidylsulphonyl)-1,2,4-triazole | 25.0 |
| Sodium N-methyl-N-palmitoyltaurate | 6.0 |
| Sodium di-octylsulphosuccinate | 0.5 |
| Colloidal silicic acid | 25.0 |
| Kaolin | 43.5 |

Similar dispersible powders were prepared using the following active ingredients in place of the triazole compound in the above formulation.

1-diallylcarbamoyl-3-dipropylsulphamoyl-1,2,4-triazole 1-diallylcarbamoyl-3-pyrrolidinosulphonyl-1,2,4-triazole 1-diethylcarbamoyl-3-diallylsulphamoyl-1,2,4-triazole 1-diallylcarbamoyl-3-diethylsulphamoyl-1,2,4-triazole 1-(N-allyl-N-ethylcarbamoyl)-3-(1-piperidylsulphonyl)-1,2,4-triazole 1-(N-methyl-N-cyclohexylcarbamoyl)-3-diethylsulphamoyl-1,2,4-triazole 1-(N-methyl-N-cyclohexylcarbamoyl)-3-diallylsulphamoyl-1,2,4-triazole 1-diallylcarbamoyl-3-(1-piperidylsulphonyl)-1,2,4-triazole

EXAMPLE 75

This Example illustrates compositions comprising a compound of formula III.

An emulsifiable concentrate suitable for dilution with water to form an aqueous emulsion was prepared from the following ingredients.

|  | % w/v |
|---|---|
| 1-Diallylcarbamoyl-3-(N-allyl-N-methylsulphamoyl)-1,2,4-triazole | 20.0 |
| Calcium dodecylbenzenesulphonate | 2.5 |
| Nonylphenoxypolyethoxyethanol * | 2.5 |
| Xylene | to 100.0 |

* A nonylphenol-ethylene oxide condensate containing an average of 14 mols. ethylene oxide per mol. nonylphenol.

A similar emulsifiable concentrate was prepared in which the triazole compound in the above formulation was replaced by the following compound.

1-(N-allyl-N-propylcarbamoyl)-3-diethylsulphamoyl-1,2,4-triazole.

EXAMPLE 76

This Example illustrates the use of compositions comprising a compound of formula III.

In tests carried out in the glasshouse, trays of soil were sown with seeds of various weeds and then immediately sprayed with aqeuous suspensions of compounds under test at various application rates of test compound. Seeded trays of soil receiving no chemical treatment were used as controls. At an application rate of 0.5 lb./acre, all the triazoles mentioned in Examples 74 and 75 controlled the weeds crabgrass, barnyard grass, yellow foxtail and Johnson grass (no germination or emergent seedlings severely and irrecoverable stunted).

EXAMPLE 77

This Example illustrates the use of herbicidal compositions comprising a compound of the formula II Compositions were prepared containing the following compounds as active ingredients:

1-(N-propyl-N-prop-2-ynylcarbamoyl)-3-(2-ethoxyethyl-sulphonyl)-1,2,4-triazole.
1-[N-butyl-N(2-methoxyethyl)carbamoyl]-3-propylsulphonyl-1,2,4-triazole.
1-[N-allyl-N-(2-ethoxyethyl)carbamoyl]-3-butylsulphonyl-1,2,4-triazole.
1-(N-butyl-n-ethylcarbamoyl)-3-(2-ethoxyethylsulphonyl)-1,2,4-triazole.
1-(N-cyclopropyl-N-propylcarbamoyl)-3-butylsulphonyl-1,2,4-triazole.

Rice seedlings were grown under paddy conditions in the glasshouse. At the 2–3 leaf stage the trays containing the seedlings were seeded with barnyard grass and then sprayed with aqueous emulsions prepared from the above concentates, at an application rate of active ingredient of one/eighth lb./acre. After seven days the trays were flooded with water and examined 21 days after spraying.

No barnyard grass was observed in the trays sprayed with the aqueous emulsions described above, and no lasting phytotoxic effect on the rice plants was observed. A growth of barnyard grass had occurred in control trays that had received no chemical treatment.

EXAMPLE 78

This Example illustrates the use of herbicidal compositions comprising a compound of the formula III Compositions were prepared containing the following compounds as active ingredients:

1-(N-butyl-N-ethylcarbamoyl)-3-(N-allyl-N-methylsulphamoyl)-1,2,4-triazole.
1-(N-ethyl-N-methylcarbamoyl)-3-pyrrolidinosulphonyl-1,2,4-triazole.
1-(N-allyl-N-ethylcarbamoyl)-3-diallylsulphamoyl-1,2,4-triazole.
1-diethylcarbamoyl-3-diallylsulphamoyl-1,2,4-triazole.
1-(N-allyl-N-propylcarbamoyl)-3-diethylsulphamoyl-1,2,4-striazole.

Rice seedlings were grown under paddy conditions in the glasshouse. At the 2–3 leaf stage the trays containing the seedlings were seeded with barnyard grass and then sprayed with aqueous emulsions prepared from the above concentrates, at an application rate of active ingredient of one-eighth lb./acre. After seven days the trays were flooded with water and examined 21 days after spraying.

No barnyard grass was observed in the trays sprayed with the aqueous emulsions described above, and no lasting phytotoxic effect on the rice plants was observed. A growth of barnyard grass had occurred in control trays that had received no chemical treatment.

We claim:

1. A compound of the formula $$\underset{R^3}{\overset{N\longrightarrow N-CONR^1R^2}{\underset{N}{\parallel}}}$$

in which $R^3$ is selected from the group consisting of alkylthio containing 2 – 5 carbon atoms, alkylsulphinyl containing 3 – 5 carbon atoms, alkylsulphonyl containing 1 – 5 carbon atoms and alkenylthio containing 3 – 4 carbon atoms, $R^1$ is selected from the group consisting of alkyl containing 2 – 6 carbon atoms, allyl and 2-methylallyl and $R^2$, which together with $R^1$ contains a total of 4 – 9 carbon atoms, is selected from the group consisting of alkyl containing 2 – 3 carbon atoms, allyl, 2-methylallyl and prop-2-ynyl.

2. A compound to claim 1 in which $R^3$ is alkylsulphonyl containing 1–5 carbon atoms and the carbamoyl group $CONR^1R^2$ contains 5–10 carbon atoms and is selected from the group consisting of diallylcarbamoyl, dialkyl carbamoyl, N-allyl-N-alkylcarbamoyl and N-alkyl-N-prop-2-ynylcarbamoyl.

3. A compound according to claim 2 in which $R^3$ contains 1 – 4 carbon atoms and the carbamoyl group is diallylcarbamoyl.

4. A compound according to claim 2 in which $R^3$ contains 1 – 4 carbon atoms and the carbamoyl group is dialkylcarbamoyl wherein the alkyl radicals are the same or different.

5. A compound according to claim 2 in which $R^3$ contains 1 – 4 carbon atoms and the carbamoyl group is selected from the group consisting of dipropylcarbamoyl, N-propyl-N-isopropylcarbamoyl, di-isopropylcarbamoyl and N-ethyl-N-propylcarbamoyl.

6. A compound according to claim 2 in which $R^3$ contains 1 – 4 carbon atoms and the carbamoyl group is selected from the group consisting of N-allyl-N-ethylcarbamoyl and N-allyl-N-propylcarbamoyl.

7. A compound to claim 1 in which $R^3$ is alkylsulphinyl containing 3–5 carbon atoms and the carbamoyl group $CONR^1R^2$ contains 5–10 carbon atoms and is selected from the group consisting of diallylcarbamoyl, dialkylcarbamoyl, -N-allyl-N-alkylcarbamoyl and N-alkyl-N-prop-2-ynylcarbamoyl.

8. A compound according to claim 7 in which $R^3$ contains 3 – 4 carbon atoms and the carbamoyl group is selected from the group consisting of diallylcarbamoyl and dipropylcarbamoyl.

9. A compound to claim 1 in which $R^3$ is alkylthio containing 2–5 carbon atoms and the carbamoyl group $CONR^1R^2$ contains 5–10 carbon atoms and is selected from the group consisting of diallylcarbamoyl, N-allyl-N-alkylcarbamoyl and N-alkyl-N-prop-2-ynylcarbamoyl.

10. A compound according to claim 9 in which $R^3$ contains 2 – 4 carbon atoms and the carbamoyl group is diallylcarbamoyl.

11. 1-(N-ethyl-N-propylcarbamoyl)-3-propylsulphonyl-1,2,4-triazole.

* * * * *